United States Patent
Cheresh et al.

(10) Patent No.: US 6,685,938 B1
(45) Date of Patent: Feb. 3, 2004

(54) METHODS AND COMPOSITIONS USEFUL FOR MODULATION OF ANGIOGENESIS AND VASCULAR PERMEABILITY USING SRC OR YES TYROSINE KINASES

(75) Inventors: David A. Cheresh, Encinitas, CA (US); Brian Eliceiri, Carlsbad, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/470,881

(22) Filed: Dec. 22, 1999

Related U.S. Application Data

(63) Continuation-in-part of application No. PCT/US99/11780, filed on May 28, 1999.
(60) Provisional application No. 60/087,220, filed on May 29, 1998.

(51) Int. Cl.[7] .................... A61K 38/45; A61K 38/17; C12N 9/12
(52) U.S. Cl. ................. 424/94.5; 514/12; 435/194
(58) Field of Search .................. 424/94.5; 514/12; 435/194

(56) References Cited

FOREIGN PATENT DOCUMENTS

WO     99/61590     * 12/1999

OTHER PUBLICATIONS van Bruggen, N. et al., 1999, "VEGF antagonism reduces edema formation and tissue damage after ischemia/reperfusion injury in the mouse brain" *J. Clin. Invest.* 104:1613–1620.

Hanke, J.H. et al., 1996, "Discovery of a novel, potent, and Src family–selective tyrosine kinase inhibitor" *J. Biol. Chem.* 271(2): 59: 6145–6152.

Moasser, M.M. et al., 1999, "Inhibition of Src kinases by a selective tyrosine kinase inhibitor causes mitotic arrest" *Cancer Res.* 59:6145–6152

Owens, D.W. et al., 2000, "The catalytic activity of the Src family kinases is required to disrupt cadherin–dependent cell–cell contacts" *Mol. Biol. Cell* 11: 51–64.

Rak, J. et al., 1995, "Oncogenes as inducers of tumor angiogenesis" *Cancer and Metastasis Reviews* 14(4): 263–277.

Senger et al., 1983, "Tumor cells secrete a vascular permeability factor that promotes accumulation of ascities fluid" *Science* 219:983–985.

Maly et al., 2000, "Combinatorial target–guided ligand assembly: Identification of potent subtype–selective c–Src inhibitors" *PNAS (USA)* 97(6): 2419–2424.

H.He et al., "Vascular Endothelial Growth Factor Signals Endothelial Cell Production of Nitric Oxide and Prostacyclin Through Flk–1/KDR Activation of c–Src", *J. Biol. Chem.* 274(35): 25130–25135 (Aug. 1999).*

B.P. Eliceiri et al. "Requirement For Src Activity During VEGF But Not bFGF–Induced Angiogenesis", *Mol. Biol. Cell* 9, Supp. p. 442a, Abstract 2444. (Nov. 1998).*

* cited by examiner

*Primary Examiner*—Rebecca E. Prouty
(74) *Attorney, Agent, or Firm*—Olson & Hierl, Ltd.

(57) ABSTRACT

The present invention describes methods for modulating vascular permeability (VP) in tissues using Src or modified Src protein, Yes protein or modified Yes protein, or mixtures thereof, and nucleic acids capable of expression such proteins. In particular, the invention describes methods for inhibiting VP using an inactive Src or Yes protein or a mixture thereof, or nucleic acids encoding therefor, or for potentiating VP using an active, Src or Yes protein or a mixture thereof, or nucleic acids encoding therefor. Related compositions and articles of manufacture are also disclosed.

16 Claims, 15 Drawing Sheets

CHICKEN c-SRC cDNA (SEQ ID NO:2)

```
   1 tctgacaccc atctgtctgt ctgtctgtgt gctgcaggag ctgagctgac tctgctgtgg
  61 cctcgcgtac cactgtggcc aggcggtagc tgggacgtgc agcccaccac catggggagc
 121 agcaagagca agcccaagga ccccagccag cgccggcgca gcctggagcc accgacacgc
 181 acccaccacg ggggattccc agcctcgcag acccccaaca agacagcagc cccgacacg
 241 caccgcaccc ccagccgctc ctttgggacc gtggccaccg agcccaagct cttcggggc
 301 ttcaacactt ctgacaccgt tacgtcgccg cagcgtgccg gggcactggc tggcggcgtc
 361 accactttcg tggctctcta cgactacgag tcccggactg aaacggactt gtccttcaag
 421 aaaggagaac gcctgcagat tgtcaacaac acggaaggtg actggtggct ggctcattcc
 481 ctcactacag gacagacggg ctacatcccc agtaactatg tgcgccctc agactccatc
 541 caggctgaag agtggtactt tgggaagatc actcgtcggg agtccgagcg gctgctgctc
 601 aaccccgaaa accccggggg aaccttcttg gtccgggaga gcgagacgac aaaaggtgcc
 661 tattgcctct ccgtttctga ctttgacaac gccaaggggc tcaatgtgaa gcactacaag
 721 atccgcaagc tggacagcgg cggcttctac atcacctcac gcacacagtt cagcagcctg
 781 cagcagctgg tggcctacta ctccaaacat gctgatggct gtgccaccg cctgaccaac
 841 gtctgcccca cgtccaagcc ccagacccag ggactcgcca aggacgcgtg ggaaatcccc
 901 cgggagtcgc tgcggctgga ggtgaagctg gggcagggct gctttggaga ggtctggatg
 961 gggacctgga acggcaccac cagagtggcc ataaagactc tgaagcccgg caccatgtcc
1021 ccggaggcct tctgcagga gcccaagtg atgaagaagc tccggcatga gaagctggtt
1081 cagctgtacg cagtggtgtc ggaagagccc atctacatcg tcactgagta catgagcaag
1141 gggagcctcc tggatttcct gaagggagag atgggcaagt acctgcggct gccacagctc
1201 gtcgatatgg ctgctcagat tgcatccggc atggcctatg tggagaggat gaactacgtg
1261 caccgagacc tgcgggcggc caacatcctg gtgggggaga acctggtgtg caaggtggct
1321 gactttgggc tggcacgcct catcgaggac aacgagtaca gcacggca aggtgccaag
1381 ttccccatca gtggacagc ccccgaggca gccctctatg gccggttcac catcaagtcg
1441 gatgtctggt ccttcggcat cctgctgact gagctgacca ccaagggccg ggtgccatac
1501 ccagggatgg tcaacaggga ggtgctggac caggtggaga ggggctaccg catgccctgc
1561 ccgcccgagt gccccgagtc gctgcatgac ctcatgtgcc agtgctggcg gagggaccct
1621 gaggagcggc cacttttga gtacctgcag gccttcctgg aggactactt cacctcgaca
1681 gagccccagt accagcctgg agagaaccta taggcctgga gctcctcctg gaccagaggc
1741 ctcgctgtgg ggtacaggg
```

FIG. 1

CHICKEN cSRC ENCODED PROTEIN (SEQ ID NO:3)

MGSSKSKPKDPSQRRRSLEPPDSTHHGGFPASQTPNKTAA

PDTHRTPSRSFGTVATEPKLFGGFNTSDTVTSPQRAGALA

GGVTTFVALYDYESRTETDLSFKKGERLQIVNNTEGDWWL

AHSLTTGQTGYIPSNYVAPSDSIQAEEWYFGKITRRESER

LLLNPENPRGTFLVRESETTKGAYCLSVSDFDNAKGLNVK

HYKIRKLDSGGFYITSRTQFSSLQQLVAYYSKHADGLCHR

LTNVCPTSKPQTQGLAKDAWEIPRESLRLEVKLGQGCFGE

VWMGTWNGTTRVAIKTLKPGTMSPEAFLQEAQVMKKLRHE

KLVQLYAVVSEEPIYIVTEYMSKGSLLDFLKGEMGKYLRL

PQLVDMAAQIASGMAYVERMNYVHRDLRAANILVGENL

VCKVADFGLARLIEDNEYTARQGAKFPIKWTAPEAALYGR

FTIKSDVWSFGILLTELTTKGRVPYPGMVNREVLDQVERG

YRMPCPPECPESLHDLMCQCWRRDPEERPTFEYLQAFLE

DYFTSTEPQYQPGENL

FIG. 2

HUMAN c-SRC cDNA (SEQ ID NO:4)

```
   1 gcgccgcgtc ccgcaggccg tgatgccgcc cgcgcggagg tggcccggac cgcagtgccc
  61 caagagagct ctaatggtac caagtgacag gttggcttta ctgtgactcg gggacgccag
 121 agctcctgag aagatgtcag caatacaggc cgcctggcca tccggtacag aatgtattgc
 181 caagtacaac ttccacggca ctgccgagca ggacctgccc ttctgcaaag gagacgtgct
 241 caccattgtg gccgtcacca aggacccaa ctggtacaaa gccaaaaaca aggtgggccg
 301 tgagggcatc atcccagcca actacgtcca gaagcgggag ggcgtgaagg cgggtaccaa
 361 actcagcctc atgccttggt tccacggcaa gatcacacgg gagcaggctg agcggcttct
 421 gtaccgccg gagacaggcc tgttcctggt gcgggagagc accaactacc ccggagacta
 481 cacgctgtgc gtgagctgcg acggcaaggt ggagcactac cgcatcatgt accatgccag
 541 caagctcagc atcgacgagg aggtgtactt tgagaacctc atgcagctgg tggagcacta
 601 cacctcagac gcagatggac tctgtacgcg cctcattaaa ccaaaggtca tggagggcac
 661 agtggcggcc caggatgagt tctaccgcag cggctgggcc ctgaacatga aggagctgaa
 721 gctgctgcag accatcggga aggggggagtt cggagacgtg atgctgggcg attaccgagg
 781 gaacaaagtc gccgtcaagt gcattaagaa cgacgccact gcccaggcct cctggctga
 841 agcctcagtc atgacgcaac tgcggcatag caacctggtg cagctcctgg gcgtgatcgt
 901 ggaggagaag ggcgggctct acatcgtcac tgagtacatg gccaagggga gccttgtgga
 961 ctacctgcgg tctagggggtc ggtcagtgct gggcggagac tgtctcctca gttctcgct
1021 agatgtctgc gaggccatgg aatacctgga gggcaacaat ttcgtgcatc gagacctggc
1081 tgcccgcaat gtgctggtgt ctgaggacaa cgtggccaag gtcagcgact tggtctcac
1141 caaggaggcg tccagcaccc aggacacggg caagctgcca gtcaagtgga cagcccctga
1201 ggccctgaga gagaagaaat ctcccactaa gtctgacgtg tggagtttcg gaatccttct
1261 ctgggaaatc tactccttg ggcgagtgcc ttatccaaga attcccctga aggacgtcgt
1321 ccctcgggtg gagaagggct acaagatgga tgcccccgac ggctgcccgc ccgcagtcta
1381 tgaagtcatg aagaactgct ggcacctgga cgccgccatg cggcctcct tctacaagct
1441 ccgagagcag cttgagcaca tcaaaaccca cgagctgcac ctgtgacggc tggcctccgc
1501 ctgggtcatg ggctgtggg gactgaacct ggaagatcat ggacctggtg ccctgctca
1561 ctgggcccga gcctgaactg agccccagcg ggctggcggg ccttttcct gcgtcccagc
1621 ctgcacccct ccggccccgt ctctcttgga cccacctgtg gggcctgggg agcccactga
1681 ggggccaggg aggaaggagg ccacggagcg ggaggcagcg ccccaccacg tcgggcttcc
1741 ctggcctccc gccactcgcc ttcttagagt tttattcctt tccttttttg agattttt
1801 tccgtgtgtt tattttttat tattttcaa gataaggaga aagaaagtac ccagcaaatg
1861 ggcattttac aagaagtacg aatcttattt ttcctgtcct gcccgtgagg gtggggggga
1921 ccgggcccct ctctagggac ccctcgcccc agcctcattc cccattctgt gtcccatgtc
1981 ccgtgtctcc tcggtcgccc cgtgtttgcg cttgaccatg ttgcactgtt tgcatgcgcc
2041 cgaggcagac gtctgtcagg ggcttggatt tcgtgtgccg ctgccacccg cccacccgcc
2101 ttgtgagctg gaattgtaat aaaccacgcc atgaggacac cgccgcccgc ctcggcgctt
2161 cctccaccga aaaaaaaaa aaaaaaa
```

FIG. 3

HUMAN c-SRC ENCODED PROTEIN (SEQ ID NO:5)

MSAIQAAWPSGTECIAKYNFHGTAEQDLPFCKGDVLTIVAVTKD

PNWYKAKNKVGREGIIPANYVQKREGVKAGTKLSLMPWFHGKIT

REQAERLLYPPETGLFLVRESTNYPGDYTLCVSCDGKVEHYRIMY

HASKLSIDEEVYFENLMQLVEHYTSDADGLCTRLIKPKVMEGTVA

AQDEFYRSGWALNMKELKLLQTIGKGEFGDVMLGDYRGNKVAV

KCIKNDATAQAFLAEASVMTQLRHSNLVQLLGVIVEEKGGLYIVTE

YMAKGSLVDYLRSRGRSVLGGDCLLKFSLDVCEAMEYLEGNNFVH

RDLAARNVLVSEDNVAKVSDFGLTKEASSTQDTGKLPVKWTAPEAL

REKKFSTKSDVWSFGILLWEIYSFGRVPYPRIPLKDVVPRVEKGYKM

DAPDGCPPAVYEVMKNCWHLDAAMRPSFLQLREQLEHIKTHELHL

FIG. 4

Effect of RCAS-mediated expression of
Src A on angiogenesis in the chick CAM

Retroviral expression of Src A activates vascular MAP kinase phosphorylation

Selective requirement for Src activity during VEGF, but not bFGF-induced angiogenesis
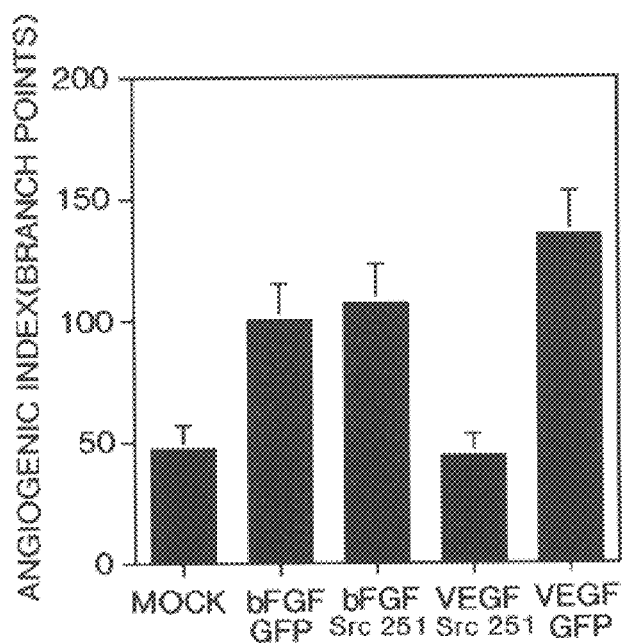
FIG. 8A
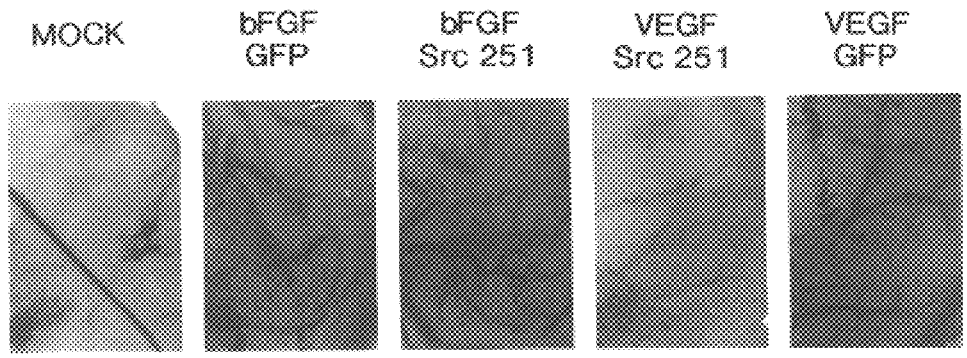
FIG. 8B
FIG. 8C human Yes-1 Protein amino acid sequence

"MGCIKSKENKSPAIKYRPENTPEPVSTSVSHYGAEPTTVSPCPS
SSAKGTAVNFSSLSMTPFGGSSGVTPFGGASSSFSVVPSSYPAGLTGGVTIFVALYDY
EARTTEDLSFKKGERFQIINNTEGDWWEARSIATGKNGYIPSNYVAPADSIQAEEWYF
GKMGRKDAERLLLNPGNQRGIFLVRESETTKGAYSLSIRDWDEIRGDNVKHYKIRKLD
NGGYYITTRAQFDTLQKLVKHYTEHADGLCHKLTTVCPTVKPQTQGLAKDAWEIPRES
LRLEVKLGQGCFGEVWMGTWNGTTKVAIKTLKPGTMMPEAFLQEAQIMKKLRHDKLVP
LYAVVSEEPIYIVTEFMSKGSLLDFLKEGDGKYLKLPQLVDMAAQIADGMAYIERMNY
IHRDLRAANILVGENLVCKIADFGLARLIEDNEYTARQGAKFPIKWTAPEAALYGRFT
IKSDVWSFGILQTELVTKGRVPYPGMVNREVLEQVERGYRMPCPQGCPESLHELMNLC
WKKDPDERPTFEYIQSFLEDYFTATEPQYQPGENL"

FIG. 11

```
   1 gcggagccaa ggcacacggg tctgacccTT gggccggccc ggagcaagtg acacggaccg
  61 gtcgcctatc ctgaccacag caaagcggcc cggagcccgc ggaggggacc tgacgggggc
 121 gtaggcgccg gaaggctggg ggccccggag ccgggccggc gtggcccgag ttccggtgag
 181 cggacggcgg cgcgcgcaga tttgataatg ggctgcatta aaagtaaaga aaacaaaagt
 241 ccagccatta aatacagacc tgaaaatact ccagagcctg tcagtacaag tgtgagccat
 301 tatggagcag aacccactac agtgtcacca tgtccgtcat cttcagcaaa gggaacagca
 361 gttaatttca gcagtctttc catgacacca tttggaggat cctcagggt aacgccTTtt
 421 ggaggtgcat cttcctcatt ttcagtggtg ccaagttcat atcctgctgg tttaacaggt
 481 ggtgttacta tatttgtggc cttatatgat tatgaagcta gaactacaga agacctttca
 541 tttaagaagg gtgaaagatt tcaaataatt aacaatacgg aaggagattg gtgggaagca
 601 agatcaatcg ctacaggaaa gaatggttat atcccgagca attatgtagc gcctgcagat
 661 tccattcagg cagaagaatg gtattttggc aaaatgggga gaaagatgc tgaaagatta
 721 cttttgaatc ctggaaatca acgaggtatt ttcttagtaa gagagagtga aacaactaaa
 781 ggtgcttatt ccctttctat tcgtgattgg gatgagataa ggggtgacaa tgtgaaacac
 841 tacaaaatta ggaaacttga caatggtgga tactatatca caaccagagc acaatttgat
 901 actctgcaga aattggtgaa acactacaca gaacatgctg atggtttatg ccacaagttg
 961 acaactgtgt gtccaactgt gaaacctcag actcaaggtc tagcaaaaga tgcttgggaa
1021 atccctcgag aatctttgcg actagaggtt aaactaggac aaggatgttt cggcgaagtg
1081 tggatgggaa catggaatgg aaccacgaaa gtagcaatca aaacactaaa accaggtaca
1141 atgatgccag aagcttTcct tcaagaagct cagataatga aaaattaag acatgataaa
1201 cttgttccac tatatgctgt tgtttctgaa gaaccaattc acattgtcac tgaatttatg
1261 tcaaaaggaa gcttattaga tttccttaag gaaggagatg gaaagtattt gaagcttcca
1321 cagctggttg atatggctgc tcagattgct gatggtatgg catatattga aagaatgaac
1381 tatattcacc gagatcttcg ggctgctaat attcttgtag gagaaaatct tgtgtgcaaa
1441 atagcagact ttggttTagc aaggttaatt gaagacaatg aatacacagc aagacaaggt
1501 gcaaaattTc caatcaaatg gacagctcct gaagctgcac tgtatggtcg gtttacaata
1561 aagtctgatg tctggtcatt tggaattctg caaacagaac tagtaacaaa gggccgagtg
1621 ccatatccag gtatggtgaa ccgtgaagta ctagaacaag tggagcgagg atacaggatg
1681 ccgtgccctc aggggctgcc agaatccctc catgaattga tgaatctgtg ttggaagaag
1741 gaccctgatg aaagaccaac atttgaatat attcagtcct tcttggaaga ctacttcact
1801 gctacagagc cacagtacca gccaggagaa aatttatcat tcaagtagcc tatttTatat
1861 gcacaaatct gccaaaatat aaagaacttg tgtagatttt ctacaggaat caaaagaaga
1921 aaatcttctt tactctgcat gttttTaatg gtaaactgga atcccagata tggttgcaca
1981 aaaccactTT tttttcccca agtattaaac tctaatgtac caatgatgaa tTTatcagcg
2041 tatttcaggg tccaaacaaa atagagctaa gatactgatg acagtgtggg tgacagcatg
2101 gtaatgaagg acagtgaggc tcctgcttat ttataaatca tTTccttTct ttTTTtcccc
2161 aaagtcagaa ttgctcaaag aaaaTTattt attgttacag ataaaacTTg agagataaaa
2221 agctatacca taataaaatc taaaattaag gaatcatg ggaccaaata attccattcc
2281 agtttTTtaa agtttcttgc atttattatt ctcaaaagtt tTTtctaagt taaacagtca
2341 gtatgcaatc ttaatatatg ctttcttTTg catggacatg ggccaggtTT tcaaaagga
2401 atataaacag gatctcaaac ttgattaaat gttagaccac agaagtggaa tttgaaagta
2461 taatgcagta cattaatatt catgttcatg gaactgaaag aataagaact tTTtcactTc
2521 agtccttTTc tgaagagttt gacttagaat aatgaaggta actagaaagt gagttaatct
2581 tgtatgaggt tgcattgatt tTTaaggca atatataatt gaaactactg tccaatcaaa
2641 ggggaaatgt tTTgatcttt agatagcatg caaagtaaga cccagcattT taaaagccct
2701 tTTTTaaaaa ctagacttcg tactgtgagt attgcTTata tgtccttatg gggatgggtg
2761 ccacaaatag aaaatatgac cagatcaggg acttgaatgc actTTTgctc atggtgaata
2821 tagatgaaca gagaggaaaa tgtatTTaaa agaaatacga gaaaagaaaa tgtgaaagTT
2881 tTacaagtta gagggatgga aggtaatgtt taatgttgat gtcatggagt gacagaatgg
2941 ctTTgctggc actcagagct cctcacttag ctatattctg agactTTgaa gagttataaa
3001 gtataactat aaaactaatt tTTcttacac actaaatggg tatTTgttca aaataatgaa
3061 gTTatggctT cacattcatt gcagtgggat atggttTTTa tgtaaaacat tTTTagaact
3121 ccagtttTca aatcatgTTT gaatctacat tcactTTTTT tTgtTTTctt tTTTgagacg
3181 gagtctcgct ctgccgccca ggctgagtg cagtggcgcg atctcggctc actgcaagct
3241 ctgcctccca ggttcacacc attctcctgc ctcagcctcc cgagtagctg ggactacagg
3301 tgcccaccac cacgcctggc tagtTTTTTg tatTTTTagt agagacgcag tTTcaccgtg
3361 TTagccagga tggtctcgat ctcctgacct tgtgatctgc ccgcctcggc ctcccaaagt
3421 gctgggatta caggtgtgag ccaccgcgcc cagcctacat tcactTctaa agtctatgta
```

FIG. 12A

```
3481 atggtggtca ttttttccct tttagaatac attaaatggt tgatttgggg aggaaaactt
3541 attctgaata ttaacggtgg tgaaaagggg acagttttta ccctaaagtg caaaagtgaa
3601 acatacaaaa taagactaat ttttaagagt aactcagtaa tttcaaaata cagatttgaa
3661 tagcagcatt agtggtttga gtgtctagca aaggaaaaat tgatgaataa aatgaaggtc
3721 tggtgtatat gttttaaaat actctcatat agtcacactt taaattaagc cttatattag
3781 gcccctctat tttcaggata taattcttaa ctatcattat ttacctgatt ttaatcatca
3841 gattcgaaat tctgtgccat ggcgtatatg ttcaaattca aaccatlttt aaaatgtgaa
3901 gatggacttc atgcaagttg gcagtggttc tggtactaaa aattgtggtt gttttttctg
3961 tttacgtaac ctgcttagta ttgacactct ctaccaagag ggtcttccta agaagagtgc
4021 tgtcattatt tcctcttatc aacaacttgt gacatgagat tttttaaggg ctttatgtga
4081 actatgatat tgtaattttt ctaagcatat tcaaaagggt gacaaaatta cgttatgta
4141 ctaaatctaa tcaggaaagt aaggcaggaa aagttgatgg tattcattag gttttaactg
4201 aatggagcag ttccttatat aataacaatt gtatagtagg gataaaacac taacaatgtg
4261 tattcatttt aaattgttct ctattttaa attgccaaga aaaacaactt tgtaaatttg
4321 gagatatttt ccaacagctt ttcgtcttca gtgtcttaat gtggaagtta acccttacca
4381 aaaaggaag ttggcaaaaa cagccttcta gcacactttt ttaaatgaat aatggtagcc
4441 taaacttaat atttttataa agtattgtaa tattgttttg tggataattg aaataaaaag
4501 ttctcattga atgcacc
```

FIG. 12B

FIG. 14A
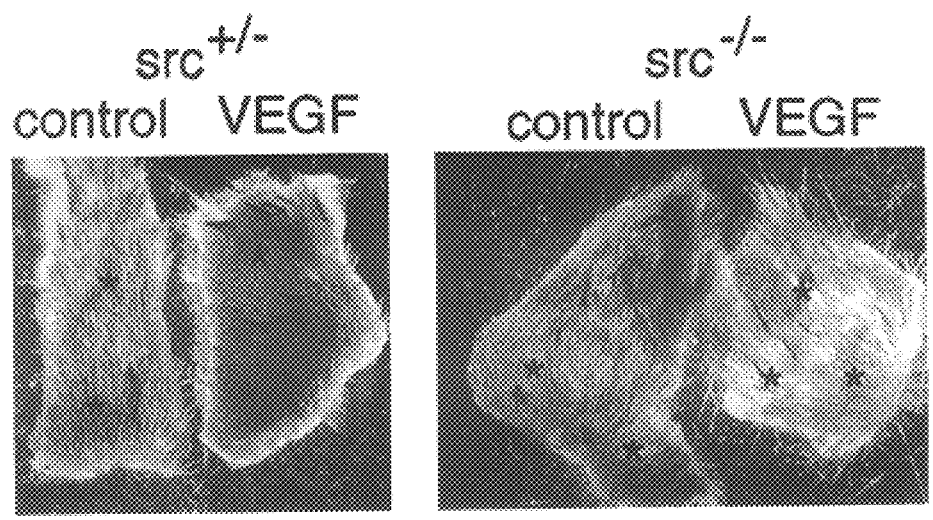
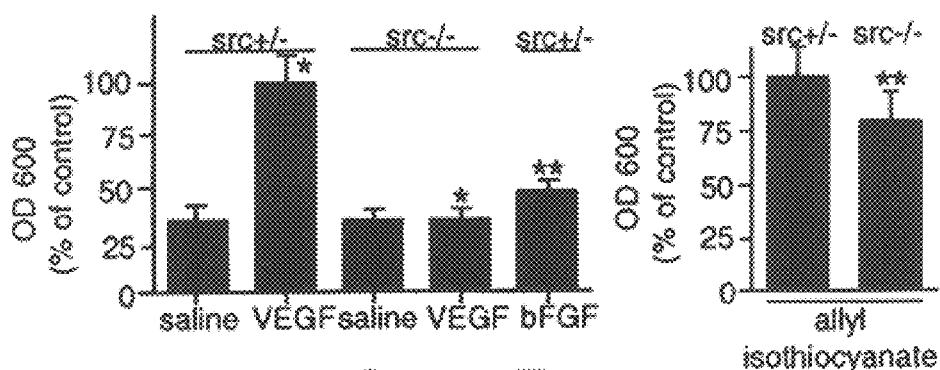
FIG. 14B
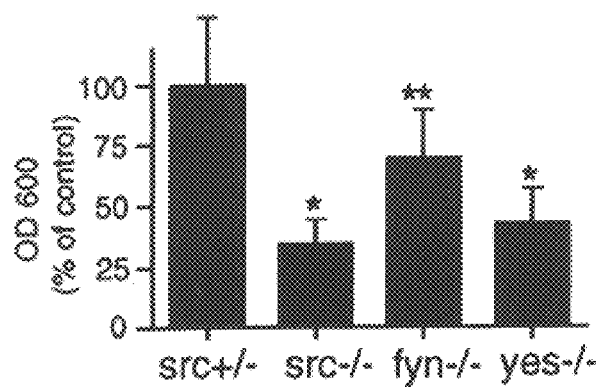
FIG. 14C

SEQUENCE LISTING

<160> NUMBER OF SEQ ID NOS: 8

<210> SEQ ID NO 1
<211> LENGTH: 11627
<212> TYPE: DNA
<213> ORGANISM: Artificial Sequence
<220> FEATURE:
<223> OTHER INFORMATION: Description of Artificial Sequence: RCASBP(A)

```
        based on avian sarcoma virus
<221> NAME/KEY: misc_feature
<222> LOCATION: (7649)..(11258)
<223> OTHER INFORMATION: pBR322 sequences
<221> NAME/KEY: LTR
<222> LOCATION: (7166)..(7494)
<223> OTHER INFORMATION: upstream
<221> NAME/KEY: LTR
<222> LOCATION: (1)..(101)
<223> OTHER INFORMATION: upstream (numbering begins at the upstream R)
<221> NAME/KEY: misc_feature
<222> LOCATION: (11394)..(11623)
<223> OTHER INFORMATION: U3
<221> NAME/KEY: misc_feature
<222> LOCATION: (1)..(21)
<223> OTHER INFORMATION: R
<221> NAME/KEY: misc_feature
<222> LOCATION: (22)..(101)
<223> OTHER INFORMATION: U5
<221> NAME/KEY: misc_feature
<222> LOCATION: (102)..(119)
<221> NAME/KEY: LTR
<222> LOCATION: (7166)..(7494)
<223> OTHER INFORMATION: downstream
<221> NAME/KEY: misc_feature
<222> LOCATION: (7166)..(7393)
<223> OTHER INFORMATION: U3
<221> NAME/KEY: misc_feature
<222> LOCATION: (7394)..(7414)
<223> OTHER INFORMATION: R
<221> NAME/KEY: misc_feature
<222> LOCATION: (7415)..(7494)
<223> OTHER INFORMATION: U5
<221> NAME/KEY: misc_feature
<222> LOCATION: (7154)..(7165)
<223> OTHER INFORMATION: PPT
<221> NAME/KEY: misc_feature
<222> LOCATION: (388)..(391)
<223> OTHER INFORMATION: splice donor (AGGT)
<221> NAME/KEY: misc_feature
<222> LOCATION: (5074)..(5077)
<223> OTHER INFORMATION: env splice acceptor (AGGC)
<221> NAME/KEY: misc_feature
<222> LOCATION: (6982)..(6985)
<223> OTHER INFORMATION: ClaI splice acceptor (AGGA)
<221> NAME/KEY: gene
<222> LOCATION: (372)..(902)
<223> OTHER INFORMATION: gag p19
<221> NAME/KEY: gene
<222> LOCATION: (909)..(1094)
<223> OTHER INFORMATION: gag p10
<221> NAME/KEY: gene
<222> LOCATION: (1095)..(1814)
<223> OTHER INFORMATION: gag p27
<221> NAME/KEY: gene
<222> LOCATION: (1843)..(2108)
<223> OTHER INFORMATION: gag p12
<221> NAME/KEY: gene
<222> LOCATION: (2109)..(2480)
<223> OTHER INFORMATION: gag p15
<221> NAME/KEY: misc_signal
<222> LOCATION: (2481)..(2483)
<223> OTHER INFORMATION: gag stop
<221> NAME/KEY: gene
<222> LOCATION: (2501)..(4216)
<223> OTHER INFORMATION: pol RT
<221> NAME/KEY: gene
<222> LOCATION: (4217)..(5185)
<223> OTHER INFORMATION: pol IN
<221> NAME/KEY: misc_signal
<222> LOCATION: (5186)..(5188)
<223> OTHER INFORMATION: pol stop
<221> NAME/KEY: gene
<222> LOCATION: (5244)..(6263)
<223> OTHER INFORMATION: env gp85
<221> NAME/KEY: gene
<222> LOCATION: (6264)..(6878)
<223> OTHER INFORMATION: env gp37
<221> NAME/KEY: misc_signal
```

<222> LOCATION: (6879)..(6881)
<223> OTHER INFORMATION: env stop
<221> NAME/KEY: misc_feature
<222> LOCATION: (7027)
<223> OTHER INFORMATION: ClaI site/ the ClaI site in gag is methylated in Dam+ strains and does not cut

<400> SEQUENCE: 1

```
gccatttgac cattcaccac attggtgtgc acctggttg atggccggac cgttgattcc     60
ctgacgacta cgagcacctg catgaagcag aaggcttcat ttggtgaccc cgacgtgata    120
gttagggaat agtggtcggc cacagacggc gtggcgatcc tgtctccatc cgtctcgtct    180
atcgggaggc gagttcgatg accctggtgg aggggctgc ggcttaggga ggcagaagct     240
gagtaccgtc ggagggagct ccagggcccg gagcgactga cccctgccga gaactcagag    300
ggtcgtcgga agacggagag tgagcccgac gaccacccca ggcacgtctt tggtcggcct    360
gcggatcaag catggaagcc gtcattaagg tgatttcgtc cgcgtgtaaa acctattgcg    420
ggaaaatctc tccttctaag aaggaaatcg gggccatgtt gtccctgtta caaaaggaag    480
ggttgcttat gtctccctca gatttatatt ctccggggtc ctgggatccc atcactgcgg    540
cgctctccca gcgggcaatg gtacttggaa atcgggaga gttaaaaacc tggggattgg     600
ttttggggc attgaaggcg gctcgagagg aacaggttac atctgagcaa gcaaagtttt    660
ggttgggatt aggggaggg agggtctctc ccccaggtcc ggagtgcatc gagaaaccag     720
ctacggagcg gcgaatcgac aaaggggagg agtgggaga acaactgtg cagcgagatg      780
cgaagatggc gccagaggaa gcggccacac ctaaaaccgt tggcacatcc tgctatcatt    840
gcggaacagc tgttggctgc aattgcgcca ccgccacagc ctcggcccct cctcccctt     900
atgtggggag tggtttgtat ccttccctgg cggggtggg agagcagcag ggccagggag     960
ataacacgtc tcgggggcg gagcagccaa gggaggagcc agggcacgcg ggtcaggccc    1020
ctgggccggc cctgactgac tgggcaaggg taagggagga gcttgcgagt actggtccgc    1080
ccgtggtggc catgcctgta gtgattaaga cagagggacc cgcctggacc cctctggagc    1140
caaaattgat cacaagactg gctgatacgg tcaggaccaa gggcttacga tccccgatca    1200
ctatggcaga agtggaagcg ctcatgtcct ccccgttgct gccgcatgac gtcacgaatc    1260
taatgagagt gattttagga cctgccccat atgccttatg gatggacgct ggggagtcc    1320
aactccagac ggttatagcg gcagccactc gcgaccccg acacccagcg aacggtcaag    1380
ggcggggga acggactaac ttggatcgat taaagggctt agctgatggg atggtgggca    1440
acccacaggg tcaggccgca ttattaagac cggggaatt ggttgctatt acggcgtcgg    1500
ctctccaggc gttagagaa gttgcccggc tggcggaacc tgcaggtcca tgggcggaca   1560
tcacgcaggg accatctgag tcctttgttg attttgccaa tcggcttata aaggcggttg    1620
aggggtcaga tctcccgcct tccgcgcggg ctccggtgat cattgactgc tttaggcaga    1680
agtcacagcc agatattcag cagcttatac gggcagcacc ctccacgctg accaccccag    1740
gagagataat caaatatgtg ctagacaggc agaagattgc ccctcttacg gatcaaggca    1800
tagccgcggc catgtcgtct gctatccagc ccttagttat ggcagtagtc aatagagaga    1860
gggatggaca aactgggtcg ggtggtcgtg cccgagggct ctgctacact tgtggatccc    1920
cgggacatta tcaggcacag tgcccgaaaa acgaaagtc aggaaacagc cgtgagcgat     1980
gtcagctgtg tgacgggatg ggacacaacg ctaaacagtg taggaagcgg gatggcaacc    2040
agggccaacg cccaggaaga ggtctctctt cggggccgtg gccggccct gagcagcctg     2100
```

| | |
|---|---|
| ccgtctcgtt agcgatgaca atggaacata aagatcgccc cttggttagg gtcattctga | 2160 |
| ctaacactgg gagtcatcca gtcaaacaac gttcggtgta tatcaccgcg ctgttggact | 2220 |
| ccggagcgga catcactatt atttcgagga aggattggcc tactgattgg ccggtggtgg | 2280 |
| acaccgcgaa cccacagatc catggcatag gaggggggaat tcccatgcga aaatcccggg | 2340 |
| atatgataga ggtgggggtt attaaccgag acgggtcgtt ggagcgaccc ctgctcctct | 2400 |
| tccccgcagt cgctatggtt agagggagta tcctaggaag agattgtctg cagggcctag | 2460 |
| ggctccgctt gacaaattta tagggagggc cactgttctc actgttgcgc tacatctggc | 2520 |
| tattccgctc aaatggaagc cagaccgcac gcctgtgtgg attgaccagt ggcccctccc | 2580 |
| tgaaggtaaa cttgtaggcc taacgcaatt agtggaaaaa gaattacagt taggacatat | 2640 |
| agagccctca cttagttgtt ggaacacacc tgtttttcgt gatccggaag gcttccgggt | 2700 |
| cttatcgctt attgcatgat ttgcgcgctg ttaacgccaa gcttgtccct tttggggccg | 2760 |
| tccaacaggg ggcgccagtt ctctccgcgc tcccgcgtgg ctggcccctg atggtcctag | 2820 |
| acctcaagga ttgcttcttt tctatccctc ttgcggaaca agatcgcgaa gcttttgcat | 2880 |
| ttacgctccc ctctgtgaat aaccaggccc ccgctcgaag attccaatgg aaggtcttgc | 2940 |
| cccaagggat gacctgttct cccactatct gtcagttggt agtgggtcag gtgctcgagc | 3000 |
| ccttgcgact caagcaccca gctctgcgca tgttgcatta tatggacgat cttttgctag | 3060 |
| ccgcctcaag tcatgatggg ttggaagcgg cagggaagga ggttatcggt acattggaaa | 3120 |
| gagccggggtt cactatttcg ccggataaga tccagaggga gcccgagta caatatcttg | 3180 |
| ggtacaagtt aggcagtacg tatgtagcac ccgtaggctt ggtagcagaa cccaggatag | 3240 |
| ccaccttgtg ggatgttcaa aagctggtgg ggtcacttca gtggcttcgc ccagcgttag | 3300 |
| ggatcccgcc acgactgatg ggtcccttt atgagcagtt acgagggtca gatcctaacg | 3360 |
| aggcgaggga atgaatcta gacatgaaaa tggcctggag agagatcgta cagcttagca | 3420 |
| ctactgctgc cttggaacga tgggaccctg cccagcctct ggaaggagcg gtcgctagat | 3480 |
| gtgaacaggg ggcaataggg gtcctgggac agggactgtc cacacaccca aggccatgtt | 3540 |
| tgtggttatt ctccacccaa cccaccaagg cgtttactgc ttggttagaa gtgctcaccc | 3600 |
| ttttgattac taagctacgc gcttcggcag tgcgaacctt tggcaaggag gttgatatcc | 3660 |
| tcctgttgcc tgcatgcttc cgggaggacc ttccgctccc ggagggggatc ctgttagcac | 3720 |
| ttaggggggtt tgcaggaaaa atcaggagta gtgacacgcc atctattttt gacattgcgc | 3780 |
| gtccactgca tgtttctctg aaagtgaggg ttaccgacca ccctgtgccg ggacccactg | 3840 |
| tctttaccga cgcctcctca agcacccata aagggtggt agtctggagg gagggcccaa | 3900 |
| ggtgggagat aaaagaaata gttgatttgg gggcaagtgt acaacaactg gaggcacgcg | 3960 |
| ctgtggccat ggcacttctg ctgtggccga caacgcccac taatgtagtg actgactctg | 4020 |
| cgtttgttgc gaaaatgtta tcaagatgg gacaggaggg agtccgtct acagcggcgg | 4080 |
| cttttatttt agaggatgcg ttaagccaaa ggtcagccat ggccgccgtt ctccacgtgc | 4140 |
| ggagtcattc tgaagtgcca gggttttttca cagaaggaaa tgacgtggca gatagccaag | 4200 |
| ccaccttttca agcgtatccc ttgagagagg ctaaagatct tcataccgct ctccatattg | 4260 |
| gaccccgcgc gctatccaaa gcgtgtaata tatctatgca gcaggctagg gaggttgttc | 4320 |
| agacctgccc gcattgtaat tcagcccctg cgttggaggc cggggtaaac cctagggggtt | 4380 |
| tgggacccct acagatatgg cagacagact ttacgcttga gcctagaatg gctccccgtt | 4440 |
| cctggctcgc tgttactgtg gacaccgcct catcagcgat agtcgtaact cagcatggcc | 4500 |

```
gtgttacatc ggttgctgca caacatcatt gggccacggc tatcgccgtt ttgggaagac    4560
caaaggccat aaaaacagat aacgggtcct gcttcacgtc cagatccacg cgagagtggc    4620
tcgcgagatg ggggatagca cacaccaccg ggattccggg aaattcccag ggtcaagcta    4680
tggtagagcg ggccaaccgg ctcctgaaag ataagatccg tgtgctcgcg gagggggacg    4740
gctttatgaa aagaatcccc accagcaaac agggggaact attagccaag gcaatgtatg    4800
ccctcaatca ctttgagcgt ggtgaaaaca caaaaacacc gatacaaaaa cactggagac    4860
ctaccgttct tacagaagga cccccggtta aatacgaat  agagacaggg gagtgggaaa    4920
aaggatggaa cgtgctggtc tggggacgag gttatgccgc tgtgaaaaac agggacactg    4980
ataaggttat ttgggtaccc tctcggaaag ttaaaccgga tgtcacccaa aaggatgagg    5040
tgactaagaa agatgaggcg agccctcttt tgcaggcat  ttctgactgg ataccctggg    5100
aagacgagca agaaggactc caaggagaaa ccgctagcaa caagcaagaa agacccggag    5160
aagacaccct tgctgccaac gagagttaat tatattctca ttattggtgt cctggtcttg    5220
tgtgaggtta cggggtaag  agctgatgtc cacttactcg agcagccagg gaacctttgg    5280
attacatggg ccaaccgtac aggccaaacg gattttgcc  tctctacaca gtcagccacc    5340 tcccctttc aaacatgttt gataggtatc ccgtcccta  tttccgaggg tgattttaag    5400
ggatatgttt ctgatacaaa ttgcaccacc ttgggaactg atcggttagt ctcgtcagcc    5460
gactttactg gcggacctga caacagtacc accctcactt atcggaaggt ctcatgcttg    5520
ttgttaaagc tgaatgtctc tatgtgggat gagccacctg aactacagct gttaggttcc    5580
cagtctctcc ctaacattac taatattgct cagatttccg gtataaccgg gggatgcgta    5640
ggcttcagac cacaagggt tccttggtat ctaggttggt ctagacagga ggccacgcgg     5700
tttctcctta gacaccctc tttctctaaa tccacggaac cgtttacagt ggtgacagcg    5760
gataggcaca atctttttat ggggagtgag tactgcggtg catatggcta cagattttgg    5820
aacatgtata actgctcaca ggtggggcgg cagtaccgct gtggtaatgc gcgcacgccc    5880
cgcacgggtc ttcctgaaat ccagtgtaca aggagaggag gcaaatgggt taatcaatca    5940
caggaaatta atgagtcgga gccgttcagc tttacggtga actgtacagc tagtagtttg    6000
ggtaatgcca gtgggtgttg cggaaaagca ggcacgattc tcccgggaaa gtgggtcgac    6060
agcacacaag gtagtttcac caaaccaaaa gcgctaccac ccgcaatttt cctcatttgt    6120
ggggatcgcg catggcaagg aattcccagt cgtccggtag ggggcccctg ctatttaggc    6180
aagcttacca tgttagcacc taagcataca gatattctca aggtgcttgt caattcatcg    6240
cggacaggta taagacgtaa acgaagcacc tcacacctgg atgatacatg ctcagatgaa    6300
gtgcagcttt ggggtcctac agcaagaatc tttgcatcta tcctagcccc gggggtagca    6360
gctgcgcaag cctaagagaa aattgagaga ctagcctgtt ggtccgttaa acaggctaac    6420
ttgacaacat cactcctcgg ggacttattg gatgatgtca cgagtattcg acacgcggtc    6480
ctgcagaacc gagcggctat tgacttcttg ctcctagctc acggcatggc tgtgaggac     6540 gttgccggaa tgtgctgttt caatttgagt gatcagagtg agtctataca gaagaagttc    6600
cagctaatga aggaacatgt caataagatc ggcgtggata gcgacctaat tggaagttgg    6660
ctgcgaggac tattcggggg aataggagaa tgggccgttc atttgctgaa aggactgctt    6720
ttggggcttg tagttatttt gttgctagta gtgtgcctgc cttgccttt  gcaaatgtta    6780 tgcggtaata ggagaaagat gattaataac tccatcagct accacacgga atataagaag    6840
```

-continued

```
ctgcaaaagg cctgtgggca gcctgaaagc agaatagtat aaggcagtac atgggtggtg      6900
gtatagcgct tgcgagtcca tcgagcaagg caggaaagac agctattggt aattgtgaaa      6960
tacgcttttg tctgtgtgct gcaggagctg agctgactct gctggtggcc tcgcgtacca      7020
ctgtggcatc gatgcgatgt acgggccaga tatacgcgta tctgagggga ctagggtgtg      7080
tttaggcgaa aagcgggct tcggttgtac gcggttagga gtccccttag gatatagtag       7140
tttcgctttt gcatagggag ggggaaatgt agtcttatgc aatactcttg tagtcttgca      7200
acatggtaac gatgagttag caacatgcct tacaaggaga gaaaaagcac cgtgcatgcc      7260
gattggtgga agtaaggtgg tacgatcgtg ccttattagg aaggcaacag acgggtctga      7320
catggattgg acgaaccact gaattccgca ttgcagagat attgtattta agtgcctagc      7380
tcgatacaat aaacgccatt tgaccattca ccacattggt gtgcacctgg gttgatggcc      7440
ggaccgttga ttccctgacg actacgagca cctgcatgaa gcagaaggct tcatttggtg      7500
accccgacgt gatagttagg gaatagtggt cggccacaga cggcgtggcg atcctgtctc      7560
catccgtctc gtctatcggg aggcgacttc gatgaccctg gtggaggggg ctgcggctta      7620
gggaggcaga agctgagtac cgtcggaggg gatccacagg acgggtgtgg tcgccatgat      7680
cgcgtagtcg atagtggctc caagtagcga agcgagcagg actgggcggc ggccaaagcg      7740
gtcggacagt gctccgagaa cgggtgcgca tagaaattgc atcaacgcat atagcgctag      7800
cagcacgcca tagtgactgg cgatgctgtc ggaatggacg atatcccgca agaggcccgg      7860
cagtaccggc ataaccaagc ctatgcctac agcatccagg gtgacggtgc cgaggatgac      7920
gatgagcgca ttgttagatt tcatacacgg tgcctgactg cgttagcaat ttaactgtga      7980
taaactaccg cattaaagct ccaaacttgg ctgtttcctg tgtgaaattg ttatccgctc      8040
acaattccac acattatacg agccggaagc ataaagtgta aaacctgggg tgcctaatga      8100
gtgagaattc ttgaagacga aagggcctcg tgatacgcct attttatag gttaatgtca       8160 tgataataat ggtttcttag acgtcaggtg gcacttttcg gggaaatgtg cgcggaaccc      8220
ctatttgttt attttctaa atacattcaa atatgtatcc gctcatgaga caataaccct       8280
gataaatgct tcaataatat tgaaaaagga agagtatgag tattcaacat ttccgtgtcg      8340
cccttattcc ctttttgcg gcattttgcc ttcctgtttt tgctcaccca gaaacgctgg       8400
tgaaagtaaa agatgctgaa gatcagttgg gtgcacgagt gggttacatc gaactggatc      8460
tcaacagcgg taagatcctt gagagttttc gccccgaaga acgttttcca atgatgagca      8520
cttttaaagt tctgctatgt ggcgcggtat tatcccgtgt tgacgccggg caagagcaac      8580
tcggtcgccg catacactat tctcagaatg acttggttga gtactcacca gtcacagaaa      8640
agcatcttac ggatggcatg acagtaagag aattatgcag tgctgccata accatgagtg      8700
ataacactgc ggccaactta cttctgacaa cgatcgagg accgaaggag ctaaccgctt       8760
ttttgcacaa catgggggat catgtaactc gccttgatcg ttgggaaccg gagctgaatg      8820
aagccatacc aaacgacgag cgtgacacca cgatgcctgc agcaatggca acaacgttgc      8880
gcaaactatt aactggcgaa ctacttactc tagcttcccg gcaacaatta atagactgga      8940
tggaggcgga taaagttgca ggaccacttc tgcgctcggc ccttccggct ggctggttta      9000
ttgctgataa atctggagcc ggtgagcgtg gtctcgcgg tatcattgca gcactggggc       9060
cagatggtaa gccctcccgt atcgtagtta tctacacgac ggggagtcag gcaactatgg      9120
atgaacgaaa tagacagatc gctgagatag gtgcctcact gattaagcat tggtaactgt      9180
cagaccaagt ttactcatat atactttaga ttgatttaaa acttcatttt taatttaaaa      9240
```

```
ggatctaggt gaagatcctt tttgataatc tcatgaccaa atcccttaa cgtgagtttt    9300 cgttccactg agcgtcagac cccgtagaaa agatcaaagg atcttcttga gatccttttt    9360
ttctgcgcgt aatctgctgc ttgcaaacaa aaaaccacc gctaccagcg gtggtttgtt    9420
tgccggatca agagctacca actcttttc cgaaggtaac tggcttcagc agagcgcaga    9480
taccaaatac tgtccttcta gtgtagccgt agttaggcca ccacttcaag aactctgtag    9540
caccgcctac atacctcgct ctgctaatcc tgttaccagt ggctgctgcc agtggcgata    9600
agtcgtgtct taccgggttg gactcaagac gatagttacc ggataaggcg cagcggtcgg    9660
gctgaacggg gggttcgtgc acacagccca gcttggagcg aacgacctac accgaactga    9720
gatacctaca gcgtgagcta tgagaaagcg ccacgcttcc gaagggaga aaggcggaca    9780 ggtatccggt aagcggcagg gtcggaacag gagagcgcac gagggagctt ccaggggaa    9840 acgcctggta tctttatagt cctgtcgggt ttcgccacct ctgacttgag cgtcgatttt    9900
tgtgatgctc gtcagggggg cggagcctat ggaaaaacgc cagcaacgcg gccttttac     9960 ggttcctggc cttttgctgg ccttttgctc acatgttctt tcctgcgtta tccctgatt    10020 ctgtggataa ccgtattacc gcctttgagt gagctgatac cgctcgccgc agccgaacga    10080
ccgagcgcag cgagtcagtg agcgaggaag cggaagagcg cctgatgcgg tattttctcc    10140
ttacgcatct gtgcggtatt tcacaccgca tatggtgcac tctcagtaca atctgctctg    10200
atgccgcata gttaagccag tatacactcc gctatcgcta cgtgactggg tcatggctgc    10260
gccccgacac ccgccaacac ccgctgacgc gccctgacgg gcttgtctgc tcccggcatc    10320
cgcttacaga caagctgtga ccgtctccgg gagctgcatg tgtcagaggt tttcaccgtc    10380
atcaccgaaa cgcgcgaggc agctgcggta aagctcatca gcgtggtcgt gaagcgattc    10440
acagatgtct gcctgttcat ccgcgtccag ctcgttgagt ttctccagaa gcgttaatgt    10500
ctggcttctg ataaagcggg ccatgttaag ggcggttttt tcctgtttgg tcacttgatg    10560
cctccgtgta aggggaatt tctgttcatg gggtaatga taccgatgaa acgagagagg    10620
atgctcacga tacgggttac tgatgatgaa catgcccggt tactggaacg ttgtgagggt    10680
aaacaactgg cggtatggat gcggcgggac cagagaaaaa tcactcaggg tcaatgccag    10740
cgcttcgtta atacagatgt aggtgttcca cagggtagcc agcagcatcc tgcgatgcag    10800
atccggaaca taatggtgca gggcgctgac ttccgcgttt ccagacttta cgaaacacgg    10860
aaaccgaaga ccattcatgt tgttgctcag gtcgcagacg ttttgcagca gcagtcgctt    10920
cacgttcgct cgcgtatcgg tgattcattc tgctaaccag taaggcaacc ccgccagcct    10980
agccgggtcc tcaacgacag gagcacgatc atgagcaccc gtggccagga cccaacgctg    11040
cccgagatgc gccgcgtgcg gctgctggag atggcggacg cgatggatat gttctgccaa    11100
gggttggttt gcgcattcac agttctccgc aagaattgat tggctccaat tcttggagtg    11160
gtgaatccgt tagcgaggtg ccgccggctt ccattcaggt cgaggtggcc cggctccatg    11220
caccgcgacg caacgcgggg aggcagacaa ggtatagggc ggcgatgcga tgtacgggcc    11280
agatatacgc gtatctgagg ggactagggt gtgtttaggc gaaaagcggg gcttcggttg    11340
tacgcggtta ggagtcccct taggatatag tagtttcgct tttgcatagg gagggggaaa    11400
tgtagtctta tgcaatactc ttgtagtctt gcaacatggt aacgatgagt tagcaacatg    11460
ccttacaagg agagaaaaag caccgtgcat gccgattggt ggaagtaagg tggtacgatc    11520
gtgccttatt aggaaggcaa cagacgggtc tgacatggat tggacgaacc actgaattcc    11580
```

```
gcattgcaga gatattgtat ttaagtgcct agctcgatac aataaac                    11627

<210> SEQ ID NO 2
<211> LENGTH: 1759
<212> TYPE: DNA
<213> ORGANISM: Chicken
<220> FEATURE:
<221> NAME/KEY: gene
<222> LOCATION: (1)..(1759)
<223> OTHER INFORMATION: chicken c-SRC cDNA
<221> NAME/KEY: CDS
<222> LOCATION: (112)..(1710)

<400> SEQUENCE: 2
tctgacaccc atctgtctgt ctgtctgtgt gctgcaggag ctgagctgac tctgctgtgg        60
cctcgcgtac cactgtggcc aggcggtagc tgggacgtgc agcccaccac c atg ggg      117
                                                        Met Gly
                                                          1 agc agc aag agc aag ccc aag gac ccc agc cag cgc cgg cgc agc ctg        165
Ser Ser Lys Ser Lys Pro Lys Asp Pro Ser Gln Arg Arg Arg Ser Leu
          5                  10                  15 gag cca ccc gac agc acc cac cac ggg gga ttc cca gcc tcg cag acc        213
Glu Pro Pro Asp Ser Thr His His Gly Gly Phe Pro Ala Ser Gln Thr
 20                  25                  30 ccc aac aag aca gca gcc ccc gac acg cac cgc acc ccc agc cgc tcc        261
Pro Asn Lys Thr Ala Ala Pro Asp Thr His Arg Thr Pro Ser Arg Ser
 35                  40                  45                  50 ttt ggg acc gtg gcc acc gag ccc aag ctc ttc ggg ggc ttc aac act        309
Phe Gly Thr Val Ala Thr Glu Pro Lys Leu Phe Gly Gly Phe Asn Thr
                 55                  60                  65 tct gac acc gtt acg tcg ccg cag cgt gcc ggg gca ctg gct ggc ggc        357
Ser Asp Thr Val Thr Ser Pro Gln Arg Ala Gly Ala Leu Ala Gly Gly
         70                  75                  80 gtc acc act ttc gtg gct ctc tac gac tac gag tcc cgg act gaa acg        405
Val Thr Thr Phe Val Ala Leu Tyr Asp Tyr Glu Ser Arg Thr Glu Thr
             85                  90                  95 gac ttg tcc ttc aag aaa gga gaa cgc ctg cag att gtc aac aac acg        453
Asp Leu Ser Phe Lys Lys Gly Glu Arg Leu Gln Ile Val Asn Asn Thr
        100                 105                 110 gaa ggt gac tgg tgg ctg gct cat tcc ctc act aca gga cag acg ggc        501
Glu Gly Asp Trp Trp Leu Ala His Ser Leu Thr Thr Gly Gln Thr Gly
115                 120                 125                 130 tac atc ccc agt aac tat gtc gcg ccc tca gac tcc atc cag gct gaa        549
Tyr Ile Pro Ser Asn Tyr Val Ala Pro Ser Asp Ser Ile Gln Ala Glu
                135                 140                 145 gag tgg tac ttt ggg aag atc act cgt cgg gag tcc gag cgg ctg ctg        597
Glu Trp Tyr Phe Gly Lys Ile Thr Arg Arg Glu Ser Glu Arg Leu Leu
            150                 155                 160 ctc aac ccc gaa aac ccc cgg gga acc ttc ttg gtc cgg gag agc gag        645
Leu Asn Pro Glu Asn Pro Arg Gly Thr Phe Leu Val Arg Glu Ser Glu
        165                 170                 175 acg aca aaa ggt gcc tat tgc ctc tcc gtt tct gac ttt gac aac gcc        693
Thr Thr Lys Gly Ala Tyr Cys Leu Ser Val Ser Asp Phe Asp Asn Ala
    180                 185                 190 aag ggg ctc aat gtg aag cac tac aag atc cgc aag ctg gac agc ggc        741
Lys Gly Leu Asn Val Lys His Tyr Lys Ile Arg Lys Leu Asp Ser Gly
195                 200                 205                 210 ggc ttc tac atc acc tca cgc aca cag ttc agc agc ctg cag cag ctg        789
Gly Phe Tyr Ile Thr Ser Arg Thr Gln Phe Ser Ser Leu Gln Gln Leu
                215                 220                 225 gtg gcc tac tac tcc aaa cat gct gat ggc ttg tgc cac cgc ctg acc        837
```

-continued

```
                Val Ala Tyr Tyr Ser Lys His Ala Asp Gly Leu Cys His Arg Leu Thr
                                230                 235                 240 aac gtc tgc ccc acg tcc aag ccc cag acc cag gga ctc gcc aag gac            885
Asn Val Cys Pro Thr Ser Lys Pro Gln Thr Gln Gly Leu Ala Lys Asp
            245                 250                 255 gcg tgg gaa atc ccc cgg gag tcg ctg cgg ctg gag gtg aag ctg ggg            933
Ala Trp Glu Ile Pro Arg Glu Ser Leu Arg Leu Glu Val Lys Leu Gly
260                 265                 270 cag ggc tgc ttt gga gag gtc tgg atg ggg acc tgg aac ggc acc acc            981
Gln Gly Cys Phe Gly Glu Val Trp Met Gly Thr Trp Asn Gly Thr Thr
275                 280                 285                 290 aga gtg gcc ata aag act ctg aag ccc ggc acc atg tcc ccg gag gcc           1029
Arg Val Ala Ile Lys Thr Leu Lys Pro Gly Thr Met Ser Pro Glu Ala
                295                 300                 305 ttc ctg cag gaa gcc caa gtg atg aag aag ctc cgg cat gag aag ctg           1077
Phe Leu Gln Glu Ala Gln Val Met Lys Lys Leu Arg His Glu Lys Leu
            310                 315                 320 gtt cag ctg tac gca gtg gtg tcg gaa gag ccc atc tac atc gtc act           1125
Val Gln Leu Tyr Ala Val Val Ser Glu Glu Pro Ile Tyr Ile Val Thr
            325                 330                 335 gag tac atg agc aag ggg agc ctc ctg gat ttc ctg aag gga gag atg           1173
Glu Tyr Met Ser Lys Gly Ser Leu Leu Asp Phe Leu Lys Gly Glu Met
340                 345                 350 ggc aag tac ctg cgg ctg cca cag ctc gtc gat atg gct gct cag att           1221
Gly Lys Tyr Leu Arg Leu Pro Gln Leu Val Asp Met Ala Ala Gln Ile
355                 360                 365                 370 gca tcc ggc atg gcc tat gtg gag agg atg aac tac gtg cac cga gac           1269
Ala Ser Gly Met Ala Tyr Val Glu Arg Met Asn Tyr Val His Arg Asp
                375                 380                 385 ctg cgg gcg gcc aac atc ctg gtg ggg gag aac ctg gtg tgc aag gtg           1317
Leu Arg Ala Ala Asn Ile Leu Val Gly Glu Asn Leu Val Cys Lys Val
            390                 395                 400 gct gac ttt ggg ctg gca cgc ctc atc gag gac aac gag tac aca gca           1365
Ala Asp Phe Gly Leu Ala Arg Leu Ile Glu Asp Asn Glu Tyr Thr Ala
            405                 410                 415 cgg caa ggt gcc aag ttc ccc atc aag tgg aca gcc ccc gag gca gcc           1413
Arg Gln Gly Ala Lys Phe Pro Ile Lys Trp Thr Ala Pro Glu Ala Ala
420                 425                 430 ctc tat ggc cgg ttc acc atc aag tcg gat gtc tgg tcc ttc ggc atc           1461
Leu Tyr Gly Arg Phe Thr Ile Lys Ser Asp Val Trp Ser Phe Gly Ile
435                 440                 445                 450 ctg ctg act gag ctg acc acc aag ggc cgg gtg cca tac cca ggg atg           1509
Leu Leu Thr Glu Leu Thr Thr Lys Gly Arg Val Pro Tyr Pro Gly Met
                455                 460                 465 gtc aac agg gag gtg ctg gac cag gtg gag agg ggc tac cgc atg ccc           1557
Val Asn Arg Glu Val Leu Asp Gln Val Glu Arg Gly Tyr Arg Met Pro
            470                 475                 480 tgc ccg ccc gag tgc ccc gag tcg ctg cat gac ctc atg tgc cag tgc           1605
Cys Pro Pro Glu Cys Pro Glu Ser Leu His Asp Leu Met Cys Gln Cys
            485                 490                 495 tgg cgg agg gac cct gag gag cgg ccc act ttt gag tac ctg cag gcc           1653
Trp Arg Arg Asp Pro Glu Glu Arg Pro Thr Phe Glu Tyr Leu Gln Ala
500                 505                 510 ttc ctg gag gac tac ttc acc tcg aca gag ccc cag tac cag cct gga           1701
Phe Leu Glu Asp Tyr Phe Thr Ser Thr Glu Pro Gln Tyr Gln Pro Gly
515                 520                 525                 530 gag aac cta taggcctgga gctcctcctg gaccagaggc ctcgctgtgg ggtacaggg         1759
Glu Asn Leu
```

-continued

```
<210> SEQ ID NO 3
<211> LENGTH: 533
<212> TYPE:   PRT
<213> ORGANISM: Chicken

<400> SEQUENCE: 3
```

| | | | | | | | | | | | | | | | |
|---|---|---|---|---|---|---|---|---|---|---|---|---|---|---|---|
| Met | Gly | Ser | Ser | Lys | Ser | Lys | Pro | Lys | Asp | Pro | Ser | Gln | Arg | Arg | Arg |
| 1 | | | | 5 | | | | | 10 | | | | | 15 | |
| Ser | Leu | Glu | Pro | Pro | Asp | Ser | Thr | His | His | Gly | Gly | Phe | Pro | Ala | Ser |
| | | | | 20 | | | | | 25 | | | | | 30 | |
| Gln | Thr | Pro | Asn | Lys | Thr | Ala | Ala | Pro | Asp | Thr | His | Arg | Thr | Pro | Ser |
| | | | | 35 | | | | | 40 | | | | | 45 | |
| Arg | Ser | Phe | Gly | Thr | Val | Ala | Thr | Glu | Pro | Lys | Leu | Phe | Gly | Gly | Phe |
| | 50 | | | | | 55 | | | | | 60 | | | | |
| Asn | Thr | Ser | Asp | Thr | Val | Thr | Ser | Pro | Gln | Arg | Ala | Gly | Ala | Leu | Ala |
| 65 | | | | | 70 | | | | | 75 | | | | | 80 |
| Gly | Gly | Val | Thr | Thr | Phe | Val | Ala | Leu | Tyr | Asp | Tyr | Glu | Ser | Arg | Thr |
| | | | | 85 | | | | | 90 | | | | | 95 | |
| Glu | Thr | Asp | Leu | Ser | Phe | Lys | Lys | Gly | Glu | Arg | Leu | Gln | Ile | Val | Asn |
| | | | | 100 | | | | | 105 | | | | | 110 | |
| Asn | Thr | Glu | Gly | Asp | Trp | Trp | Leu | Ala | His | Ser | Leu | Thr | Thr | Gly | Gln |
| | | | | 115 | | | | | 120 | | | | | 125 | |
| Thr | Gly | Tyr | Ile | Pro | Ser | Asn | Tyr | Val | Ala | Pro | Ser | Asp | Ser | Ile | Gln |
| | 130 | | | | | 135 | | | | | 140 | | | | |
| Ala | Glu | Glu | Trp | Tyr | Phe | Gly | Lys | Ile | Thr | Arg | Arg | Glu | Ser | Glu | Arg |
| 145 | | | | | 150 | | | | | 155 | | | | | 160 |
| Leu | Leu | Leu | Asn | Pro | Glu | Asn | Pro | Arg | Gly | Thr | Phe | Leu | Val | Arg | Glu |
| | | | | 165 | | | | | 170 | | | | | 175 | |
| Ser | Glu | Thr | Thr | Lys | Gly | Ala | Tyr | Cys | Leu | Ser | Val | Ser | Asp | Phe | Asp |
| | | | | 180 | | | | | 185 | | | | | 190 | |
| Asn | Ala | Lys | Gly | Leu | Asn | Val | Lys | His | Tyr | Lys | Ile | Arg | Lys | Leu | Asp |
| | | | | 195 | | | | | 200 | | | | | 205 | |
| Ser | Gly | Gly | Phe | Tyr | Ile | Thr | Ser | Arg | Thr | Gln | Phe | Ser | Ser | Leu | Gln |
| | 210 | | | | | 215 | | | | | 220 | | | | |
| Gln | Leu | Val | Ala | Tyr | Tyr | Ser | Lys | His | Ala | Asp | Gly | Leu | Cys | His | Arg |
| 225 | | | | | 230 | | | | | 235 | | | | | 240 |
| Leu | Thr | Asn | Val | Cys | Pro | Thr | Ser | Lys | Pro | Gln | Thr | Gln | Gly | Leu | Ala |
| | | | | 245 | | | | | 250 | | | | | 255 | |
| Lys | Asp | Ala | Trp | Glu | Ile | Pro | Arg | Glu | Ser | Leu | Arg | Leu | Glu | Val | Lys |
| | | | | 260 | | | | | 265 | | | | | 270 | |
| Leu | Gly | Gln | Gly | Cys | Phe | Gly | Glu | Val | Trp | Met | Gly | Thr | Trp | Asn | Gly |
| | | | | 275 | | | | | 280 | | | | | 285 | |
| Thr | Thr | Arg | Val | Ala | Ile | Lys | Thr | Leu | Lys | Pro | Gly | Thr | Met | Ser | Pro |
| | 290 | | | | | 295 | | | | | 300 | | | | |
| Glu | Ala | Phe | Leu | Gln | Glu | Ala | Gln | Val | Met | Lys | Lys | Leu | Arg | His | Glu |
| 305 | | | | | 310 | | | | | 315 | | | | | 320 |
| Lys | Leu | Val | Gln | Leu | Tyr | Ala | Val | Val | Ser | Glu | Glu | Pro | Ile | Tyr | Ile |
| | | | | 325 | | | | | 330 | | | | | 335 | |
| Val | Thr | Glu | Tyr | Met | Ser | Lys | Gly | Ser | Leu | Leu | Asp | Phe | Leu | Lys | Gly |
| | | | | 340 | | | | | 345 | | | | | 350 | |
| Glu | Met | Gly | Lys | Tyr | Leu | Arg | Leu | Pro | Gln | Leu | Val | Asp | Met | Ala | Ala |
| | | | | 355 | | | | | 360 | | | | | 365 | |
| Gln | Ile | Ala | Ser | Gly | Met | Ala | Tyr | Val | Glu | Arg | Met | Asn | Tyr | Val | His |
| | 370 | | | | | 375 | | | | | 380 | | | | |

-continued

```
Arg Asp Leu Arg Ala Ala Asn Ile Leu Val Gly Glu Asn Leu Val Cys
385                 390                 395                 400

Lys Val Ala Asp Phe Gly Leu Ala Arg Leu Ile Glu Asp Asn Glu Tyr
                405                 410                 415

Thr Ala Arg Gln Gly Ala Lys Phe Pro Ile Lys Trp Thr Ala Pro Glu
            420                 425                 430

Ala Ala Leu Tyr Gly Arg Phe Thr Ile Lys Ser Asp Val Trp Ser Phe
        435                 440                 445

Gly Ile Leu Leu Thr Glu Leu Thr Thr Lys Gly Arg Val Pro Tyr Pro
    450                 455                 460

Gly Met Val Asn Arg Glu Val Leu Asp Gln Val Glu Arg Gly Tyr Arg
465                 470                 475                 480

Met Pro Cys Pro Pro Glu Cys Pro Glu Ser Leu His Asp Leu Met Cys
                485                 490                 495

Gln Cys Trp Arg Arg Asp Pro Glu Glu Arg Pro Thr Phe Glu Tyr Leu
            500                 505                 510

Gln Ala Phe Leu Glu Asp Tyr Phe Thr Ser Thr Glu Pro Gln Tyr Gln
        515                 520                 525

Pro Gly Glu Asn Leu
    530
```

```
<210> SEQ ID NO 4
<211> LENGTH: 2187
<212> TYPE: DNA
<213> ORGANISM: Homo sapiens
<220> FEATURE:
<221> NAME/KEY: gene
<222> LOCATION: (1)..(2187)
<223> OTHER INFORMATION: human c-SRC cDNA
<221> NAME/KEY: CDS
<222> LOCATION: (134)..(1483)

<400> SEQUENCE: 4
```

```
gcgccgcgtc ccgcaggccg tgatgccgcc cgcgcggagg tggcccggac cgcagtgccc      60
caagagagct ctaatggtac caagtgacag gttggcttta ctgtgactcg ggacgccag     120 agctcctgag aag atg tca gca ata cag gcc gcc tgg cca tcc ggt aca       169
            Met Ser Ala Ile Gln Ala Ala Trp Pro Ser Gly Thr
              1               5                   10 gaa tgt att gcc aag tac aac ttc cac ggc act gcc gag cag gac ctg      217
Glu Cys Ile Ala Lys Tyr Asn Phe His Gly Thr Ala Glu Gln Asp Leu
        15                  20                  25 ccc ttc tgc aaa gga gac gtg ctc acc att gtg gcc gtc acc aag gac      265
Pro Phe Cys Lys Gly Asp Val Leu Thr Ile Val Ala Val Thr Lys Asp
    30                  35                  40 ccc aac tgg tac aaa gcc aaa aac aag gtg ggc cgt gag ggc atc atc      313
Pro Asn Trp Tyr Lys Ala Lys Asn Lys Val Gly Arg Glu Gly Ile Ile
45                  50                  55                  60 cca gcc aac tac gtc cag aag cgg gag ggc gtg aag gcg ggt acc aaa      361
Pro Ala Asn Tyr Val Gln Lys Arg Glu Gly Val Lys Ala Gly Thr Lys
                65                  70                  75 ctc agc ctc atg cct tgg ttc cac ggc aag atc aca cgg gag cag gct      409
Leu Ser Leu Met Pro Trp Phe His Gly Lys Ile Thr Arg Glu Gln Ala
            80                  85                  90 gag cgg ctt ctg tac ccg ccg gag aca ggc ctg ttc ctg gtg cgg gag      457
Glu Arg Leu Leu Tyr Pro Pro Glu Thr Gly Leu Phe Leu Val Arg Glu
        95                  100                 105 agc acc aac tac ccc gga gac tac acg ctg tgc gtg agc tgc gac ggc      505
Ser Thr Asn Tyr Pro Gly Asp Tyr Thr Leu Cys Val Ser Cys Asp Gly
    110                 115                 120
```

| | |
|---|---|
| aag gtg gag cac tac cgc atc atg tac cat gcc agc aag ctc agc atc<br>Lys Val Glu His Tyr Arg Ile Met Tyr His Ala Ser Lys Leu Ser Ile<br>125                       130                    135                 140 | 553 |
| gac gag gag gtg tac ttt gag aac ctc atg cag ctg gtg gag cac tac<br>Asp Glu Glu Val Tyr Phe Glu Asn Leu Met Gln Leu Val Glu His Tyr<br>                 145                    150                    155 | 601 |
| acc tca gac gca gat gga ctc tgt acg cgc ctc att aaa cca aag gtc<br>Thr Ser Asp Ala Asp Gly Leu Cys Thr Arg Leu Ile Lys Pro Lys Val<br>                160                    165                  170 | 649 |
| atg gag ggc aca gtg gcg gcc cag gat gag ttc tac cgc agc ggc tgg<br>Met Glu Gly Thr Val Ala Ala Gln Asp Glu Phe Tyr Arg Ser Gly Trp<br>175                       180                    185 | 697 |
| gcc ctg aac atg aag gag ctg aag ctg ctg cag acc atc ggg aag ggg<br>Ala Leu Asn Met Lys Glu Leu Lys Leu Leu Gln Thr Ile Gly Lys Gly<br>         190                    195                    200 | 745 |
| gag ttc gga gac gtg atg ctg ggc gat tac cga ggg aac aaa gtc gcc<br>Glu Phe Gly Asp Val Met Leu Gly Asp Tyr Arg Gly Asn Lys Val Ala<br>205                       210                    215                220 | 793 |
| gtc aag tgc att aag aac gac gcc act gcc cag gcc ttc ctg gct gaa<br>Val Lys Cys Ile Lys Asn Asp Ala Thr Ala Gln Ala Phe Leu Ala Glu<br>                 225                    230                  235 | 841 |
| gcc tca gtc atg acg caa ctg cgg cat agc aac ctg gtg cag ctc ctg<br>Ala Ser Val Met Thr Gln Leu Arg His Ser Asn Leu Val Gln Leu Leu<br>                240                    245                  250 | 889 |
| ggc gtg atc gtg gag gag aag ggc ggg ctc tac atc gtc act gag tac<br>Gly Val Ile Val Glu Glu Lys Gly Gly Leu Tyr Ile Val Thr Glu Tyr<br>                 255                    260                  265 | 937 |
| atg gcc aag ggg agc ctt gtg gac tac ctg cgg tct agg ggt cgg tca<br>Met Ala Lys Gly Ser Leu Val Asp Tyr Leu Arg Ser Arg Gly Arg Ser<br>270                       275                    280 | 985 |
| gtg ctg ggc gga gac tgt ctc ctc aag ttc tcg cta gat gtc tgc gag<br>Val Leu Gly Gly Asp Cys Leu Leu Lys Phe Ser Leu Asp Val Cys Glu<br>285                       290                    295                300 | 1033 |
| gcc atg gaa tac ctg gag ggc aac aat ttc gtg cat cga gac ctg gct<br>Ala Met Glu Tyr Leu Glu Gly Asn Asn Phe Val His Arg Asp Leu Ala<br>                 305                    310                  315 | 1081 |
| gcc cgc aat gtg ctg gtg tct gag gac aac gtg gcc aag gtc agc gac<br>Ala Arg Asn Val Leu Val Ser Glu Asp Asn Val Ala Lys Val Ser Asp<br>                320                    325                  330 | 1129 |
| ttt ggt ctc acc aag gag gcg tcc agc acc cag gac acg ggc aag ctg<br>Phe Gly Leu Thr Lys Glu Ala Ser Ser Thr Gln Asp Thr Gly Lys Leu<br>                 335                    340                  345 | 1177 |
| cca gtc aag tgg aca gcc cct gag gcc ctg aga gag aag aaa ttc tcc<br>Pro Val Lys Trp Thr Ala Pro Glu Ala Leu Arg Glu Lys Lys Phe Ser<br>350                       355                    360 | 1225 |
| act aag tct gac gtg tgg agt ttc gga atc ctt ctc tgg gaa atc tac<br>Thr Lys Ser Asp Val Trp Ser Phe Gly Ile Leu Leu Trp Glu Ile Tyr<br>365                       370                    375                380 | 1273 |
| tcc ttt ggg cga gtg cct tat cca aga att ccc ctg aag gac gtc gtc<br>Ser Phe Gly Arg Val Pro Tyr Pro Arg Ile Pro Leu Lys Asp Val Val<br>                385                    390                  395 | 1321 |
| cct cgg gtg gag aag ggc tac aag atg gat gcc ccc gac ggc tgc ccg<br>Pro Arg Val Glu Lys Gly Tyr Lys Met Asp Ala Pro Asp Gly Cys Pro<br>                400                    405                  410 | 1369 |
| ccc gca gtc tat gaa gtc atg aag aac tgc tgg cac ctg gac gcc gcc<br>Pro Ala Val Tyr Glu Val Met Lys Asn Cys Trp His Leu Asp Ala Ala<br>                415                    420                  425 | 1417 |
| atg cgg ccc tcc ttc cta cag ctc cga gag cag ctt gag cac atc aaa<br>Met Arg Pro Ser Phe Leu Gln Leu Arg Glu Gln Leu Glu His Ile Lys | 1465 |

```
             430             435             440
acc cac gag ctg cac ctg tgacggctgg cctccgcctg ggtcatgggc       1513
Thr His Glu Leu His Leu
445             450 ctgtggggac tgaacctgga agatcatgga cctggtgccc ctgctcactg ggcccgagcc   1573
tgaactgagc cccagcgggc tggcgggcct ttttcctgcg tcccagcctg cacccctccg   1633
gccccgtctc tcttggaccc acctgtgggg cctggggagc ccactgaggg gccagggagg   1693
aaggaggcca cggagcggga ggcagcgccc caccacgtcg ggcttccctg gcctcccgcc   1753
actcgccttc ttagagtttt attcctttcc ttttttgaga ttttttttcc gtgtgtttat   1813
tttttattat tttcaagat aaggagaaag aaagtaccca gcaaatgggc attttacaag    1873
aagtacgaat cttatttttc ctgtcctgcc cgtgagggtg ggggggaccg ggcccctctc   1933
tagggacccc tcgccccagc ctcattcccc attctgtgtc ccatgtcccg tgtctcctcg   1993
gtcgccccgt gtttgcgctt gaccatgttg cactgtttgc atgcgcccga ggcagacgtc   2053
tgtcaggggc ttggatttcg tgtgccgctg ccacccgccc accccgccttg tgagatggaa   2113 ttgtaataaa ccacgccatg aggacaccgc cgcccgcctc ggcgcttcct ccaccgaaaa   2173
aaaaaaaaaa aaaa                                                     2187

<210> SEQ ID NO 5
<211> LENGTH: 450
<212> TYPE: PRT
<213> ORGANISM: Homo sapiens

<400> SEQUENCE: 5

Met Ser Ala Ile Gln Ala Ala Trp Pro Ser Gly Thr Glu Cys Ile Ala
  1               5                  10                  15

Lys Tyr Asn Phe His Gly Thr Ala Glu Gln Asp Leu Pro Phe Cys Lys
                 20                  25                  30

Gly Asp Val Leu Thr Ile Val Ala Val Thr Lys Asp Pro Asn Trp Tyr
             35                  40                  45

Lys Ala Lys Asn Lys Val Gly Arg Glu Gly Ile Ile Pro Ala Asn Tyr
         50                  55                  60

Val Gln Lys Arg Glu Gly Val Lys Ala Gly Thr Lys Leu Ser Leu Met
 65                  70                  75                  80

Pro Trp Phe His Gly Lys Ile Thr Arg Glu Gln Ala Glu Arg Leu Leu
                 85                  90                  95

Tyr Pro Pro Glu Thr Gly Leu Phe Leu Val Arg Glu Ser Thr Asn Tyr
                100                 105                 110

Pro Gly Asp Tyr Thr Leu Cys Val Ser Cys Asp Gly Lys Val Glu His
            115                 120                 125

Tyr Arg Ile Met Tyr His Ala Ser Lys Leu Ser Ile Asp Glu Glu Val
        130                 135                 140

Tyr Phe Glu Asn Leu Met Gln Leu Val Glu His Tyr Thr Ser Asp Ala
145                 150                 155                 160

Asp Gly Leu Cys Thr Arg Leu Ile Lys Pro Lys Val Met Glu Gly Thr
                165                 170                 175

Val Ala Ala Gln Asp Glu Phe Tyr Arg Ser Gly Trp Ala Leu Asn Met
            180                 185                 190

Lys Glu Leu Lys Leu Leu Gln Thr Ile Gly Lys Gly Glu Phe Gly Asp
        195                 200                 205

Val Met Leu Gly Asp Tyr Arg Gly Asn Lys Val Ala Val Lys Cys Ile
    210                 215                 220
```

```
Lys Asn Asp Ala Thr Ala Gln Ala Phe Leu Ala Glu Ala Ser Val Met
225                 230                 235                 240

Thr Gln Leu Arg His Ser Asn Leu Val Gln Leu Gly Val Ile Val
            245                 250                 255

Glu Glu Lys Gly Gly Leu Tyr Ile Val Thr Glu Tyr Met Ala Lys Gly
                260                 265                 270

Ser Leu Val Asp Tyr Leu Arg Ser Arg Gly Arg Ser Val Leu Gly Gly
            275                 280                 285

Asp Cys Leu Leu Lys Phe Ser Leu Asp Val Cys Glu Ala Met Glu Tyr
290                 295                 300

Leu Glu Gly Asn Asn Phe Val His Arg Asp Leu Ala Ala Arg Asn Val
305                 310                 315                 320

Leu Val Ser Glu Asp Asn Val Ala Lys Val Ser Asp Phe Gly Leu Thr
                325                 330                 335

Lys Glu Ala Ser Ser Thr Gln Asp Thr Gly Lys Leu Pro Val Lys Trp
                340                 345                 350

Thr Ala Pro Glu Ala Leu Arg Glu Lys Lys Phe Ser Thr Lys Ser Asp
            355                 360                 365

Val Trp Ser Phe Gly Ile Leu Leu Trp Glu Ile Tyr Ser Phe Gly Arg
370                 375                 380

Val Pro Tyr Pro Arg Ile Pro Leu Lys Asp Val Val Pro Arg Val Glu
385                 390                 395                 400

Lys Gly Tyr Lys Met Asp Ala Pro Asp Gly Cys Pro Pro Ala Val Tyr
                405                 410                 415

Glu Val Met Lys Asn Cys Trp His Leu Asp Ala Ala Met Arg Pro Ser
                420                 425                 430

Phe Leu Gln Leu Arg Glu Gln Leu Glu His Ile Lys Thr His Glu Leu
            435                 440                 445

His Leu
    450

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence:9E10-myc
      epitope tag

<400> SEQUENCE: 6

Val Asp Met Glu Gln Lys Leu Ile Ala Glu Glu Asp Leu Asn
 1               5                  10

<210> SEQ ID NO 7
<211> LENGTH: 4517
<212> TYPE: DNA
<213> ORGANISM: Homo sapiens
<220> FEATURE:
<221> NAME/KEY: CDS
<222> LOCATION: (208)..(1836)
<223> OTHER INFORMATION: human Yes-1 cDNA translated protein

<400> SEQUENCE: 7
gcggagccaa ggcacacggg tctgacccct gggccggccc ggagcaagtg acacggaccg      60
gtcgcctatc ctgaccacag caaagcggcc cggagcccgc ggaggggacc tgacggggcc     120
gtaggcgccg gaaggctggg ggccccggag ccggccggc gtggcccgag ttccggtgag     180
cggacggcgg cgcgcgcaga tttgata atg ggc tgc att aaa agt aaa gaa aac     234
```

```
                    Met Gly Cys Ile Lys Ser Lys Glu Asn
                     1                   5 aaa agt cca gcc att aaa tac aga cct gaa aat act cca gag cct gtc    282
Lys Ser Pro Ala Ile Lys Tyr Arg Pro Glu Asn Thr Pro Glu Pro Val
 10              15                  20                  25 agt aca agt gtg agc cat tat gga gca gaa ccc act aca gtg tca cca    330
Ser Thr Ser Val Ser His Tyr Gly Ala Glu Pro Thr Thr Val Ser Pro
                 30                  35                  40 tgt ccg tca tct tca gca aag gga aca gca gtt aat ttc agc agt ctt    378
Cys Pro Ser Ser Ser Ala Lys Gly Thr Ala Val Asn Phe Ser Ser Leu
             45                  50                  55 tcc atg aca cca ttt gga gga tcc tca ggg gta acg cct ttt gga ggt    426
Ser Met Thr Pro Phe Gly Gly Ser Ser Gly Val Thr Pro Phe Gly Gly
         60                  65                  70 gca tct tcc tca ttt tca gtg gtg cca agt tca tat cct gct ggt tta    474
Ala Ser Ser Ser Phe Ser Val Val Pro Ser Ser Tyr Pro Ala Gly Leu
 75                  80                  85 aca ggt ggt gtt act ata ttt gtg gcc tta tat gat tat gaa gct aga    522
Thr Gly Gly Val Thr Ile Phe Val Ala Leu Tyr Asp Tyr Glu Ala Arg
 90                  95                 100                 105 act aca gaa gac ctt tca ttt aag aag ggt gaa aga ttt caa ata att    570
Thr Thr Glu Asp Leu Ser Phe Lys Lys Gly Glu Arg Phe Gln Ile Ile
                110                 115                 120 aac aat acg gaa gga gat tgg tgg gaa gca aga tca atc gct aca gga    618
Asn Asn Thr Glu Gly Asp Trp Trp Glu Ala Arg Ser Ile Ala Thr Gly
            125                 130                 135 aag aat ggt tat atc ccg agc aat tat gta gcg cct gca gat tcc att    666
Lys Asn Gly Tyr Ile Pro Ser Asn Tyr Val Ala Pro Ala Asp Ser Ile
        140                 145                 150 cag gca gaa gaa tgg tat ttt ggc aaa atg ggg aga aaa gat gct gaa    714
Gln Ala Glu Glu Trp Tyr Phe Gly Lys Met Gly Arg Lys Asp Ala Glu
155                 160                 165 aga tta ctt ttg aat cct gga aat caa cga ggt att ttc tta gta aga    762
Arg Leu Leu Leu Asn Pro Gly Asn Gln Arg Gly Ile Phe Leu Val Arg
170                 175                 180                 185 gag agt gaa aca act aaa ggt gct tat tcc ctt tct att cgt gat tgg    810
Glu Ser Glu Thr Thr Lys Gly Ala Tyr Ser Leu Ser Ile Arg Asp Trp
                190                 195                 200 gat gag ata agg ggt gac aat gtg aaa cac tac aaa att agg aaa ctt    858
Asp Glu Ile Arg Gly Asp Asn Val Lys His Tyr Lys Ile Arg Lys Leu
            205                 210                 215 gac aat ggt gga tac tat atc aca acc aga gca caa ttt gat act ctg    906
Asp Asn Gly Gly Tyr Tyr Ile Thr Thr Arg Ala Gln Phe Asp Thr Leu
        220                 225                 230 cag aaa ttg gtg aaa cac tac aca gaa cat gct gat ggt tta tgc cac    954
Gln Lys Leu Val Lys His Tyr Thr Glu His Ala Asp Gly Leu Cys His
235                 240                 245 aag ttg aca act gtg tgt cca act gtg aaa cct cag act caa ggt cta   1002
Lys Leu Thr Thr Val Cys Pro Thr Val Lys Pro Gln Thr Gln Gly Leu
250                 255                 260                 265 gca aaa gat gct tgg gaa atc cct cga gaa tct ttg cga cta gag gtt   1050
Ala Lys Asp Ala Trp Glu Ile Pro Arg Glu Ser Leu Arg Leu Glu Val
                270                 275                 280 aaa cta gga caa gga tgt ttc ggc gaa gtg tgg atg gga aca tgg aat   1098
Lys Leu Gly Gln Gly Cys Phe Gly Glu Val Trp Met Gly Thr Trp Asn
            285                 290                 295 gga acc acg aaa gta gca atc aaa aca cta aaa cca ggt aca atg atg   1146
Gly Thr Thr Lys Val Ala Ile Lys Thr Leu Lys Pro Gly Thr Met Met
        300                 305                 310
```

```
cca gaa gct ttc ctt caa gaa gct cag ata atg aaa aaa tta aga cat    1194
Pro Glu Ala Phe Leu Gln Glu Ala Gln Ile Met Lys Lys Leu Arg His
            315                 320                 325 gat aaa ctt gtt cca cta tat gct gtt gtt tct gaa gaa cca att tac    1242
Asp Lys Leu Val Pro Leu Tyr Ala Val Val Ser Glu Glu Pro Ile Tyr
330                 335                 340                 345 att gtc act gaa ttt atg tca aaa gga agc tta tta gat ttc ctt aag    1290
Ile Val Thr Glu Phe Met Ser Lys Gly Ser Leu Leu Asp Phe Leu Lys
                350                 355                 360 gaa gga gat gga aag tat ttg aag ctt cca cag ctg gtt gat atg gct    1338
Glu Gly Asp Gly Lys Tyr Leu Lys Leu Pro Gln Leu Val Asp Met Ala
            365                 370                 375 gct cag att gct gat ggt atg gca tat att gaa aga atg aac tat att    1386
Ala Gln Ile Ala Asp Gly Met Ala Tyr Ile Glu Arg Met Asn Tyr Ile
        380                 385                 390 cac cga gat ctt cgg gct gct aat att ctt gta gga gaa aat ctt gtg    1434
His Arg Asp Leu Arg Ala Ala Asn Ile Leu Val Gly Glu Asn Leu Val
    395                 400                 405 tgc aaa ata gca gac ttt ggt tta gca agg tta att gaa gac aat gaa    1482
Cys Lys Ile Ala Asp Phe Gly Leu Ala Arg Leu Ile Glu Asp Asn Glu
410                 415                 420                 425 tac aca gca aga caa ggt gca aaa ttt cca atc aaa tgg aca gct cct    1530
Tyr Thr Ala Arg Gln Gly Ala Lys Phe Pro Ile Lys Trp Thr Ala Pro
                430                 435                 440 gaa gct gca ctg tat ggt cgg ttt aca ata aag tct gat gtc tgg tca    1578
Glu Ala Ala Leu Tyr Gly Arg Phe Thr Ile Lys Ser Asp Val Trp Ser
            445                 450                 455 ttt gga att ctg caa aca gaa cta gta aca aag ggc cga gtg cca tat    1626
Phe Gly Ile Leu Gln Thr Glu Leu Val Thr Lys Gly Arg Val Pro Tyr
        460                 465                 470 cca ggt atg gtg aac cgt gaa gta cta gaa caa gtg gag cga gga tac    1674
Pro Gly Met Val Asn Arg Glu Val Leu Glu Gln Val Glu Arg Gly Tyr
    475                 480                 485 agg atg ccg tgc cct cag ggc tgt cca gaa tcc ctc cat gaa ttg atg    1722
Arg Met Pro Cys Pro Gln Gly Cys Pro Glu Ser Leu His Glu Leu Met
490                 495                 500                 505 aat ctg tgt tgg aag aag gac cct gat gaa aga cca aca ttt gaa tat    1770
Asn Leu Cys Trp Lys Lys Asp Pro Asp Glu Arg Pro Thr Phe Glu Tyr
                510                 515                 520 att cag tcc ttc ttg gaa gac tac ttc act gct aca gag cca cag tac    1818
Ile Gln Ser Phe Leu Glu Asp Tyr Phe Thr Ala Thr Glu Pro Gln Tyr
            525                 530                 535 cag cca gga gaa aat tta taattcaagt agcctatttt atatgcacaa           1866
Gln Pro Gly Glu Asn Leu
            540 atctgccaaa atataaagaa cttgtgtaga ttttctacag gaatcaaaag aagaaaatct  1926 tctttactct gcatgttttt aatggtaaac tggaatccca gatatggttg cacaaaacca  1986 ctttttttc cccaagtatt aaactctaat gtaccaatga tgaatttatc agcgtatttc   2046 agggtccaaa caaatagag ctaagatact gatgacagtg tgggtgacag catggtaatg   2106 aaggacagtg aggctcctgc ttatttataa atcatttcct ttctttttt ccccaaagtc   2166 agaattgctc aaagaaaatt atttattgtt acagataaaa cttgagagat aaaaagctat  2226 accataataa aatctaaaat taaggaatat catgggacca ataattcca ttccagtttt   2286 ttaaagtttc ttgcatttat tattctcaaa agtttttttct aagttaaaca gtcagtatgc 2346 aatcttaata tatgctttct tttgcatgga catgggccag gttttttcaaa aggaatataa 2406 acaggatctc aaacttgatt aaatgttaga ccacagaagt ggaatttgaa agtataatgc  2466
```

```
agtacattaa tattcatgtt catggaactg aaagaataag aacttttca cttcagtcct      2526 tttctgaaga gtttgactta gaataatgaa ggtaactaga aagtgagtta atcttgtatg      2586
aggttgcatt gatttttaa ggcaatatat aattgaaact actgtccaat caaaggggaa      2646
atgttttgat ctttagatag catgcaaagt aagacccagc attttaaaag ccctttttta      2706
aaaactagac ttcgtactgt gagtattgct tatatgtcct tatggggatg ggtgccacaa      2766
atagaaaata tgaccagatc agggacttga atgcactttt gctcatggtg aatatagatg      2826
aacagagagg aaaatgtatt taaagaaat acgagaaaag aaaatgtgaa agttttacaa      2886
gttagaggga tggaaggtaa tgtttaatgt tgatgtcatg gagtgacaga atggctttgc      2946
tggcactcag agctcctcac ttagctatat tctgagactt tgaagagtta taagtataa      3006 ctataaaact aattttctt acacactaaa tgggtatttg ttcaaaataa tgaagttatg      3066
gcttcacatt cattgcagtg ggatatggtt tttatgtaaa acatttttag aactccagtt      3126
ttcaaatcat gtttgaatct acattcactt ttttttgttt ctttttttga dacggagtct      3186
cgctctgccg cccaggctgg agtgcagtgg cgcgatctcg gctcactgca agctctgcct      3246
cccaggttca caccattctc ctgcctcagc ctcccgagta gctgggacta caggtgccca      3306
ccaccacgcc tggctagttt tttgtatttt tagtagagac gcagtttcac cgtgttagcc      3366
aggatggtct cgatctcctg accttgtgat ctgcccgcct cggcctccca aagtgctggg      3426
attacaggtg tgagccaccg cgcccagcct acattcactt ctaaagtcta tgtaatggtg      3486 gtcattttt ccctttaga atacattaaa tggttgattt ggggaggaaa acttattctg      3546
aatattaacg gtggtgaaaa ggggacagtt tttaccctaa agtgcaaaag tgaaacatac      3606
aaaataagac taatttttaa gagtaactca gtaatttcaa aatacagatt tgaatagcag      3666
cattagtggt ttgagtgtct agcaaaggaa aaattgatga ataaaatgaa ggtctggtgt      3726
atatgtttta aaatactctc atatagtcac actttaaatt aagccttata ttaggcccct      3786 ctatttcag gatataattc ttaactatca ttatttacct gattttaatc atcagattcg      3846
aaattctgtg ccatggcgta tatgttcaaa ttcaaaccat ttttaaaatg tgaagatgga      3906
cttcatgcaa gttggcagtg gttctggtac taaaaattgt ggttgttttt tctgtttacg      3966
taacctgctt agtattgaca ctctctacca agagggtctt cctaagaaga gtgctgtcat      4026
tatttcctct tatcaacaac ttgtgacatg agatttttta agggctttat gtgaactatg      4086
atattgtaat ttttctaagc atattcaaaa gggtgacaaa attacgttta tgtactaaat      4146
ctaatcagga aagtaaggca ggaaaagttg atggtattca ttaggtttta actgaatgga      4206
gcagttcctt atataataac aattgtatag tagggataaa acactaacaa tgtgtattca      4266
ttttaaattg ttctgtattt ttaaattgcc aagaaaaaca actttgtaaa tttggagata      4326
ttttccaaca gcttttcgtc ttcagtgtct taatgtggaa gttaacccctt accaaaaaag      4386 gaagttggca aaaacagcct tctagcacac ttttttaaat gaataatggt agcctaaact      4446 taatatttt ataagtatt gtaatattgt tttgtggata attgaaataa aaagttctca      4506
ttgaatgcac c                                                           4517
```

<210> SEQ ID NO 8
<211> LENGTH: 543
<212> TYPE: PRT
<213> ORGANISM: Homo sapiens

<400> SEQUENCE: 8

```
Met Gly Cys Ile Lys Ser Lys Glu Asn Lys Ser Pro Ala Ile Lys Tyr
 1               5                  10                  15

Arg Pro Glu Asn Thr Pro Glu Pro Val Ser Thr Ser Val Ser His Tyr
            20                  25                  30

Gly Ala Glu Pro Thr Thr Val Ser Pro Cys Pro Ser Ser Ser Ala Lys
        35                  40                  45

Gly Thr Ala Val Asn Phe Ser Ser Leu Ser Met Thr Pro Phe Gly Gly
    50                  55                  60

Ser Ser Gly Val Thr Pro Phe Gly Gly Ala Ser Ser Ser Phe Ser Val
65                  70                  75                  80

Val Pro Ser Ser Tyr Pro Ala Gly Leu Thr Gly Val Thr Ile Phe
                85                  90                  95

Val Ala Leu Tyr Asp Tyr Glu Ala Arg Thr Thr Glu Asp Leu Ser Phe
            100                 105                 110

Lys Lys Gly Glu Arg Phe Gln Ile Ile Asn Asn Thr Glu Gly Asp Trp
        115                 120                 125

Trp Glu Ala Arg Ser Ile Ala Thr Gly Lys Asn Gly Tyr Ile Pro Ser
    130                 135                 140

Asn Tyr Val Ala Pro Ala Asp Ser Ile Gln Ala Glu Glu Trp Tyr Phe
145                 150                 155                 160

Gly Lys Met Gly Arg Lys Asp Ala Glu Arg Leu Leu Leu Asn Pro Gly
                165                 170                 175

Asn Gln Arg Gly Ile Phe Leu Val Arg Glu Ser Glu Thr Thr Lys Gly
            180                 185                 190

Ala Tyr Ser Leu Ser Ile Arg Asp Trp Asp Glu Ile Arg Gly Asp Asn
        195                 200                 205

Val Lys His Tyr Lys Ile Arg Lys Leu Asp Asn Gly Gly Tyr Tyr Ile
    210                 215                 220

Thr Thr Arg Ala Gln Phe Asp Thr Leu Gln Lys Leu Val Lys His Tyr
225                 230                 235                 240

Thr Glu His Ala Asp Gly Leu Cys His Lys Leu Thr Thr Val Cys Pro
                245                 250                 255

Thr Val Lys Pro Gln Thr Gln Gly Leu Ala Lys Asp Ala Trp Glu Ile
            260                 265                 270

Pro Arg Glu Ser Leu Arg Leu Glu Val Lys Leu Gly Gln Gly Cys Phe
        275                 280                 285

Gly Glu Val Trp Met Gly Thr Trp Asn Gly Thr Thr Lys Val Ala Ile
    290                 295                 300

Lys Thr Leu Lys Pro Gly Thr Met Met Pro Glu Ala Phe Leu Gln Glu
305                 310                 315                 320

Ala Gln Ile Met Lys Lys Leu Arg His Asp Lys Leu Val Pro Leu Tyr
                325                 330                 335

Ala Val Val Ser Glu Glu Pro Ile Tyr Ile Val Thr Glu Phe Met Ser
            340                 345                 350

Lys Gly Ser Leu Leu Asp Phe Leu Lys Glu Gly Asp Gly Lys Tyr Leu
        355                 360                 365

Lys Leu Pro Gln Leu Val Asp Met Ala Ala Gln Ile Ala Asp Gly Met
    370                 375                 380

Ala Tyr Ile Glu Arg Met Asn Tyr Ile His Arg Asp Leu Arg Ala Ala
385                 390                 395                 400

Asn Ile Leu Val Gly Glu Asn Leu Val Cys Lys Ile Ala Asp Phe Gly
                405                 410                 415

Leu Ala Arg Leu Ile Glu Asp Asn Glu Tyr Thr Ala Arg Gln Gly Ala
```

-continued

```
                420                 425                 430
Lys Phe Pro Ile Lys Trp Thr Ala Pro Glu Ala Ala Leu Tyr Gly Arg
        435                 440                 445

Phe Thr Ile Lys Ser Asp Val Trp Ser Phe Gly Ile Leu Gln Thr Glu
        450                 455                 460

Leu Val Thr Lys Gly Arg Val Pro Tyr Pro Gly Met Val Asn Arg Glu
465                 470                 475                 480

Val Leu Glu Gln Val Glu Arg Gly Tyr Arg Met Pro Cys Pro Gln Gly
                485                 490                 495

Cys Pro Glu Ser Leu His Glu Leu Met Asn Leu Cys Trp Lys Lys Asp
                500                 505                 510

Pro Asp Glu Arg Pro Thr Phe Glu Tyr Ile Gln Ser Phe Leu Glu Asp
        515                 520                 525

Tyr Phe Thr Ala Thr Glu Pro Gln Tyr Gln Pro Gly Glu Asn Leu
        530                 535                 540
```

METHODS AND COMPOSITIONS USEFUL FOR MODULATION OF ANGIOGENESIS AND VASCULAR PERMEABILITY USING SRC OR YES TYROSINE KINASES

CROSS-REFERENCE TO RELATED APPLICATIONS

This application is a continuation-in-part-of International Patent Application Number PCT/US99/11780, designating the United States of America filed May 28, 1999, which claims priority to United States Provisional Application for Patent Ser. No. 60/087,220 filed May 29, 1998.

STATEMENT OF GOVERNMENT RIGHTS

This invention was made with government support under Contract Nos. CA 50286, CA 45726, CA 78045, CA 75924, HL 54444 and HL 09435 by the National Institute of Health. The government has certain rights in the invention.

TECHNICAL FIELD

The present invention relates generally to the field of medicine, and relates specifically to methods and compositions for modulating vascular permeability (VP).

BACKGROUND

Angiogenesis is a process of tissue vascularization that involves the growth of new developing blood vessels into a tissue, and is also referred to as neo-vascularization. The process is mediated by the infiltration of endothelial cells and smooth muscle cells. The process is believed to proceed in any one of three ways: the vessels can sprout from pre-existing vessels, de-novo development of vessels can arise from precursor cells (vasculogenesis), or existing small vessels can enlarge in diameter. Blood et al., *Bioch. Biophys. Acta*, 1032:89–118 (1990). For angiogenesis to occur, endothelial cells must first degrade and cross the blood vessel basement membrane in a similar manner used by tumor cells during invasion and metastasis formation. Angiogenesis is generally absent in adult or mature tissues, although it does occur in wound healing and in the corpus luteum growth cycle. See, for example, Moses et al., *Science*, 248:1408–1410 (1990).

While angiogenesis is an important process in neonatal growth, it is also important in wound healing and is a factor in the pathogenesis of a large variety of clinical diseases including tissue inflammation, arthritis, tumor growth, diabetic retinopathy, macular degeneration by neovascularization of the retina, and like conditions. These clinical manifestations associated with angiogenesis are referred to as angiogenic diseases. Folkman et al., *Science*, 235:442–447 (1987).

It has been proposed that inhibition of angiogenesis would be a useful therapy for restricting tumor growth. Inhibition of angiogenesis has been proposed by (1) inhibition of release of "angiogenic molecules" such as bFGF (basic fibroblast growth factor), (2) neutralization of angiogenic molecules, such as by use of anti-βbFGF antibodies, (3) use of inhibitors of vitronectin receptor ($\alpha_v\beta_3$), and (4) inhibition of endothelial cell response to angiogenic stimuli. This latter strategy has received attention, Folkman et al., *Cancer Biology*, 3:89–96 (1992), have described several endothelial cell response inhibitors, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like that might be used to inhibit angiogenesis. For additional proposed inhibitors of angiogenesis, see Blood et al., *Bioch. Biophys. Acta.*, 1032:89–118 (1990), Moses et al., *Science*, 248:1408–1410 (1990), Ingber et al., *Lab. Invest.*, 59:44–51 (1988), and U.S. Pat. No. 5,092,885, U.S. Pat. No. 5,112,946, U.S. Pat. No. 5,192,744, U.S. Pat. No. 5,202,352, U.S. Pat. No. 5,753,230 and U.S. Pat. No. 5,766,591. None of the inhibitors of angiogenesis described in the foregoing references involve the Src proteins, however.

It has been previously reported that angiogenesis depends on the interaction between vascular integrins and extracellular matrix proteins. Brooks et al., *Science*, 264:569–571 (1994). Furthermore, it was reported that programmed cell death (apoptosis) of angiogenic vascular cells is initiated by the interaction, which would be inhibited by certain antagonists of the vascular integrin $\alpha_v\beta_3$. Brooks et al., *Cell*, 79:1157–1164 (1994). More recently, it has been reported that the binding of matrix metalloproteinase-2 (MMP-2) to vitronectin receptor ($\alpha_v\beta_5$) can be inhibited using $\alpha_v\beta_5$ antagonists, and thereby inhibit the enzymatic function of the proteinase. Brooks et al., *Cell*, 85:683–693 (1996).

The brain vasculature is characterized by a highly restrictive blood-brain barrier that prohibits small molecules from extravasating into the surrounding brain tissue. The nature of the blood-brain barrier in mammals has been of special concern with pharmacological studies, as many drugs are routinely prevented from passing from the vasculature to the brain tissues because of the highly restrictive blood-brain barrier. The present invention involves the unexpected discovery that VP, as measured by vascular leakage of blood, can be modulated by src or yes. Moreover, VP has been associated with angiogenesis and other pathologies. Inflammation induced increased vascular permeability is associated with edema and swelling.

SUMMARY OF THE INVENTION

The present invention is directed to modulation of vascular permeability (VP) by tyrosine kinase Src, also referred to generically herein as Src, or the tyrosine kinase Yes, also referred to generically herein as Yes.

Thus, one aspect of the invention encompasses pharmaceutical compositions for modulating VP in target tissue of a mammal. The compositions of the invention comprise a therapeutically effective VP modulating amount of a mixture of tyrosine kinase protein Src and Yes, in a pharmaceutically acceptable carrier.

In compositions which comprise active Src and Yes kinase proteins, the expected modulation is a potentiation or increase in vascular permeability of the blood vessels in a target tissue. Where the desired Src protein is an active kinase, a preferred Src is Src-A. Another preferred active Src protein is one in which the amino acid residue at position 527 of the Src protein is any amino acid residue except for tyrosine, serine or threonine. The preferred active Yes protein will have the kinase activity of wild-type human Yes, such as that or the Yes-1 protein. Another preferred active Yes is one in which the kinase inactivating phosphorylation site of the Yes protein is mutated to abolish or minimize inactivating phosphorylation, similar to a mutation of amino acid residue 527 of Src to any amino acid residue except for tyrosine, serine or threonine.

Where the composition comprises Src and Yes protein that are inactive kinase proteins, the expected modulation is an inhibition or decrease in vascular permeability of the blood vessels in the target tissue. When the desired Src protein is an inactive protein, a preferred Src is Src 251. A further preferred inactive Src is Src K295M. A preferred inactive Yes protein will have diminished kinase activity as compared with the wild-type protein.

A further aspect of the claimed invention is a pharmaceutical composition comprising a therapeutically effective VP modulating amount of nucleic acid capable of expressing tyrosine kinase protein Src and Yes, when transfected into a target cell, in a suitable pharmaceutical carrier. The expressible nucleic acids encoding for Src or Yes protein can comprise nucleic acid segments which describe all or part of the Yes or Src protein. When transferred into target cells, the target cell transcribes and translates the nucleic acid sequence to express the desired protein.

Where the modulation is a potentiation or increase in vascular permeability of the blood vessels in the target tissue, Src encoding nucleic acid will encode active forms of Src, and Yes encoding nucleic acids will encode active forms of Yes kinase proteins. Once transferred into the target host cell, the nucleic acids will be expressed by the host cell. A preferred Src encoding nucleic acid encodes active Src A protein. A further preferred Src encoding nucleic acid encodes a mutated active Src where the amino acid residue at position 527 of the expressed Src protein is any amino acid residue except for tyrosine, serine or threonine. A preferred Yes encoding nucleic acid will encode the wild-type protein, or a protein modified to abolish or inhibit the inactivating phosphorylation site of the Yes protein, in a similar manner as the Src position 527 mutation described.

When the desired modulation is an inhibition or decrease in vascular permeability of the blood vessels in the target tissue, a preferred inactive Src encoding nucleic acid encodes Src 251 protein. A further preferred inactive Src encoding nucleic acid encodes inactive Src K295M. A preferred inactive Yes encoding nucleic acid will encode a protein that has diminished kinase activity.

It is envisioned that the compositions of the invention can comprise a mixture of nucleic acids, where each nucleic acid can comprise an expressible src or yes gene. In addition, it is envisioned that a single nucleic acid may comprise both a nucleic acid encoding for a Src protein, and a nucleic acid encoding for a Yes protein.

For refined modulation of angiogenesis and VP in target tissues, the pharmaceutical compositions of the invention can comprise a mixture of active or inactive tyrosine kinase protein Src, or tyrosine kinase protein Yes. Similarly, the pharmaceutical compositions of the invention can comprise a mixture of nucleic acid capable of expressing active or inactive tyrosine kinase protein Src, or tyrosine kinase protein Yes.

In this embodiment, by utilizing differentially expressible promoters or other such regulatory elements, a first low expressing first tyrosine kinase gene may be co-administered with a second high expressing second tyrosine kinase gene, according to the teaching of the invention. In this embodiment, an increase in angiogenesis can be accomplished while also maintaining, minimizing or reducing VP, by using a first low expressing active src gene, in combination with a second high expressing inactive yes gene. This co-administration can be accomplished by using separate expression vectors, or a single combined expression vector construct. Similarly, a decrease in angiogenesis can be accomplished while also maintaining, potentiating or increasing VP, by using a first low expressing inactive src gene, in combination with a second high expressing active yes gene. Further degrees of modulation can be accomplished by the various permutations of high/low and src/yes, in combination with selection of the activity of promotor elements, and inducible promoters.

It is envisioned that the individual src and yes genes may be under the regulatory control of the same or different regulatory nucleic acid sequences such as and not limited to enhancers, repressors, and promoter elements. When the two or more proteins are expressible from a single vector, it is envisioned that regulation and control of the transcription of the independent protein genes can be under the control of the same regulatory elements. It is also envisioned that regulation and control of transcription can be effected by two or more independently operating regulatory elements. Regulatory elements are known in the art, and can be constiutively active, or inducible, enhancer, promoter, suppressor, or the like, nucleic acid sequences.

It is envisioned that the nucleic acid compositions of the invention can comprise viral and/or non-viral gene transfer vector containing a nucleic acid segment encoding for a Src and/or Yes protein. Retroviral and non-viral gene transfer and expression vectors are known in the art, and described briefly below.

A preferred nucleic acid encodes Src-A protein. Another preferred active Src protein is one in which the amino acid residue at position 527 of the Src protein is any amino acid residue except for tyrosine, serine or threonine.

It is envisioned that a mixture of Src and Yes protein, and/or nucleic acid encoding for such protein, can combine active and inactive forms of protein, depending upon the level of modulation desired, and the coordinated effect on angiogenesis and VP desired, according to the teaching of the present invention.

A composition providing the Src or Yes protein can contain purified protein, biologically active fragments of natural protein, recombinantly produced Src or Yes protein or protein fragments or fusion proteins, or gene/nucleic acid expression vectors for expressing a Src or Yes protein, or mixtures thereof.

Where the Src or Yes protein is inactivated or inhibited, the modulation is an inhibition of VP. Where the Src or Yes protein is active or activated, the modulation is a potentiation of VP.

The present invention encompasses methods for treating mammalian tissue with a composition comprising a therapeutically effective, VP-modulating amount of a Src or Yes protein, or combination thereof. In the methods of the invention, Src and Yes tyrosine kinase protein, or nucleic acid expression vectors capable of expressing such protein is administered to tissue suffering from a disease condition that responds to modulation of VP.

Where the therapeuticly effective VP modulating effect desired is an increase or potentiation of VP, it is contemplated that active forms of Src protein and/or Yes protein can be administered. Similarly, the methods encompass the administration of expressible nucleic acids which encode active or inactive forms of Src protein and/or Yes protein, accordingly.

The tissue to be treated can be any tissue in which modulation of VP is desirable. Therapeutic treatment is accomplished by contacting the target tissue with an effective amount of the desired modulating composition, and allowed sufficient time of contact for the protein or nucleic acid components of the pharmaceutical to enter the target tissue. For VP inhibition, it is useful to treat diseased tissue where deleterious vascular leaking is occurring. Exemplary tissues include inflamed tissue, tissues associated with stroke, myocardial infarction, or other blockage of normal flow, tissues undergoing restenosis, and the like tissues.

For potentiation, it is useful to treat patients with ischemic limbs in which there is poor circulation in the limbs from diabetic or other conditions, or for potentiating the administration of drugs to the brain across the blood-brain barrier. Patients with chronic wounds which do not heal and therefore could benefit from the increase in vascular cell proliferation and neovascularization as modulated by VP can be treated as well.

A further aspect of the present invention are articles of manufacture which comprise packaging material and a pharmaceutical composition contained within said packaging material, wherein said pharmaceutical composition is capable of modulating vascular permeability in a tissue suffering from a disease condition, wherein said packaging material comprises a label which indicates that said pharmaceutical composition can be used for treating disease conditions by modulating vascular permeability, and wherein said pharmaceutical composition comprises a therapeutically effective amount of tyrosine kinase protein Yes, in a pharmaceutically acceptable carrier. This embodiment encompasses Yes protein in active or inactive form, and also nucleic acids encoding for active or inactive Yes protein. Both retroviral and non-viral gene transfer/expression vectors can contain a nucleic acid segment encoding for Yes protein, either in active or inactive form, or both. When both active and inactive forms of a protein kinase gene are present, it is contemplated that the genes are under separate inducible promoter regulation to allow for alternative expression, as desired.

A further aspect of the present invention are articles of manufacture wherein the pharmaceutical composition comprises a therapeutically effective VP modulating amount of a tyrosine kinase protein Src and Yes, in a pharmaceutically acceptable carrier. Where the article of manufacture is packaged to indicate a potentiating VP modulating effect, Src and Yes are in active form. A preferred active Src is Src-A protein. Another preferred active Src protein is one in which the amino acid residue at position 527 of the Src protein is any amino acid residue except for tyrosine, serine or threonine.

A further aspect of the present invention are articles of manufacture which comprise a pharmaceutical composition wherein said pharmaceutical composition comprises a therapeutically effective VP modulating amount of an inactive tyrosine kinase protein Src and Yes protein, in a pharmaceutically acceptable carrier, where the desired modulation is an inactivation or inhibition of VP. A preferred inactive Src is Src 251 protein. Another preferred inactive Src protein is Src K295M.

Similarly, a further aspect of the present invention are articles of manufacture wherein the pharmaceutical composition comprises a nucleic acid capable of expressing tyrosine kinase protein Src and Yes, in a suitable pharmaceutical carrier. A preferred nucleic acid component of the pharmaceutical composition of this article of manufacture encode an active Src protein, where the modulation desired is a potentiation or activation of VP. Further envisioned are nucleic acid encoding active Yes protein. A preferred active Src is Src-A protein. Another preferred active Src encoding nucleic acid is one in which the amino acid residue at position 527 of the Src protein is any amino acid residue except for tyrosine, serine or threonine. It is also envisioned that a single nucleic acid can be constructed which will express both yes and src, either independently regulated, or under transcriptional control of the same promoter, enhancer, suppressor, repressor or other suitable regulatory nucleic acid sequence.

The pharmaceutical composition of the article of manufacture can vary depending upon the desired modulatory effect, and the packaging labeling will correspondingly vary as well.

BRIEF DESCRIPTION OF THE DRAWINGS

In the drawings forming a portion of this disclosure:

FIG. 1 is a cDNA sequence of chicken c-Src which is the complete coding sequence with the introns deleted as first described by Takeya et al., *Cell*, 32:881–890 (1983). The sequence is accessible through GenBank Accession Number J00844. The sequence contains 1759 nucleotides with the protein coding portion beginning and ending at the respective nucleotide positions 112 and 1713 (SEQ ID NO.2).

FIG. 2 is the encoded amino acid residue sequence of chicken c-Src of the coding sequence shown in FIG. 1 (SEQ ID NO.3).

FIG. 3 is a cDNA sequence of human c-Src which as first described by Braeuninger et al., *Proc. Natl. Acad. Sci., USA*, 88:10411–10415 (1991). The sequence is accessible through GenBank Accession Number X59932 X71157. The sequence contains 2187 nucleotides with the protein coding portion beginning and ending the respective nucleotide positions 134 and 1486(SEQ ID NO.4).

FIG. 4 is the encoded amino acid residue sequence of human c-Src of the coding sequence shown in FIG. 3 (SEQ ID NO.5).

FIG. 7A shows tissue extracts of 10 day-old chick CAMs that had been exposed to VEGF or PMA for 30 minutes or infected with c-src A retrovirus for 48 hours. NT stands for no treatment. Src was immunoprecipitated from equivalent amounts of total protein extract and subjected to an in vitro immune complex kinase assay using a FAK-GST fusion protein as a substrate, electrophoresed and transferred to nitrocellulose. Aliquots of the above whole tissue lysates were also measured for endogenous ERK phosphorylation by immunoblotting with an anti-phospho-ERK antibody. FIG. 7B shows 10 day old CAMs that were infected with either mock RCAS or RCAS containing SRC A. After two days, CAMs were dissected, cryopreserved in OCT and sectioned at 4 μm. Sections were immunostained with an anti-phosphorylated ERK antibody (New England Biolabs.), washed and detected with a goat anti-rabbit FITC-conjugated secondary antibody. Florescent images were captured on a cooled-CCD camera (Princeton Inst.)

FIGS. 8A–8C illustrate the selective requirement for Src activity during VEGF, but not bFGF-induced angiogenesis. Nine day old chick CAMs were exposed to RCAS-Src 251 or control RCAS-GFP retroviruses or buffer for 20 hours and then incubated for an additional 72 hours in the presence or absence of bFGF or VEGF. The level of angiogenesis was quantified FIG. 8A as described above, and representative photomicrographs (6×) were taken with a stereomicroscope as shown in FIG. 8B. FIG. 8C shows a blot probed with an anti-Src antibody to confirm the expression of Src 251 in transfected cells as compared to mock treatments.

FIG. 9A is a micrograph that shows human medulloblastoma tumor fragment infected with RCAS-GFP (RCAS-Green Fluorescent Protein) expressing GFP exclusively in the tumor blood vessels (arrowhead) as detected by optical sectioning with a Bio Rad laser confocal scanning microscope (bar=500 µm). FIG. 9B depicts data from tumors treated with topical application of retrovirus, which were allowed to grow for 3 or 6 days after which they were resected and wet weights determined. Data are expressed as the mean change in tumor weight (from the 50 mg tumor starting weight) +/−SEM of 2 replicates. FIG. 9C depicts in representative micrographs, medulloblastoma tumors surgically removed from the embryos (bar=350 µm). The lower panels are high magnification views of each tumor showing the vasculature of each tumor in detail (bar=350 µm). The arrowhead indicates blood vessel disruption in RCAS-Src251-treated tumors.

FIG. 11 depicts the encoded amino acid residue sequence of human c-Yes protein in single letter amino acid representation (SEQ ID NO.8).

FIG. 12 depicts the nucleic acid sequence of a cDNA encoding for human c-Yes protein. The sequence is accessible through GenBank Accession Number M15990. The sequence contains 4517 nucleotides with the protein coding portion beginning and ending at the respective nucleotide positions 208 and 1839, and translating into to amino acid depicted in FIG. 11 (SEQ ID NO.7).

FIG. 13A illustrates immunoblotting results for detecting flk expression. FIG. 13B illustrates immunoblotting results from assay for flk under VEGF and bFGF stimulated conditions. FIG. 13C is a graph which plots the number of CD34 positive blood vessels (average of triplicate random fields at 20×) by treatment as stimulated by VEGF and bFGF in the presence of GFP, Src 251, or CSK retrovirus.

FIGS. 14A–14C illustrate results from a modified Miles assay for VP of VEGF in the skin of mice deficient in src, fyn and yes. FIG. 14A are photographs of treated ears. FIG. 14B are graphs of experimental results for stimulation of the various deficient mice. FIG. 14C plots the amount of eluted Evan's blue dye by treatment.

DETAILED DESCRIPTION OF THE DRAWINGS

A. Definitions

Figure 5:
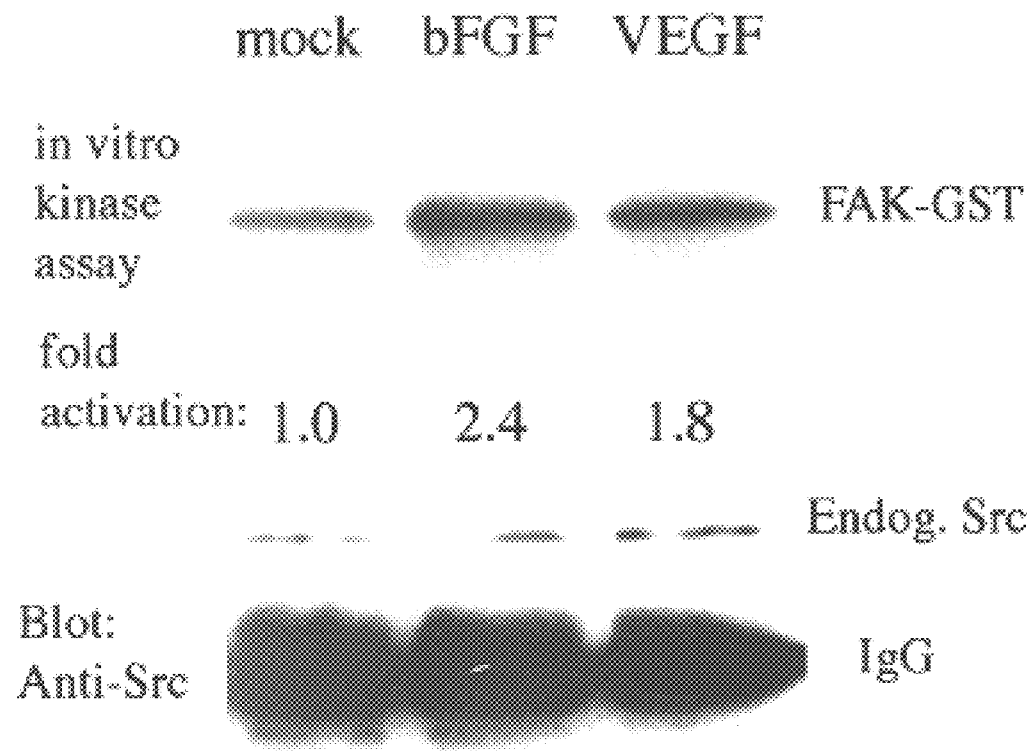
FIG. 5 illustrates the activation of endogenous Src by bFGF or VEGF as described in Example 4. The top portion of the figure indicates the results of an in vitro kinase assay with the fold activation of endogenous c-Src by either bFGF and VEGF. The bottom of the figure is the kinase assay blot probed with an anti-Src antibody as a loading control for equivalent Src-and IgG content.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 CFR §1.822(b)(2)).

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

Polypeptide: refers to a linear series of amino acid residues connected to one another by peptide bonds between the alpha-amino group and carboxy group of contiguous amino acid residues.

Peptide: as used herein refers to a linear series of no more than about 50 amino acid residues connected one to the other as in a polypeptide.

Cyclic peptide: refers to a compound having a heteroatom ring structure that includes several amide bonds as in a typical peptide. The cyclic peptide can be a homodetic "head to tail" cyclized linear polypeptide in which a linear peptide's n-terminus has formed an amide bond with the c-terminal carboxylate of the linear peptide, or it can contain a ring structure in which the polymer is heterodetic and comprises amide bonds and/or other bonds to close the ring, such as disulfide bridges, thioesters, thioamides, guanidino, and the like linkages.

Protein: refers to a linear series of greater than 50 amino acid residues connected one to the other as in a polypeptide.

Fusion protein: refers to a polypeptide containing at least two different polypeptide domains operatively linked by a typical peptide bond ("fused"), where the two domains correspond to peptides no found fused in nature.

Synthetic peptide: refers to a chemically produced chain of amino acid residues linked together by peptide bonds that is free of naturally occurring proteins and fragments thereof.

B. General Considerations

The present invention relates generally to the discovery that VEGF induced VP is specifically mediated by the tyrosine kinase proteins Src and Yes, and that VP can be modulated by providing either active or inactive Src or Yes proteins for potentiating or inhibiting angiogenesis, respectively.

This discovery is important because of the role that vascular permeability plays in a variety of disease processes and in association with angiogenesis, the formation of new blood vessels. Where tissues associated with a disease condition require angiogenesis for tissue growth, it is desirable to inhibit angiogenesis and thereby inhibit the diseased tissue growth. Angiogenesis may be more effectively inhibited by simultaneously inhibiting VP. Where injured tissue requires angiogenesis for tissue growth and healing, it is desirable to potentiate or promote VP and thus angiogenesis, and thereby promote tissue healing and growth.

Where the growth of new blood vessels is the cause of, or contributes to, the pathology associated with a disease tissue, inhibition of VP, and thereby angiogenesis will reduce the deleterious effects of the disease. By inhibiting VP associated with angiogenesis, one can intervene in the disease, ameliorate the symptoms, and in some cases cure the disease.

In certain instances, increased VP is desirable for increasing the efficacy of drug delivery via systemic administration. The blood-brain barrier is a term used to describe the tight regulation of VP, and thus minimal access of even small molecule drugs to the brain from the circulation. The ability to selectively and specifically modulate the permeability of the blood-brain barrier via modulation of the VP of the involved blood vessels will allow the administration of drugs that otherwise would not be able to pass via the circulation into the brain tissues.

Similarly, many stroke induced pathologies and damage are instigated by the sudden increase in VP, and thus the ability to specifically modulate VP will allow for novel and effective treatments to reduce the adverse effects of stroke.

The methods of the present invention are effective in part because the therapy is highly selective for VP and not other biological processes.

The present invention relates generally to the discovery that angiogenesis is mediated by the tyrosine kinase Src protein, and that angiogenesis can be modulated by providing either active or inactive Src proteins for potentiating or inhibiting angiogenesis, respectively.

This discovery is important because of the role that angiogenesis, the formation of new blood vessels, plays in a variety of disease processes. Where tissues associated with a disease condition require angiogenesis for tissue growth, it is desirable to inhibit angiogenesis and thereby inhibit the diseased tissue growth. Where injured tissue requires angiogenesis for tissue growth and healing, it is desirable to potentiate or promote angiogenesis and thereby promote tissue healing and growth.

Where the growth of new blood vessels is the cause of, or contributes to, the pathology associated with a disease tissue, inhibition of angiogenesis will reduce the deleterious effects of the disease. By inhibiting angiogenesis, one can intervene in the disease, ameliorate the symptoms, and in some cases cure the disease.

Examples of tissue associated with disease and neovascularization that will benefit from inhibitory modulation of angiogenesis include rheumatoid arthritis, diabetic retinopathy, inflammatory diseases, restenosis, and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor grow beyond a few millimeters in thickness, and for the establishment of solid tumor metastases.

Where the growth of new blood vessels is believed to contribute to healing of tissue, potentiation of angiogenesis will assist in healing. Examples include treatment of patients with ischemic limbs in which there is poor circulation in the limbs from diabetes or other conditions. Also contemplated are patients with chronic wounds which do not heal and therefore could benefit from the increase in vascular cell proliferation and neovascularization.

The methods of the present invention are effective in part because the therapy is highly selective for angiogenesis and not other biological processes.

As described earlier, angiogenesis includes a variety of processes involving neovascularization of a tissue including "sprouting", vasculogenesis, or vessel enlargement, all of which angiogenesis processes are effected by Src protein. With the exception of traumatic wound healing, corpus luteum formation and embryogenesis, it is believed that the majority of angiogenesis processes are associated with disease processes and therefore the use of the present therapeutic methods are selective for the disease and do not have deleterious side effects.

C. Src Family Tyrosine kinase Proteins

A tyrosine kinase protein for use in the present invention can vary depending upon the intended use. The terms "Src protein" or "Src" are used to refer collectively to the various forms of tyrosine kinase Src protein described herein, either in active or inactive forms. The terms "Yes protein" or "Yes" are used to refer collectively to the various forms of tyrosine kinase Yes protein described herein, either in active or inactive forms.

An "active Src protein" refers to any of a variety of forms of Src protein which potentiate angiogenesis or VP. An "active Yes protein" refers to any of a variety of forms of Yes protein which potentiate VP. Assays to measure potentiation of angiogenesis or VP are described herein, and are not to be construed as limiting. A protein is considered active if the level of angiogenesis or VP is at least 10% greater, preferably 25% greater, and more preferably 50% greater than a control level where no protein is added to the assay system.

The preferred assay for measuring potentiation of angiogenesis is the CAM assay using RCAS viral vector as described in the Examples in which the angiogenic index is calculated by counting branch points.

A preferred assay for measuring potentiation of VP is the Miles assay using Evan's blue dye in mice as described in the Examples, in which VP is measured by the amount of Evan's blue dye leaked from blood vessels.

A preferred active Src or Yes protein exhibits tyrosine kinase activity as well. Exemplary active Src or Yes proteins are described in the Examples, and include Src-A and Yes-1.

An "inactive Src protein" refers to any of a variety of forms of Src protein which inhibit angiogenesis or VP. An "inactive Yes protein" refers to any of a variety of forms of Yes protein which inhibit VP. Assays to measure inhibition of VP increase are described herein, and are not to be construed as limiting. A Src protein is considered inactive if the level of angiogenesis is at least 10% lower, preferably 25% lower, and more preferably 50% lower than a control level where no exogenous Src is added to the assay system.

A Src or Yes protein is considered:inactive if the level of VP is at least the same as, or 10% lower, preferably 25% lower, and more preferably 50% lower than a control level where no exogenous Src or Yes is added to the assay system.

The preferred assay for measuring inhibition of angiogenesis is the CAM assay using RCAS viral vector as described in the Examples in which the angiogenic index is calculated by counting branch points.

A preferred assay for measuring inhibition of VP is the Miles assay using Evan's blue dye in mice as described in the Examples, in which VP is measured by the amount of Evan's blue dye leaked from blood vessels.

A preferred inactive Src or Yes protein exhibits reduced tyrosine kinase activity as well. Exemplary inactive Src proteins are described in the Examples, and include Src-251 and Src K295M.

A Src protein useful in the present invention can be produced in any of a variety of methods including isolation from natural sources including tissue, production by recombinant DNA expression and purification, and the like. Src and/or Yes protein can also be provided "in situ" by introduction of a gene therapy system to the tissue of interest which then expresses the protein in the tissue.

A gene encoding a Src or Yes protein can be prepared by a variety of methods known in the art, and the invention is not to be construed as limiting in this regard. For example, the natural history of Src is well known to include a variety of homologs from mammalian, avian, viral and the like species, and the gene can readily be cloned using cDNA cloning methods from any tissue expressing the protein. A preferred Src for use in the invention is a cellular protein, such as the mammalian or avian homologs designated c-src. Particularly preferred is human c-src. A preferred Yes for use in the invention is a human cellular protein, c-yes. Particularly preferred is human c-yes-1 encoding for the amino acid sequence as depicted in FIG. 11. The protein Yes-1 of FIG. 11 is encoded for by a segment of the nucleic acid sequence depicted in FIG. 12, and identified as the coding domain segment.

D. Recombinant DNA Molecules and Expression Systems for Expression of Src or Yes Protein The invention describes several nucleotide sequences of particular use in the present invention. These sequences include sequences which encode a Src protein useful in the invention, and various DNA segments, recombinant DNA (rDNA) molecules and vectors constructed for expression of Src protein. These sequences also include sequences which encode a Yes protein useful in the invention, and various DNA segments, recombinant DNA (rDNA) molecules and vectors constructed for expression of Yes protein.

DNA molecules (segments) of this invention therefore can comprise sequences which encode whole structural genes, fragments of structural genes, or combination of genes, and transcription units as described further herein.

A preferred DNA segment is a nucleotide sequence which encodes a Src or Yes protein, or both as defined herein, or biologically active fragment thereof.

The amino acid residue sequence and nucleotide sequence of a preferred Src and Yes is described in the Examples.

A preferred DNA segment codes for an amino acid residue sequence substantially the same as, and preferably consisting essentially of, an amino acid residue sequence or portions thereof corresponding to a Src or Yes protein described herein. Representative and preferred DNA segments are further described in the Examples.

The amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylation do not affect the coding relationship in any way.

A nucleic acid is any polynucleotide or nucleic acid fragment, whether it be a polyribonucleotide of polydeoxyribonucleotide, i.e., RNA or DNA, or analogs thereof. In preferred embodiments, a nucleic acid molecule is in the form of a segment of duplex DNA, i.e, a DNA segment, although for certain molecular biological methodologies, single-stranded DNA or RNA is preferred.

DNA segments are produced by a number of means including chemical synthesis methods and recombinant approaches, preferably by cloning or by polymerase chain reaction (PCR). DNA segments that encode portions of a Src protein can easily be synthesized by chemical techniques, for example, the phosphotriester method of Matteucci et al, *J. Am. Chem. Soc.*, 103:3185–3191, 1981, or using automated synthesis methods. In addition, larger DNA segments can readily be prepared by well known methods, such as synthesis of a group of oligonucleotides that define the DNA segment, followed by hybridization and ligation of oligonucleotides to build the complete segment. Alternative methods include isolation of a preferred DNA segment by PCR with a pair of oligonucleotide primers used on a cDNA library believed to contain members which encode a Src protein.

Of course, through chemical synthesis, any desired modifications can be made simply by substituting the appropriate bases for those encoding the native amino acid residue sequence. This method is well known, and can be readily applied to the production of the various different "modified" Src proteins described herein.

Furthermore, DNA segments consisting essentially of structural genes encoding a Src or Yes protein can be subsequently modified, as by site-directed or random mutagenesis, to introduce any desired substitutions.

1. Cloning a Src or Yes Gene

A src or yes gene of this invention can be cloned from a suitable source of genomic DNA or messenger RNA (mRNA) by a variety of biochemical methods. Cloning these genes can be conducted according to the general methods described in the Examples and as known in the art.

Sources of nucleic acids for cloning a src or yes gene suitable for use in the methods of this invention can include genomic DNA or messenger RNA (MRNA) in the form of a cDNA library, from a tissue believed to express these proteins. A preferred tissue is human lung tissue, although any other suitable tissue may be used.

A preferred cloning method involves the preparation of a cDNA library using standard methods, and isolating the Src-encoding, or Yes-encoding nucleotide sequence by PCR amplification using paired oligonucleotide primers based on the nucleotide sequences described herein. Alternatively, the desired cDNA clones can be identified and isolated from a cDNA or genomic library by conventional nucleic acid hybridization methods using a hybridization probe based on the nucleic acid sequences described herein. Other methods of isolating and cloning suitable Src or Yes encoding nucleic acids are readily apparent to one skilled in the art.

2. Gene Transfer and/or Expression Vectors

The invention contemplates a recombinant DNA molecule (rDNA) containing a DNA segment encoding a Src or Yes protein, or both, as described herein. An expressible rDNA can be produced by operatively (in frame, expressible) linking a vector to a src or yes encoding DNA segment of the present invention. Thus, a recombinant DNA molecule is a hybrid DNA molecule comprising at least two nucleic acids of a nucleotide sequences not normally found together in nature.

The choice of vector to which a DNA segment of the present invention is operatively linked depends directly, as is well known in the art, on the functional properties desired, e.g., protein expression, and the host cell to be transformed. Typical considerations in the art of constructing recombinant DNA molecules. A vector contemplated by the present invention is at least capable of directing the replication, and preferably also expression, of a structural gene included in the vector DNA segments, to which it is operatively linked.

Where an expression vector contains both an expressible src and yes nucleic acid sequence, both genes may be regulated by the same regulatory elements upstream of the first gene, or each individually regulated by separate regulatory elements.

Both prokaryotic and eukaryotic expression vectors are familiar to one of ordinary skill in the art of vector construction, and are described by Ausebel, et al., in *Current Protocols in Molecular Biology*, Wiley and Sons, New York (1993) and by Sambrook et al., *Molecular Cloning: A Laboratory Manual*, Cold Spring Harbor Laboratory, (1989). These references also describe many of the general recombinant DNA methods referred to herein.

In one embodiment, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of a structural gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), PRSET available from Invitrogen (San Diego, Calif.) and pPL and pKK223 available from Pharmacia, Piscataway, N.J.

Expression vectors compatible with eukaryotic cells, preferably those compatible with vertebrate cells, can also be used to form the recombinant DNA molecules of the present invention. Eukaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), pRc/CMV (Invitrogen, Inc.), the preferred vector described in the Examples, and the like eukaryotic expression vectors.

A particularly preferred system for gene expression in the context of this invention includes a gene delivery component, that is, the ability to deliver the gene to the tissue of interest. Suitable vectors are "infectious" vectors such as recombinant DNA viruses, adenovirus or retrovirus vectors which are engineered to express the desired protein and have features which allow infection of preselected target tissues. Particularly preferred is the replication competent avian sarcoma virus (RCAS) described herein.

Mammalian cell systems that utilize recombinant viruses or viral elements to direct expression may be engineered. For example, when using adenovirus expression vectors, the coding sequence of a polypeptide may be ligated to an adenovirus transcription/translation control complex, e.g., the late promoter and tripartite leader sequence. This chimeric gene may then be inserted into the adenovirus genome by in vitro or in vivo recombination. Insertion in a nonessential region of the viral genome (e.g., region E1 or E3) will result in a recombinant virus that is viable and capable of expressing the polypeptide in infected hosts (e.g., see Logan et al., *Proc. Natl. Acad. Sci., USA*, 81:3655–3659 (1984)). Alternatively, the vaccinia virus 7.5K promoter may be used. (e.g., see, Mackett et al., *Proc. Natl. Acad. Sci., USA*, 79:7415–7419 (1982); Mackett et al., *J. Virol.*, 49:857–864 (1984); Panicali et al., *Proc. Natl. Acad. Sci., USA*, 79:4927–4931 (1982)). Of particular interest are vectors based on bovine papilloma virus which have the ability to replicate as extrachromosomal elements (Sarver et al., *Mol. Cell. Biol.*, 1:486 (1981)). Shortly after entry of this DNA into target cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the polypeptide-encoding nucleotide sequence in host cells (Cone et al., *Proc. Natl. Acad. Sci., USA*, 81:6349–6353 (1984)). High level expression may also be achieved using inducible promoters, including, but not limited to, the metallothionine IIA promoter and heat shock promoters.

Recently, long-term survival of cytomegalovirus (CMV) promoter versus Rous sarcoma virus (RSV) promotor-driven thymidine kinase (TK) gene therapy in nude mice bearing human ovarian cancer has been studied. Cell killing efficacy of adenovirus-mediated CMV promoter-driven herpes simplex virus TK gene therapy was found to be 2 to 10 time more effective than RSV driven therapy. (Tong et al., 1999, *Hybridoma* 18(l):93–97). The design of chimeric promoters for gene therapy applications, which call for low level expression followed by inducible high-level expression has also been described. (Suzuki et al., 1996, *Human Gene Therapy* 7:1883–1893).

For long-term, high-yield production of recombinant proteins, stable expression is preferred. Rather than using expression vectors which contain viral origins of replication, host cells can be transformed with a cDNA controlled by appropriate expression control elements (e.g., promoter and enhancer sequences, transcription terminators, polyadenylation sites, etc.), and a selectable marker. As mentioned above, the selectable marker in the recombinant plasmid confers resistance to the selection and allows cells to stably integrate the plasmid into their chromosomes and grow to form foci which in turn can be cloned and expanded into cell lines.

For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wigler et al., *Cell*, 11:223 (1977)), hypoxanthine-guanine phosphoribosyltransferase (Szybalska et al, *Proc. Natl. Acad. Sci., USA*, 48:2026 (1962)), and adenine phosphoribosyltransferase (Lowy et al., *Cell*, 22:817 (1980)) genes, which can be employed in tk⁻, hgprt⁻ or aprt⁻ cells respectively. Also, antimetabolite resistance-conferring genes can be used as the basis of selection; for example, the genes for dhfr, which confers resistance to methotrexate (Wigler et al., Proc. Natl. Acad. Sci., USA, 77:3567 (1980); O'Hare et al., Proc. Natl. Acad. Sci., USA, 78:1527 (1981); gpt, which confers resistance to mycophenolic acid (Mulligan et al, Proc. Natl. Acad. Sci., USA, 78:2072, (1981)); neo, which confers resistance to the aminoglycoside G-418 (Colberre-Garapin et al, J. Mol. Biol., 150:1 (1981)); and hygro, which confers resistance to hygromycin (Santerre et al, Gene, 30:147 (1984)). Recently, additional selectable genes have been described, namely trpB, which allows cells to utilize indole in place of tryptophan; hisD, which allows cells to utilize histinol in place of histidine (Hartman et al, Proc. Natl. Acad. Sci., USA, 85:804 (1988)); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory ed., (1987)).

The principal vectors contemplated for human gene therapy, are derived from retroviral origin. (Wilson, 1997, Clin. Exp. Immunol. 107(Sup. 1):31–32; Bank et al., 1996, Bioessays 18(12):999–1007; Robbins et al., 1998, Pharmacol. Ther. 80(1):35–47). The therapeutic potential of gene transfer and antisense therapy has stimulated the development of many vector systems for treating a variety of tissues. (vasculature, Stephan et al., 1997, Fundam. Clin. Pharmacol. 11(2):97–110; Feldman et al., 1997, Cardiovasc. Res. 35(3):391–404; Vassalli et al., 1997, Cardiovasc. Res. 35(3):459–69; Baek et al., 1998, Circ. Res. 82(3):295–305; kidney, Lien et al., 1997, Kidney Int. Suppl. 61:S85–8; liver, Ferry et al., 1998, Hum Gene Ther. 9(14):1975–81; muscle, Marshall et al., 1998, Curr. Opn. Genet. Dev. 8(3):360–5). In addition to these tissues, a critical target for human gene therapy is cancer, either the tumor itself, or associated tissues. (Runnebaum, 1997, Anticancer Res. 17(4B):2887–90; Spear et al., 1998, J. Neurovirol. 4(2):133–47).

Specific examples of viral gene therapy vector systems readily adaptable for use in the methods of the present invention are briefly described below. Retroviral gene delivery has been recently reviewed by Federspiel and Hughes (1998, Methods in Cell Biol. 52:179–214) which describes in particular, the avian leukosis virus (ALV) retrovirus family (Federspiel et al., Proc. Natl. Acad. Sci., USA, 93:4931 (1996); Federspiel et al., Proc. Natl. Acad. Sci., USA, 91:11241 (1994)). Retroviral vectors, including ALV and murine leukemia virus (MLV) are further described by Svoboda (1998, Gene 206:153–163).

Modified retroviral/adenoviral expression systems can be readily adapted for practice of the methods of the present invention. For example, murine leukemia virus (MLV) systems are reviewed by Karavanas et al., 1998, Crit. Rev. in Oncology/Hematology 28:7–30. Adenovirus expression systems are reviewed by Von Seggern and Nemerow in Gene Expression Systems (ed. Fernandez & Hoeffler, Academic Press, San Diego, Calif., 1999, chapter 5, pages 112–157).

Protein expression systems have been demonstrated to have effective use both in vivo and in vitro. For example, efficient gene transfer to human squamous cell carcinomas by a herpes simplex virus (HSV) type 1 amplicon vector has been described. (Carew et al., 1998, Am. J. Surg. 176:404–408). Herpes simplex virus has been used for gene transfer to the nervous system. (Goins et al., 1997, J. Neurovirol. 3 (Sup. 1):S80–8). Targeted suicide vectors using HSV-TK has been tested on solid tumors. (Smiley et al., 1997, Hum. Gene Ther. 8(8):965–77). Herpes simplex virus type 1 vector has been used for cancer gene therapy on colon carcinoma cells. (Yoon et al., 1998, Ann. Surg. 228 (3):366–74). Hybrid vectors have been developed to extend the length of time of transfection, including HSV/AAV (adeno-associated virus) hybrids for treating hepatocytes. (Fraefel et al., 1997, Mol. Med. 3(12):813–825).

Vaccinia virus has been developed for human gene therapy because of its large genome. (Peplinski et al., 1998, Surg. Oncol. Clin. N. Am. 7(3):575–88). Thymidine kinase-deleted vaccinia virus expressing purine nucleoside pyrophosphorylase has been described for use as a tumor directed gene therapy vector. (Puhlman et al., 1999, Human Gene Therapy 10:649–657).

Adeno-associated virus 2 (AAV) has been described for use in human gene therapy, however AAV requires a helper virus (such as adenovirus or herpes virus) for optimal replication and packaging in mammalian cells. (Snoeck et al., 1997, Exp. Nephrol. 5(6):514:20; Rabinowitz et al., 1998, Curr. Opn. Biotechnol. 9(5):470–5). However, in vitro packaging of an infectious recombinant AAV has been described, making this system much more promising. (Ding et al., 1997, Gene Therapy 4:1167–1172). It has been shown that the AAV mediated transfer of ecotropic retrovirus receptor cDNA allows ecotropic retroviral transduction of established and primary human cells. (Qing et al., 1997, J. Virology 71(7):5663–5667). Cancer gene therapy using an AAV vector expressing human wild-type p53 has been demonstrated. (Qazilbash et al., 1997, Gene Therapy 4:675–682). Gene transfer into vascular cells using AAV vectors has also been shown. (Maeda et al., 1997, Cardiovascular Res. 35:514–521). AAV has been demonstrated as a suitable vector for liver directed gene therapy. (Xiao et al., 1998, J. Virol. 72(12):10222–6). AAV vectors have been demonstrated for use in gene therapy of brain tissues and the central nervous system. (Chamberlin et al., 1998, Brain Res. 793(1–2):169–75; During et al., 1998, Gene Therapy 5(6):820–7). AAV vectors have also been compared with adenovirus vectors (AdV) for gene therapy of the lung and transfer to human cystic fibrosis epithelial cells. (Teramoto et al., 1998, J. Virol. 72(11):8904–12).

Chimeric AdV/retroviral gene therapy vector systems which incorporate the useful qualities of each virus to create a nonintegrative AdV that is rendered functionally integrative via the intermediate generation of a retroviral producer cell. (Feng et al., 1997, Nat. Biotechnology 15(9):866–70; Bilbao et al., 1997, FASEB J 11(8):624–34). This powerful new generation of gene therapy vector has been adapted for targeted cancer gene therapy. (Bilbao et al., 1998, Adv. Exp. Med. Biol. 451:365–74). Single injection of AdV expressing p53 inhibited growth of subcutaneous tumor nodules of human prostrate cancer cells. (Asgari et al., .1997, Int. J. Cancer 71(3):377–82). AdV mediated gene transfer of wild-type p53 in patients with advanced non-small cell lung cancer has been described. (Schuler et al., 1998, Human Gene Therapy 9:2075–2082). This same cancer has been the subject of p53 gene replacement therapy mediated by AdV vectors. (Roth et al., 1998, Semin. Oncol. 25(3 Suppl 8):33–7). AdV mediated gene transfer of p53 inhibits endothelial cell differentiation and angiogenesis in vivo. (Riccioni et al., 1998, Gene Ther. 5(6):747–54). Adenovirus-mediated expression of melanoma antigen gp75 as immunotherapy for metastatic melanoma has also been described. (Hirschowitz et al., 1998, Gene Therapy 5:975–983). AdV facilitates infection of human cells with ecotropic retrovirus and increases efficiency of retroviral infection. (Scott-Taylor, et al., 1998, Gene Ther. 5(5):621–9). AdV vectors have been used for gene transfer to vascular smooth muscle cells (Li et al., 1997, *Chin. Med. J. (Engl)* 110(12):950–4), squamous cell carcinoma cells (Goebel et al., 1998, *Otolarynol Head Neck Surg* 119(4):331–6), esophageal cancer cells (Senmaru et al., 1998, *Int J. Cancer* 78(3):366–71), mesangial cells (Nahman et al., 1998, *J. Investig. Med.* 46(5):204–9), glial cells (Chen et al., 1998, *Cancer Res.* 58(16):3504–7), and to the joints of animals (Ikeda et al., 1998, *J. Rheumatol.* 25(9):1666–73). More recently, catheter-based pericardial gene transfer mediated by AcV vectors has been demonstrated. (March et al., 1999, *Clin. Cardiol.* 22(1 Suppl 1):I23–9). Manipulation of the AdV system with the proper controlling genetic elements allows for the AdV-mediated regulable target gene expression in vivo. (Burcin et al., 1999, *PNAS (USA)* 96(2):355–60).

Alphavirus vectors have been developed for human gene therapy applications, with packaging cell lines suitable for transformation with expression cassettes suitable for use with Sindbis virus and Semliki Forest virus-derived vectors. (Polo et al., 1999, *Proc. Natl. Acad. Sci., USA*, 96:4598–4603). Noncytopathic flavivirus replicon RNA-based systems have also been developed. (Varnavski et al., 1999, *Virology* 255(2):366–75). Suicide HSV-TK gene containing sinbis virus vectors have been used for cell-specific targeting into tumor cells. (Iijima et al., 1998, *Int. J. Cancer* 80(1):110–8).

Retroviral vectors based on human foamy virus (HFV) also show promise as gene therapy vectors. (Trobridge et al., 1998, *Human Gene Therapy* 9:2517–2525). Foamy virus vectors have been designed for suicide gene therapy. (Nestler et al., 1997, *Gene Ther.* 4(11):1270–7). Recombinant murine cytomegalovirus and promoter systems have also been used as vectors for high level expression. (Manning et al., 1998, *J. Virol. Meth.* 73(1):31–9; Tong et al., 1998, *Hybridoma* 18(1):93–7).

Gene delivery into non-dividing cells has been made feasible by the generation of Sendai virus based vectors. (Nakanishi et al., 1998, *J. Controlled Release* 54(1):61–8).

In other efforts to enable the transformation of non-dividing somatic cells, lentiviral vectors have been explored. Gene therapy of cystic fibrosis using a replication-defective human immunodeficiency virus (HIV) based vector has been described. (Goldman et al., 1997, *Human Gene Therapy* 8:2261–2268). Sustained expression of genes delivered into liver and muscle by lentiviral vectors has also been shown. (Kafri et al., 1997, *Nat. Genet.* 17(3):314–7). However, safety concerns are predominant, and improved vector development is proceeding rapidly. (Kim et al., 1998, *J. Virol.* 72(2):994–1004). Examination of the HIV LTR and Tat yield important information about the organization of the genome for developing vectors. (Sadaie et al., 1998, *J. Med. Virol.* 54(2):118–28). Thus the genetic requirements for an effective HIV based vector are now better understood. (Gasmi et al., 1999, *J. Virol.* 73(3):1828–34). Self inactivating vectors, or conditional packaging cell lines have been described. (for example Zuffery et al., 1998, *J. Virol.* 72(12):9873–80; Miyoshi et al., 1998, *J. Virol.* 72(10):8150–7; Dull et al., 1998, *J. Virol.* 72(11):8463–71; and Kaul et al., 1998, *Virology* 249(1):167–74). Efficient transduction of human lymphocytes and CD34+ cells by HIV vectors has been shown. (Douglas et al., 1999, *Hum. Gene Ther.* 10(6):935–45; Miyoshi et al., 1999, *Science* 283 (5402):682–6). Efficient transduction of nondividing human cells by feline immunodeficiency virus (FIV) lentiviral vectors has been described, which minimizes safety concerns with using HIV based vectors. (Poeschla et al., 1998, *Nature Medicine* 4(3):354–357). Productive infection of human blood mononuclear cells by FIV vectors has been shown. (Johnston et al., 1999, *J. Virol.* 73(3):2491–8).

While many viral vectors are difficult to handle, and capacity for inserted DNA limited, these limitations and disadvantages have been addressed. For example, in addition to simplified viral packaging cell lines, Mini-viral vectors, derived from human herpes virus, herpes simplex virus type 1 (HSV-1), and Epstein-Barr virus (EBV), have been developed to simplify manipulation of genetic material and generation of viral vectors. (Wang et al., 1996, *J. Virology* 70(12):8422–8430). Adaptor plasmids have been previously shown to simplify insertion of foreign DNA into helper-independent Retroviral vectors. (1987, *J. Virology* 61(10):3004–3012).

Viral vectors are not the only means for effecting gene therapy, as several non-viral vectors have also been described. A targeted non-viral gene delivery vector based on the use of Epidermal Growth Factor/DNA polyplex (EGF/DNA) has been shown to result in efficient and specific gene delivery. (Cristiano, 1998, *Anticancer Res.* 18:3241–3246). Gene therapy of the vasculature and CNS have been demonstrated using cationic liposomes. (Yang et al., 1997, *J. Neurotrauma* 14(5):281–97). Transient gene therapy of pancreatitis has also been accomplished using cationic liposomes. (Denham et al., 1998, *Ann. Surg.* 227 (6):812–20). A chitosan-based vector/DNA complexes for gene delivery have been shown to be effective. (Erbacher et al., 1998, *Pharm. Res.* 15(9):1332–9). A non-viral DNA delivery vector based on a terplex system has been described. (Kim et al., 1998, 53(1–3):175–82). Virus particle coated liposome complexes have also been used to effect gene transfer. (Hirai et al., 1997, *Biochem. Biophys. Res. Commun.* 241(1):112–8).

Cancer gene therapy by direct tumor injections of nonviral T7 vector encoding a thymidine kinase gene has been demonstrated. (Chen et al., 1998, *Human Gene Therapy* 9:729–736). Plasmid DNA preparation is important for direct injection gene transfer. (Horn et al., 1995, *Hum. Gene Ther.* 6(5):656–73). Modified plasmid vectors have been adapted specifically for direct injection. (Hartikka et al., 1996, *Hum. Gene Ther.* 7(10):1205–17).

Thus, a wide variety of gene transfer/gene therapy vectors and constructs are known in the art. These vectors are readily adapted for use in the methods of the present invention. By the appropriate manipulation using recombinant DNA/molecular biology techniques to insert an operatively linked src or yes, or both (either active or inactive) into the selected expression/delivery vector, many equivalent vectors for the practice of the present invention can be generated.

E. Methods For Modulation of Vascular Permeability (VP)

The invention provides for a method for the modulation of vascular permeability (VP) of the blood vessels in a tissue associated with a disease process or condition, and thereby effect events in the tissue which depend upon VP. Generally, the method comprises administering to the tissue, associated with a disease process or condition, a composition comprising a VP-modulating amount of a Src or Yes protein, or mixture thereof, or nucleic acid vector expressing active or inactive Src or Yes, or both, according to the methods of this invention.

As described herein, any of a variety of tissues, or organs comprised of organized tissues, can be a location for VP in disease conditions including brain, skin, muscle, gut, connective tissue, joints, bones and the like tissue in which blood vessels are present.

The patient treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of tissue associated with diseases involving angiogenesis is desirable, particularly agricultural and domestic mammalian species.

Thus the method comprises administering to a patient a therapeutically effective amount of a physiologically tolerable composition containing a Src or Yes protein, or mixture thereof, or DNA vector for expressing a Src or Yes protein, or both, in practicing the methods of the invention.

The dosage ranges for the administration of a Src or Yes protein depend upon the form of the protein, and its potency, as described further herein, and are amounts large enough to produce the desired effect in which VP and the disease symptoms mediated by VP are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

A therapeutically effective VP modulating amount is an amount of Src or Yes protein or mixture thereof, or nucleic acid encoding for Src or Yes protein, sufficient to produce a measurable modulation of VP in the tissue being treated, ie., a VP-modulating amount. Modulation of VP can be measured by assay as described herein, or by other methods known to one skilled in the art. Modulation of VP can be measured by the Miller assay, as described herein, or by other methods known to one of skill in the art.

The Src or Yes protein or nucleic acid vector expressing the Src or Yes protein, or both, can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, compositions of the invention can be administered intravenously, intraperitoneally, intramuscularly, subcutaneously, intracavity, transdermally, and can be delivered by peristaltic means.

The therapeutic compositions containing a Src or Yes protein or nucleic acid vector expressing the Src or Yes protein can be conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

In one preferred embodiment the reagent is administered in a single dosage intravenously. Localized administration can be accomplished by direct injection or by taking advantage of anatomically isolated compartments, isolating the microcirculation of target organ systems, reperfusion in a circulating system, or catheter based temporary occlusion of target regions of vasculature associated with diseased tissues.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

There are a variety of diseases in which inhibition of angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth.

Similarly, vascular permeability is an important component of angiogenesis, and in its own right associated with detrimental pathologies. For example, damage due to stroke induced vascular permeability triggers inflammation related damage.

Thus, methods which inhibit vascular permeability in a tissue associated with a disease condition ameliorates symptoms of the disease and, depending upon the disease, can contribute to cure of the disease. In one embodiment, the invention contemplates inhibition of vascular permeability, per se, in a tissue associated with a disease condition. The extent of vascular permeability in a tissue, and therefore the extent of inhibition achieved by the present methods, can be evaluated by a variety of methods.

Thus, in one related embodiment, a tissue to be treated is an inflamed tissue and the vascular permeability to be inhibited is due to VEGF mediated stimulation. In this class the method contemplates inhibition of VP in arthritic tissues, such as in a patient with chronic articular rheumatism, in immune or non-immune inflamed tissues, in psoriatic tissue and the like.

In another related embodiment, a tissue to be treated is a retinal tissue of a patient with a retinal disease such as diabetic retinopathy, macular degeneration or neovascular glaucoma and the VP to be inhibited is retinal tissue VP where there is neovascularization of retinal tissue.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of VP inhibitor is typically conducted during or after chemotherapy, although it is preferably to inhibit VP after a regimen of chemotherapy at times where the tumor tissue will be responding to the toxic assault by inducing VP to recover by the provision of a blood supply and nutrients to the tumor tissue. In addition, it is possible to administer the vascular permeability inhibition methods after surgery where solid tumors have been removed as a prophylaxis against metastases.

Insofar as the present methods apply to inhibition vascular permeability involved with metastases, the methods can also apply to inhibition of metastases as formation, and to regression of established tumors.

Restenosis is a process of smooth muscle cell (SMC) migration and proliferation into the tissue at the site of percutaneous transluminal coronary angioplasty which hampers the success of angioplasty. The migration and proliferation of SMC's during restenosis can be considered a process of VP which is inhibited by the present methods. Therefore, the invention also contemplates inhibition of restenosis by inhibiting vascular permeability according to the present methods in a patient following angioplasty procedures. For inhibition of restenosis, the inactivated tyrosine kinase is typically administered after the angioplasty procedure because the coronary vessel wall is at risk of restenosis, typically for from about 2 to about 28 days, and more typically for about the first 14 days following the procedure.

The present method for inhibiting vascular permeability in a tissue associated with a disease condition, and therefore for also practicing the methods for treatment of vascular permeability-related diseases, comprises contacting a tissue in which increased vascular permeability is occurring, or is at risk for occurring, with a composition comprising a therapeutically effective amount of an inactivated Src and/or Yes protein or vector expressing the protein.

In cases where it is desirable to promote or potentiate VP, administration of an active Src and/or Yes protein to the tissue is useful. The routes and timing of administration are comparable to the methods described hereinabove for inhibition.

For example, manipulation of the permeability of the blood-brain barrier to modulate the access of drugs to the brain tissue is contemplated. An increase in vascular permeability of the blood-brain barrier will allow for drugs, that may normally not cross the barrier, to enter in to the brain tissues.

Refined modulation of angiogenesis in conjunction with VP may be desired, and thus a mixture of active and inactive forms of Src protein, Yes protein, or expressible nucleic acids encoding for Src or Yes protein can be administered.

Inhibition or potentiation of angiogenesis clearly occurs by 5 to 7 days after the initial contacting with the therapeutic composition of the examples. Similarly, modulation of VP can occur in a similar time frame. administration of the therapeutic composition. The time-limiting factors include rate of tissue absorption, cellular uptake, protein translocation or nucleic acid translation (depending on the therapeutic) and protein targeting. Thus, VP modulating effects can occur in as little as an hour from time of administration. Additional or prolonged exposure to inactive Src and/or Yes protein can also be done, utilizing the proper conditions. Thus, a variety of desired therapeutic time frames can be designed by modifying such parameters.

F. Therapeutic Compositions

The present invention contemplates therapeutic compositions useful for practicing the therapeutic methods described herein. Therapeutic compositions of the present invention contain a physiologically tolerable carrier together with a Src and Yes protein or vector capable of expressing a Src and/or Yes protein as described herein, dissolved or dispersed therein as an active ingredient. In a preferred embodiment, the therapeutic composition is not immunogenic when administered to a mammal or human patient for therapeutic purposes.

The Src and Yes protein can be active, inactive, or a mixture thereof depending upon the desired modulation. Preferred forms of Src and Yes are described above.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains a vascular permeability-modulating amount of a Src and/or Yes protein of the present invention, or sufficient recombinant DNA expression vector to express an effective amount of Src and/or Yes protein, typically formulated to contain an amount of at least 0.1 weight percent of Src or Yes protein per weight of total therapeutic composition. A weight percent is a ratio by weight of Src or Yes protein to total composition. Thus, for example, 0.1 weight percent is 0.1 grams of Src or Yes protein per 100 grams of total composition. For DNA expression vectors, the amount administered depends on the properties of the expression vector, the tissue to be treated, and the like considerations.

G. Article of Manufacture

The invention also contemplates an article of manufacture which is a labelled container for providing a therapeutically effective amount of a mixture of Src protein and Yes protein. An article of manufacture comprises packaging material and a pharmaceutical agent contained within the packaging material.

The pharmaceutical agent in an article of manufacture is any of the compositions of the present invention suitable for providing a Src and Yes protein, formulated into a pharmaceutically acceptable form as described herein according to the disclosed indications. Thus, the composition can comprise a Src and Yes protein, or a DNA molecule which is capable of expressing a Src protein, a DNA capable of expressing a Yes protein, or DNA capable of expressing both proteins. The article of manufacture contains an amount of pharmaceutical agent sufficient for use in treating a condition indicated herein, either in unit or multiple dosages.

The Src or Yes protein can be active or inactive, or a mixture thereof, depending upon the level of modulation desired. Preferred forms of active and inactive Src and Yes are described above.

The packaging material comprises a label which indicates the use of the pharmaceutical agent contained therein, e.g., for treating conditions assisted by the inhibition or potentiation of vascular permeability, and the like conditions disclosed herein. The label can further include instructions for use and related information as may be required for marketing. The packaging material can include container(s) for storage of the pharmaceutical agent.

As used herein, the term packaging material refers to a material such as glass, plastic, paper, foil, and the like capable of holding within fixed means a pharmaceutical agent. Thus, for example, the packaging material can be plastic or glass vials, laminated envelopes and the like containers used to contain a pharmaceutical composition including the pharmaceutical agent.

In preferred embodiments, the packaging material includes a label that is a tangible expression describing the contents of the article of manufacture and the use of the pharmaceutical agent contained therein.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of c-src or c-yes Expression Constructs

For preparing the expression constructs useful in modulating VP and angiogenesis by the methods of the present invention, c-src cDNA is manipulated and inserted into an expression construct/vector.

The cDNA sequence encoding for wild-type (i.e., endogenous) chicken c-src is shown in FIG. 1 (SEQ ID NO.:2) with the encoded amino acid residue sequence shown in FIG. 2 (SEQ ID NO.:3). The encoded protein sequence is translated from the cDNA nucleotide positions 112 to 1713. The nucleic acid sequence corresponding to the nucleic acid sequence of human c-src cDNA (SEQ ID NO.:4) and encoded amino acid residue (SEQ ID NO.:5) sequences are shown respectively in FIGS. 3 and 4. For the human protein sequence, the coding sequence begins at nucleotide position 134 to 1486 of the cDNA.

Wild-type as well as a number of mutated c-src cDNAs were prepared. Mutated c-src constructs were prepared by site-directed mutagenesis as described by Kaplan et al., *EMBO J.*, 13:4745–4756 (1994). The mutated c-src constructs for encoding mutated Src proteins for use in the methods of the present invention are described in Kaplan et al., id. Kaplan et al. describe various mutated c-Src constructs and encoded proteins of useful for the practice of this invention. For example, Kaplan et al. depict several products of chicken c-src alleles in their FIG. 1, including SrcA and Src251.

The present invention describes two categories of c-Src function to modulate VP. As previously discussed, one category contains Src molecules that increase VP and thus are considered to be active proteins. Wild-type Src along with various mutations are shown in the present invention to induce VP. One preferred mutation of wild type c-src which functions in this context with respect to its ability to induce blood vessel growth and VP is the Src A mutant having a point mutation at amino acid (aa) residue position 527 changing tyrosine 527 to phenylalanine. This site is normally a site for negative regulation by the c-Src kinase, referred to as kinase CSK. When CSK phosphorylates aa527 in the wild-type Src, the protein is inactivated. However, in mutated Src A at aa527, the regulatory tyrosine converted to phenylalanine thus conferring upon the protein a constitutively (i.e., permanently) active protein not subject to inactivation by phosphorylation.

Other mutations in Src are herein shown to have the opposite modulatory effect on VP, inhibiting VP instead of stimulating it. Such mutations are referred to as inactive Src mutations. Proteins having mutation that confer this inhibitory activity are also referred to as dominant negative Src proteins in that they inhibit VP, including that resulting from endogenous activity of Src as well as enhanced Src activity resulting from growth factor stimulation. Thus certain mutations of wild type c-src of the present invention can also function as a dominant negative with respect to their ability to block blood vessel growth and VP, and for example, therefore decrease VP in vivo.

Such preferred inhibitory c-Src protein includes the Src 251 in which only the first 251 amino acids of Src are expressed. This construct lacks the entire kinase domain and is therefore referred to as "kinase dead" Src protein. A second construct is the Src (K295M) mutation in which the lysine amino acid residue 295 is mutated into a methionine. This point mutation in the kinase domain prevents ATP binding and also blocks kinase-dependent Src functions related to vascular cell and tumor cell signaling and proliferation.

With respect to the point mutations, any mutation resulting in the desired inhibitory or stimulatory activity is contemplated for use in this invention. Fusion protein constructs combining the desired Src protein (mutation or fragment thereof) with expressed amino acid tags, antigenic epitopes, fluorescent protein, or other such protein or peptides are also contemplated, so long as the desired modulating effect of the Src protein is intact.

For example, for the activating mutation of Src at residue 527, as long as the resultant mutated amino acid residue is not tyrosine, serine, or threonine, the present invention contemplates that the presence of an alternate amino acid at the desired position will result in a Src protein with a desired active, VP promoting modulatory activity.

Src Family kinase Yes has been previously described, but not much has been known about its cellular function. (Burck et al., 1988, *The Oncogenes*, Springer-Verlag, New York, pp. 133–155; Marth et al., 1985, *Cell*, 43:393; Semba et al., 1986, *PNAS*(USA) 83:5459; Shibuya et al., 1982, *J. Virol.* 42:143; Yoshida et al., 1985, *Jpn. J. Cancer Res.* 76:559). Preferred active human Yes protein are encoded for by nucleic acid described in Sukegawa et al. (1987, *Mol. Cell Biol.* 7:41–47). Inactivating modifications to human Yes protein and nucleic acids encoding Yes can be accomplished as described for Src.

TABLE I

| Src/Mutation | Src Function | Effect on VP and Angiogenesis |
|---|---|---|
| c-Src | + active | stimulates |
| SrcA (T527F) | + active | stimulates |
| Src527 (point) | + active | stimulates |
| Src251 | − inactive | inhibits |
| Src (truncate) | − inactive | inhibits |
| Src (K295M) | − inactive | inhibits |
| Src295 (point) | − inactive | inhibits |

Figure 10:
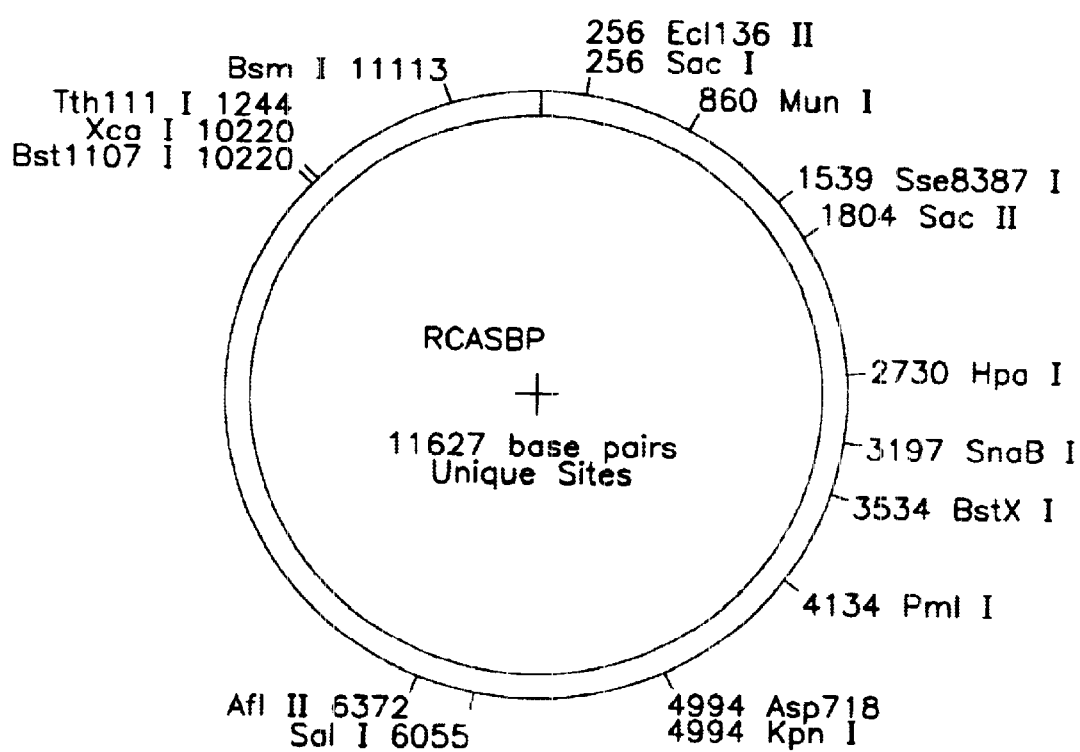
FIG. 10 is a diagram illustrating a restriction map of the RCASBP (RCAS) vector construct (SEQ ID NO:1).

One preferred expression construct for use in the present invention is the RCASBP(A) construct (SEQ ID NO.:1). This expression vector is based, on a series of replication competent avian sarcoma viruses with an enhanced Bryan polymerase (BP) for improved titre, and is specific for the A type envelope glycoprotein expressed on normal avian cells (Reviewed in Methods in Cell Biology, 52:179–214 (1997); see also, Hughes et al., 1987, *J. Virol.* 61:3004–3012; Fekete & Cepko, 1993, *Mol. Cellular Biol.* 13(4):2604–2613; Itoh et al., 1996, *Development* 122:291–300; and Stott et al., 1998, *BioTechniques* 24:660–666). The complete sequence of RCASBP(A) (SEQ ID NO.:1) is given in the sequence listing, and a restriction map of the construct is depicted as FIG. 10, referred to herein as RCAS.

The original Src 251 construct was subcloned by Dr. Pam Schwartzberg, at NIH in Dr. Harold Varmus' laboratory. Briefly, cloning of a src cDNA sequence for expression thereof was accomplished by inserting a linker containing Not I-BstB1-Not I restriction sites into a unique Not I site in the 5' end of Src 251. Src has a unique Cla I site at the 3' end. Digestion of Src 251 with BstB1 and Cla I generated a BstB1-ClaI fragment which was then ligated into the Cla I site on RCASBP(A). A BstB11 overhang allows for ligation with a Cla I overhang that will not be recut with Cla I. The src constructs suitable for use in practicing the present invention are readily obtained in the above vector by first digesting the RCAS vector containing Src 251 with Not I and Cla I (in a DAM+ background) to allow for insertion of a similarly digested Src cDNA. Therefore this initial RCASBP(A) construct containing Src 251 was further used to subclone all other Src constructs as described above and in Kaplan et al. (1994, *The EMBO J.* 13(20):4745–4756), into RCASBP(A) via a Not I-Cla I fragment generated through the Src 251 construction. To produce the desired c-src mutations in the cDNA, standard site-directed mutagenesis procedures familiar to one of ordinary skill in the art were utilized. PCR primers designed to incorporate the desired mutations were also designed with restriction sites to facilitate subsequent cloning steps. Entire segments of Src encoding nucleic acid sequences are deleted from the nucleic acid constructs through PCR amplification techniques based on the known cDNA sequences of chicken, human and the like homologs of Src and subsequent formation of new constructs.

In one embodiment of the invention, the 3' PCR primer used to amplify src nucleic acids also encodes an in-frame sequence. Use of this primer adds a 9E10-myc epitope tag to the carboxyl terminus of the subsequent Src construct.

The following amino acids were added after amino acid 251 of Src to generate vector constructs containing the 9E10-myc epitope tag: VDMEQKLIAEEDLN (SEQ ID NO.: 6). Two separate PCRs were carried out for each construct and similar results were obtained. All mutant constructs constructed by PCR were also sequenced by PCR to confirm predicted DNA sequence of clones. Wild-type and mutated Src cDNAs for use in the expression systems of the present invention are also available from Upstate Biotech Laboratories, Lake Placid, N.Y. which sells avian as well as human src, and several kinase dead and activated mutated forms.

Alternative expression vectors for use in the expressing the Src or Yes proteins of the present invention also include adenoviral vectors as described in U.S. Pat. Nos. 4,797,368, 5,173,414, 5,436,146, 5,589,377, and 5,670,488. Alternative methods for the delivery of the Src or Yes modulatory proteins include delivery of the Src or Yes cDNA with a non-viral vector system as described in U.S. Pat. No. 5,675,954 and delivery of the cDNA itself as naked DNA as described in U.S. Pat. No. 5,589,466. Delivery of constructs of this invention is also not limited to topical application of a viral vector as described in the CAM assay system below. For example, viral vector preparations are also injected intravenously for systemic delivery into the vascular bed. These vectors are also targetable to sites of increased neovascularization by localized injection of a tumor, as an example.

In vitro expressed proteins are also contemplated 10 for delivery thereof following expression and purification of the selected Src protein by methods useful for delivery of proteins or polypeptides. One such method includes liposome delivery systems, such as described in U.S. Pat. Nos. 4,356,167, 5,580,575, 5,542,935 and 5,643,599. Other vector and protein delivery systems are well known to those of ordinary skill in the art for use in the expression and/or delivery of the Src or Yes proteins of the present invention.

2. Characterization of the Untreated Chick Chorioallantoic Membrane (CAM)

A. Preparation of the CAM

Angiogenesis can be induced on the chick chorioallantoic membrane (CAM) after normal embryonic angiogenesis has resulted in the formation of mature blood vessels. Angiogenesis has been shown to be induced in response to specific cytokines or tumor fragments as described by Leibovich et al., *Nature*, 329:630 (1987) and Ausprunk et al., *Am. J. Pathol.*, 79:597 (1975). CAMs were prepared from chick embryos for subsequent induction of angiogenesis and inhibition thereof. Ten day old chick embryos were obtained from McIntyre Poultry (Lakeside, Calif.) and incubated at 37° C. with 60% humidity. A small hole was made through the shell at the end of the egg directly over the air sac with the use of a small crafts drill (Dremel, Division of Emerson Electric Co. Racine Wis.). A second hole was drilled on the broad side of the egg in a region devoid of embryonic blood vessels determined previously by candling the egg. Negative pressure was applied to the original hole, which resulted in the CAM (chorioallantoic membrane) pulling away from the shell membrane and creating a false air sac over the CAM. A 1.0 centimeter (cm)×1.0, cm square window was cut through the shell over the dropped CAM with the use of a small model grinding wheel (Dremel). The small window allowed direct access to the underlying CAM.

The resultant CAM preparation was then either used at 6 days of embryogenesis, a stage marked by active neovascularization, without additional treatment to the CAM reflecting the model used for evaluating effects on embryonic neovascularization or used at 10 days of embryogenesis where angiogenesis has subsided. The latter preparation was thus used in this invention for inducing renewed angiogenesis in response to cytokine treatment or tumor contact as described below.

3. CAM Angiogenesis Assay

A. Angiogenesis Induced by Growth Factors

Angiogenesis has been shown to be induced by cytokines or growth factors. Angiogenesis was induced by placing a 5 millimeter (mm)×5 mm Whatman filter disk (Whatman Filter paper No.1) saturated with Hanks Balanced Salt Solution (HBSS, GIBCO, Grand Island, N.Y.) or HBSS containing 2 micrograms/milliliter ($\mu$g/ml) recombinant basic fibroblast growth factor (bFGF) or vascular endothelial cell growth factor (VEGF) (Genzyme, Cambridge, Mass.) on the CAM of either a 9 or 10 day chick embryo in a region devoid of blood vessels and the windows were latter sealed with tape. Other concentrations of growth factors are also effective at inducing blood vessel growth. For assays where inhibition of angiogenesis is evaluated with intravenous injections of antagonists, angiogenesis is first induced with 1–2 ug/ml bFGF or VEGF in fibroblast growth medium. Angiogenesis was monitored by photomicroscopy after 72 hours.

B. Embryonic Angiogenesis

The CAM preparation for evaluating the effect of angiogenesis inhibitors on the natural formation of embryonic neovasculature is the 6 day embryonic chick embryo as previously described. At this stage in development, the blood vessels are undergoing de novo growth and thus provides a useful system for assessing angiogenesis modulation by the Src proteins of the present invention. The CAM system is prepared as described above with the exception that the assay is performed at embryonic day 6 rather than at day 9 or 10.

4. Modulation of Angiogenesis as Measured in the CAM Assay

To assess the effect of Src proteins on angiogenesis, the following assays were performed on 10 day old chick CAM preparations. Five $\mu$g of RCAS constructs prepared as described in Example 1 were transfected into the chicken immortalized fibroblast line, DF-1 (gift of Doug Foster, U. of Minn.). This cell line as well as primary chick embryo fibroblasts were capable of producing virus, however the DF-1 cell line produced higher titres. Viral supernatants were collected from subconfluent DF-1 producer cell lines in serum free CLM media [composition: F-10 media base supplemented with DMSO, folic acid, glutamic acid, and MEM vitamin solution]. Thirty-five ml of viral supernatant were concentrated by ultracentrifugation at 4° C. for 2 hours at 22,000 rpm. These concentrated viral pellets were resuspended in ⅟₁₀₀ the original volume in serum-free CLM media, aliquoted and stored at −80° C. The titre was assessed by serial dilution of a control viral vector having a nucleotide sequence encoding green fluorescent protein (GFP), referred to as RCAS-GFP, infection on primary chick embryo fibroblasts that were incubated for 48–72 hours. The titres of viral stock that were obtained following concentration routinely exceeded $10^8$ I.U./ml. For the CAM assay using the viral stocks, cortisone acetate soaked Whatman filter disks 6 mm in diameter were prepared in 3 mg/ml cortisone acetate for 30 minutes in 95% ethanol. The disks were dried in a laminar flow hood and then soaked on 20 $\mu$l of viral stock per disk for 10 minutes. These disks were applied to the CAM of 9 or 10 day chick embryos and sealed with cellophane tape and incubated at 37° C. for 18–24 hr. Then either mock PBS or growth factors were added at a concentration of 5 $\mu$g/ml to the CAM in a 20 $\mu$l volume of the appropriate virus stock as an additional boost of virus to the CAM tissue. After 72 hours, the CAMs were harvested and examined for changes in the angiogenic index as determined by double blind counting of the number of branch points in the CAM underlying the disk. For kinase assays, the tissue underlying the disk was harvested in RIPA, homogenized with a motorized grinder and Src immunoprecipitated from equivalent amounts of total protein and subjected to an in vitro kinase assay using a FAK-GST fusion protein as a substrate. For the immunofluorescence studies, CAM tissue underlying the disks were frozen in OCT, a cryopreservative, sectioned at 4 $\mu$m, fixed in acetone for 1 minute, incubated in 3% normal goat serum for 1 hour, followed by an incubation in primary rabbit anti-phosphorylated ERK antibody as described previously (Eliceiri et al., *J. Cell Biol.*, 140:1255–1263 (1998), washed in PBS and detected with a fluorescent secondary antibody.

A. Activation of Endogenous Src by bFGF or VEGF

To assess the effects of growth factors on Src activity in modulating angiogenesis, the following assays were performed. Tissue extracts of 10 day old chick CAMs that had been exposed to bFGF or VEGF (2 $\mu$g/ml) for 2 hours were lysed. Endogenous Src was immunoprecipitated from equivalent amounts of total protein and subjected to an in vitro immune complex kinase assay using a FAK-GST fusion protein as a substrate, electrophoresed and transferred to nitrocellulose.

The results of the assay are shown in FIG. 5 where the increase in Src activity is evident in the increased density of the gel with either bFGF or VEGF treatment as compared to untreated (mock) samples that are indicative of baseline Src activity in the CAM assay. Both bFGF and VEGF resulted in approximately a 2 fold increase of endogenous Src activity present in the CAM. The above kinase assay blot was also probed with an anti-Src antibody as a loading control for equivalent Src and IgG content.

B. Effect of Retrovirus-Mediated Gene Expression of Src A on Angiogenesis in the Chick CAM The following assay was performed to assess the effect of mutated Src proteins on angiogenesis in the CAM preparation. For the assay, 9 day old chick CAMs were exposed to RCAS-Src A or RCAS-GFP expressing retroviruses or buffer for 72-hour following the protocol described above.

Figure 6A:
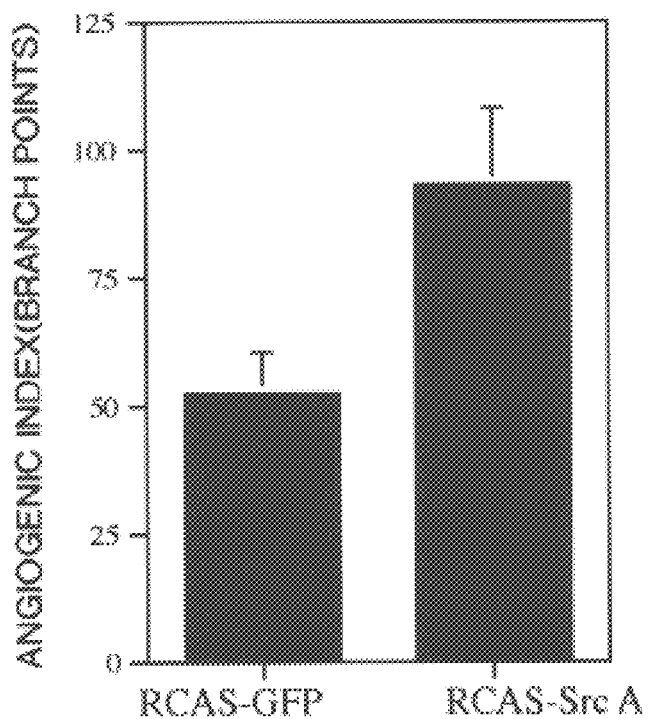
FIGS. 6A and 6B illustrate the effect of retrovirus-mediated gene expression of c-Src A on angiogenesis in the Chick CAM as described in Example 4. Nine-day-old chick CAMs were exposed to RCAS-Src A (active mutated c-Src) or control RCAS-GFP (Green Fluorescent Protein; a fluorescent indicator protein) retroviruses or buffer for 72 h. The level of angiogenesis was quantified as shown in FIG. 6A with representative photomicrographs (4×) in FIG. 6B corresponding to each treatment taken with a stereomicroscope.
Figure 6B:
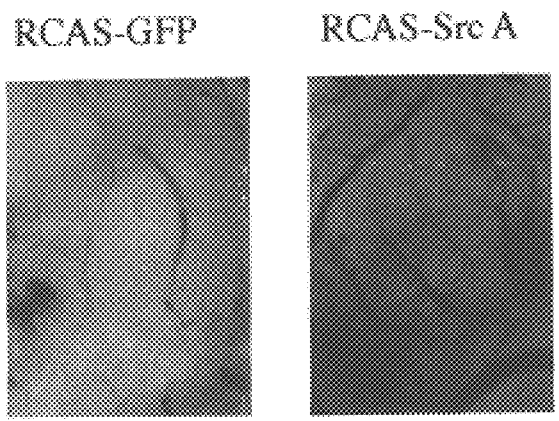

The results of this assay are shown in FIG. 6A where the level of angiogenesis was quantified as described above. Representative photomicrographs (4×) were taken with a stereomicroscope as shown in FIG. 6B. Baseline endogenous Src activity has an angiogenic index of approximately 50. In contrast, CAMs treated with retroviral vector-expressed RCAS-Src A having a point mutation at amino acid residue position 527 from a tyrosine to a phenylalanine resulted in an enhancement (induction) of angiogenesis of an angiogenic index of approximately 90. The enhancement of Src-A mediated angiogenesis is also evident in the photographs shown in FIG. 6B.

C. Retroviral Expression of Src A Activates Vascular MAP Kinase Phosphorylation

The effect of Src A as compared to growth factors VEGF and PMA on vascular MAP kinase phosphorylation was also assessed following the assay procedures described above and herein. Tissue extracts of 10 day old chick CAMs exposed to VEGF or PMA (another mitogen at a comparable concentration) for 30 minutes were compared to those infected with Src A-expressing retrovirus for 48 hours. Src was than immunoprecipitated from equivalent amounts of total protein extract and subjected to an in vitro immune complex kinase assay using a FAK-GST fusion protein as a substrate, electrophoresed and transferred to nitrocellulose.

Figure 7A:
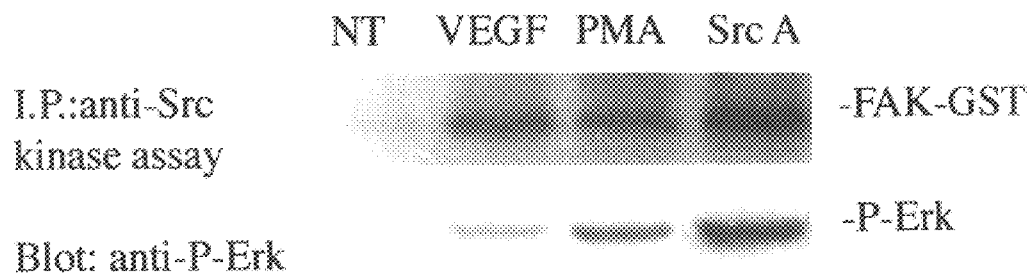
FIGS. 7A and 7B illustrate the retroviral expression of c-Src A in activating vascular MAP kinase phosphorylation.

The results of this assay are shown in FIG. 7A where untreated CAMs (NT) exhibit base-line endogenous Src-mediated vascular MAP kinase phosphorylation. Both VEGF and PMA resulted in an approximate 2 fold increase over baseline. In contrast, Src A enhanced the activity approximately 5 to 10 fold over that seen with untreated samples.

Figure 7B:
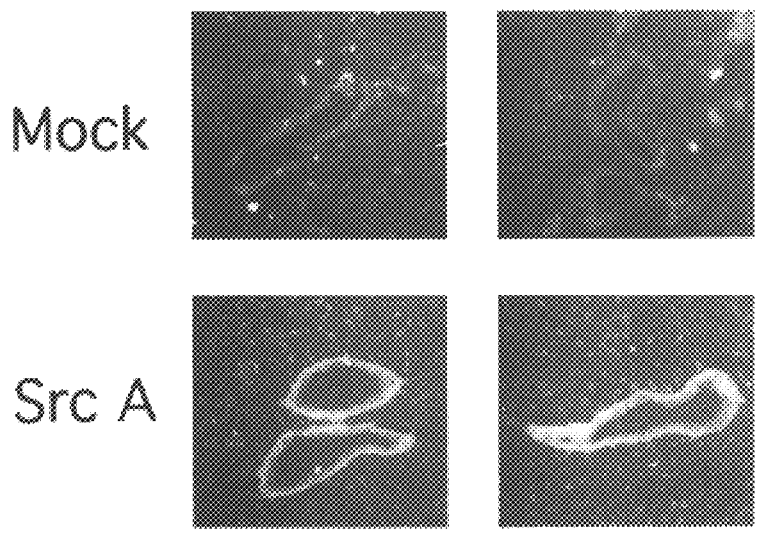

Aliquots of the above whole tissue lysates were also measured for endogenous ERK phosphorylation by immunoblotting with an anti-phospho-ERK antibody as shown in FIG. 7B. For this assessment, 10 day old CAMs were infected with either mock RCAS or RCAS that expresses SRC A. After two days, CAMs were dissected, cryopreserved in OCT and sectioned at 4 $\mu$m. Sections were immunostained with an anti-phosphorylated ERK antibody (New England Biolabs), washed and detected with a goat anti-rabbit FITC-conjugated secondary antibody. Fluorescent images were captured on a cooled-CCD camera (Princeton Inst.). The photomicrographs indicate enhanced immunofluorescence with Src A-treated preparations compared to mock controls.

D. Selective Requirement for Src Activity During VEGF, but Not bFGF-Induced Angiogenesis To assess the effect of Src modulatory activity on growth factor induced angiogenesis, the following assays were performed. Nine day old chick CAMs were exposed to the retroviral vector preparation that expressed the dominant negative Src mutation referred to as Src 251 or Src K295M as previously described. RCAS-Src 251 or control RCAS-GFP retroviruses or buffer CAMS were treated for 20 hours and then incubated for an additional 72 hours in the presence or absence of bFGF or VEGF.

The level of angiogenesis, quantified as described above, is shown in FIG. 8A. Representative photomicrographs (6×), shown in FIG. 8B, were taken with a stereomicroscope. FIG. 8C illustrates a blot probed with an anti-Src antibody to confirm the expression of Src 251 in transfected cells as compared to mock treatments.

The results of the assays described above indicate that both bFGF and VEGF treated CAMS in the presence of RCAS-GFP controls induced angiogenesis over the Src-mediated baseline angiogenesis seen with mock or untreated CAM preparations. The expressed dominant negative mutant Src 251 was effective at inhibiting VEGF-induced angiogenesis back to baseline levels while not effective at inhibiting bFGF-mediated angiogenesis. The photomicrographs shown in FIG. 8B pictorially confirm the data shown in FIG. 8A. Thus, retrovirally expressed Src 251 is an effective angiogenesis inhibitor, when angiogenesis is induced with VEGF.

Applications of the Src proteins of this invention with other angiogenesis models as described in the Examples below are contemplated in the present invention.

5. Regression of Tumor Tissue Growth With Src Modulators as Measured by In Vivo Rabbit Eye Model Assay The effect of Src modulators on growth factor-induced angiogenesis can be observed in naturally transparent structures as exemplified by the cornea of the eye. New blood vessels grow from the rim of the cornea, which has a rich blood supply, toward the center of the cornea, which normally does not have a blood supply. Stimulators of angiogenesis, such as bFGF, when applied to the cornea induce the growth of new blood vessels from the rim of the cornea. Antagonists of angiogenesis, applied to the cornea, inhibit the growth of new blood vessels from the rim of the cornea. Thus, the cornea undergoes angiogenesis through an invasion of endothelial cells from the rim of the cornea into the tough collagen-packed corneal tissue which is easily visible. The rabbit eye model assay therefore provides an in vivo model for the direct observation of stimulation and inhibition of angiogenesis following the implantation of compounds directly into the cornea of the eye.

In Vivo Rabbit Eye Model Assay Demonstrate Angiogenesis Induced by Growth Factors Angiogenesis is induced in the in vivo rabbit eye model assay with growth factors bFGF or VEGF and is described in the following sections.

Hydron polymer pellets containing growth factor are prepared as described by D'Amato, et al., *Proc. Natl. Acad. Sci., USA*, 91:4082–4085 (1994). The individual pellets contain 650 ng of the growth factors separately bound to sucralfate (Carafet, Marion Merrell Dow Corporation) to stabilize the growth factor and ensure its slow release into the surrounding tissue. In addition, hydron pellets are prepared containing a desired Src-expressing retrovirus as previously described. The pellets are cast in specially prepared Teflon pegs that have a 2.5 mm core drilled into their surfaces. Approximately 12 $\mu$l of casting material is placed into each peg and polymerized overnight in a sterile hood. Pellets are then sterilized by ultraviolet irradiation. Effects of Src proteins are then assessed as previously described.

6. In Vivo Regression of Tumor Tissue Growth With Src Modulators as Measured by Chimeric Mouse:Human Assay An in vivo chimeric mouse:human model is generated by replacing a portion of skin from a SCID mouse with human neonatal foreskin. The in vivo chimeric mouse:human model is prepared essentially as described in Yan, et al., *J. Clin. Invest.*, 91:986–996 (1993). Briefly, a 2 cm$^2$ square area of skin is surgically removed from a SCID mouse (6–8 weeks of age) and replaced with a human foreskin. The mouse is anesthetized and the hair removed from a 5 cm$^2$ area on each side of the lateral abdominal region by shaving. Two circular graft beds of 2 cm$^2$ are prepared by removing the full thickness of skin down to the fascia. Full thickness human skin grafts of the same size derived from human neonatal foreskin are placed onto the wound beds and sutured into place. The graft is covered with a Band-Aid which is sutured to the skin. Micropore cloth tape is also applied to cover the wound.

The M21-L human melanoma cell line or MDA 23.1 breast carcinoma cell line (ATCC HTB 26; $\alpha_v\beta_3$ negative by immunoreactivity of tissue sections with mAb LM609), are used to form the solid human tumors on the human skin grafts on the SCID mice. A single cell suspension of 5 ×10$^6$ M21-L or MDA 23.1 cells is injected intradermally into the human skin graft. The mice are then observed for 2 to 4 weeks to allow growth of measurable human tumors.

After a measurable tumor is established, retrovirus preparations of the present invention or PBS is injected into the mouse tail vein. Following a 2–3 week period, the tumor is excised and analyzed by weight and histology. The effect of expressed Src proteins of the present invention on the tumors is then assessed.

7. In Vitro Regression of Human Tumor Tissue Growth With Src Modulators as Measured by CAM Assay Tumor growth depends on angiogenesis (Folkman, 1992, *J.Biol.Chem.* 267:10931–10934; Weidner et al., 1991, *N.E. J. Med.* 324:1–8; Brooks et al., 1994, *Cell* 79:1157–1164). In fact, recent reports suggest that tumor growth is susceptible to the anti-angiogenic effects of VEGF receptor antagonists (Kim et al., 1993, *Nature* 362:8451–844). Therefore, we examined whether suppression of angiogenesis by delivery of kinase-deleted Src 251 would influence the growth of a human medulloblastoma (DAOY), a highly angiogenic tumor known to produce VEGF and very little bFGF.

The 3 and 6 day DAOY medulloblastoma tumor growth assays were performed in the chick CAM essentially as previously described (Brooks et al., 1994, supra). 5×10$^6$ DAOY cells cultured in RPMI 1640 containing 10% fetal calf serum were washed an seeded on the CAM of a 10 day embryo to produce DAOY tumor fragments. After 7 days 50 mg tumor fragments were dissected and reseeded on another 10 day embryo and incubated for another 3 or 6 days with the topical application (25 μl) of either control RCAS-GFP retrovirus, RCAS-Src 251, or mock treatment. Using the whole tissue confocal imaging of infected tumors as a guide we were able to determine that there was significant expression of the RCAS constructs around and within the tumor fragment with this topical approach. Tumor resections and weighing were performed in a double blind manner removing only the easily definable solid tumor mass (Brooks et al., 1994, supra). The wet tumor weights after 3 or 6 days were compared with initial weight and the percent change of tumor weight determined for each group.

These tumors readily grow on the CAM and produces active angiogenesis (FIG. 9) allowing us to selectively target the avian-derived tumor vasculature by using an avian-specific RCAS retrovirus.

Figure 9A:
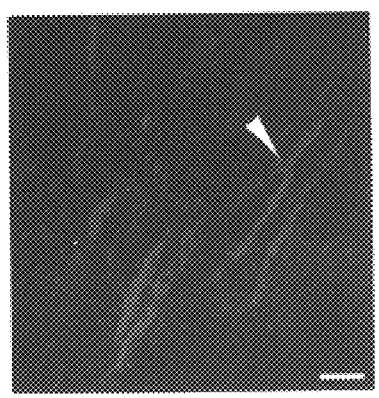
FIGS. 9A–9C illustrate the results of retroviral delivery of RCAS-Src 251 to human tumors.
Figure 9B:
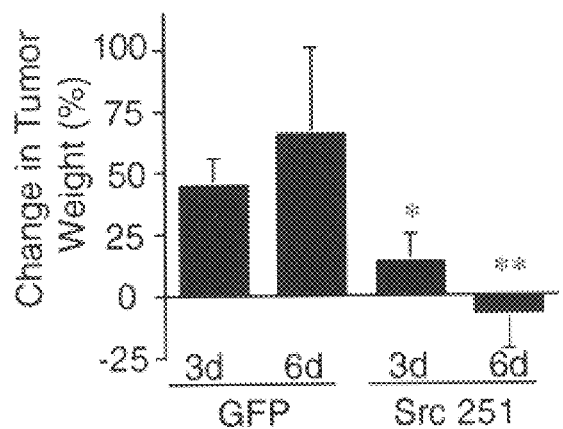
Figure 9C:
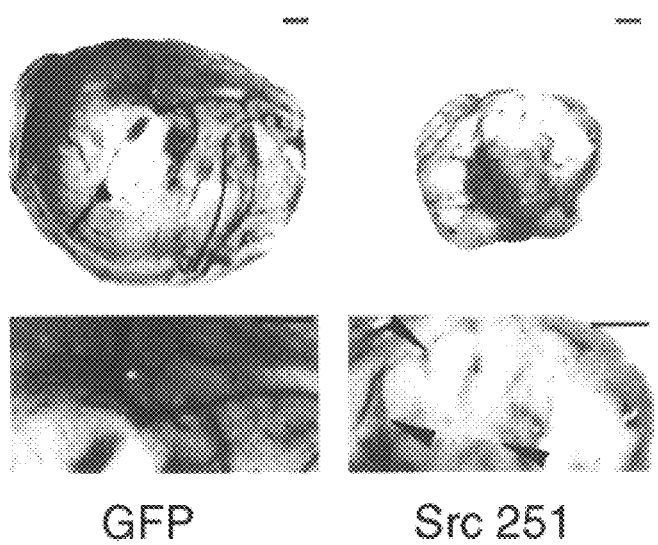

FIG. 9, depicts results that show retroviral delivery of RCAS-Src 251 to human tumors growing on the chick CAM reverses tumor growth. FIG. 9A shows human medulloblastomas that were grown on the CAM of chick embryos as described above. Retrovirus containing RCAS-GFP or RCAS-Src 251 was topically applied to preestablished tumors of greater than 50 mg. A representative micrograph of a medulloblastoma tumor fragment infected with RCAS-GFP expressing GFP reveals exclusive expression in the tumor blood vessels (arrowhead) as detected by optical sectioning with a Bio Rad laser confocal scanning microscope (bar=500 μm). FIG. 9B shows results from tumors treated as above that were allowed to grow for 3 or 6 days after which they were resected and wet weights determined. Data are expressed as the mean change in tumor weight (from the 50 mg tumor starting weight) +/−SEM of 2 replicates. RCAS-Src 251 had a significant impact on tumor growth after 3 days (*, P<0.002) and 6 days (**, P<0.05). FIG. 9C shows representative stereomicrographs of medulloblastoma tumors surgically removed from the embryos were taken with an Olympus stereomicroscope (bar=350 μm). (Lower panel) A high magnification micrograph of each tumor showing the vasculature of each tumor in detail (bar=350 μm). The arrowhead indicates blood vessel disruption in RCAS-Src251-treated tumors.

The results show that delivery of RCAS containing Src 251 to preestablished medulloblastomas resulted in selective viral expression in the tumor-associated blood vessels (FIG. 9A) and this ultimately led to the regression of these tumors within the span of six days (FIG. 9B). Importantly, the tumor-associated blood vessels in animals treated with virus containing Src 251 were severely disrupted and fewer in number compared to the tumor vessels in control animals (FIG. 9C). The fact that RCAS-GFP infected tumors showed GFP localization only in the tumor vasculature suggests that the anti-tumor effects observed with retrovirally delivered Src 251 were due to its anti-angiogenic properties.

8. Src Requirement for Endothelial Cell Survival During VGEF-, but not bFGF-Mediated Angiogenesis Recent evidence suggests that growth factor receptors (Choi and Ballermann, 1995, *J.Biol.Chem.* 270:21144–21150; Satake et al., 1998, *Biochem. Biophys. Res. Comm.* 244:642–646) and integrins (Meredith et al., 1993, *Mol.Biol.Cell* 4:953–961; Brooks et al., 1994a, *Science* 264:569–571) promote survival of angiogenic endothelial cells. The fact that both growth factors and adhesion receptors also regulate Src activity prompted the examination of the role of Src in endothelial cell survival during angiogenesis. CAMs stimulated with either bFGF or VEGF were infected with retrovirus containing Src 251, and cryostat sections of these tissues were examined for the presence of apoptotic cells.

Briefly, cryosections of CAMs treated with RCAS-GFP or RCAS-Src 251 treated with bFGF or VEGF were analyzed for apoptic cells using the Apoptag Kit (Oncor, Gaithersburg, Md.). Sections were also immunostained with a rabbit polyclonal anti-vWf (biogenix, San Ramon, Calif.) and counterstained with 1 ug/ml DAPI. Fluorescent images were captured with a cooled CCD camera (Roper, Trenton, N.J.), and the fluorescent images were processed and exposure matched between experimental treatments as previously described (Ellcelri et al. 1998, supra).

To measure the apoptic index of retrovirus-infected CAM tissues, FITC-conjugated annexin V (Clontech, Palo Alto, Calif.) was used to stain cell suspensions, and the washed cells were analyzed by flow cytometry. Cell suspensions of CAM cells were prepared from mock- or virus-infected CAMs by digestion with 0.1% (w/v) collagenase type IV (Worthington Biochemicals, Lakewood, N.J.), in RPMI 1640 of minced CAM tissue rocking for 1 hr at 37° C. as previously described (Brooks et al., 1994b) and filtered through 100 uM nylon mesh (Becton Dickinson, Fountain Lakes, N.J.). Fluorescence was measured with a FACscan flow cytometer (Becton Dickinson) to count 10,000 cells.

Measurement of vWf staining by FACs,was performed with parallel collagenase digested CAM tissue cell preparations, that were fixed in 1.8% paraformaldehyde, permeabilized in 70% ethanol, incubated the anti-vWf antibody, and detected with a FITC-conjugated secondary antibody.

Delivery of Src 251 promoted extensive TUNEL staining among the factor VIII-related antigen (von Willebrand factor [vWf]) positive blood vessels in VEGF- but not bFGF-, stimulated CAMS. In fact, minimal apoptosis was observed among other cell types in these CAMs, suggesting an endothelial cell-specific requirement for Src kinase activity for cell survival in VEGF-activated blood vessels. In a second series of experiments, retrovirus-infected CAMs stimulated with VEGF or bFGF were subjected to limited collagenase digestion to prepare a single cell suspension. These CAM-derived cells were shown to contain approximately 20%–50% endothelial cells (vWf positive) and analyzed for apoptosis by flow cytometric detection of annexin V-positive cells, an early apoptosis marker. Cells derived from VEGF-stimulated CAMs infected with Src 251 had significantly increased annexin V staining relative to cells from mock RCAS-GFP-infected CAMs treated with VEGF. In contrast, cells derived from mock-infected CAMs or those infected with RCAS-Src 251 and stimulated with bFGF exhibited little or no annexin V staining. In addition, no annexin V staining was detected among cells derived from nonstimulated or bFGF-stimulated CAMs. These data demonstrate that Src kinase activity is selectively required for endothelial cell survival during VEGF, but not bFGF-mediated angiogenesis in the CAM.

Figure 13A:
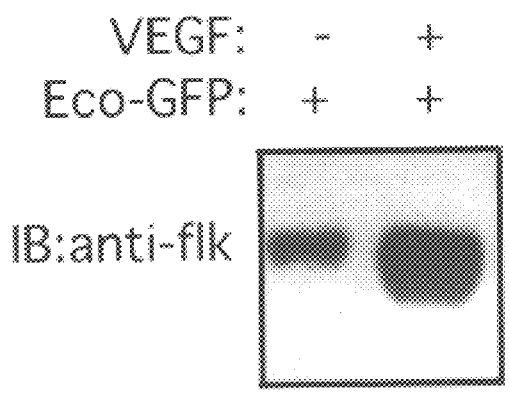
FIGS. 13A–13C depict results from retroviral delivery of Src 251 and CSK in a subcutaneous murine angiogenesis model.
Figure 13B:
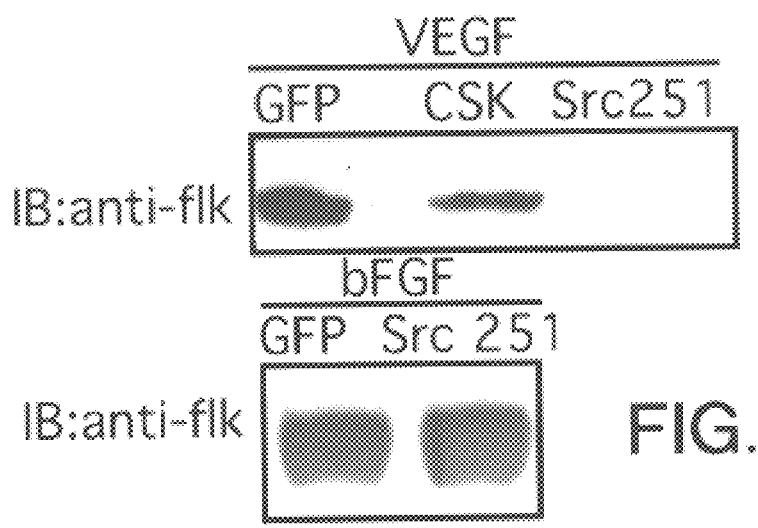
Figure 13C:
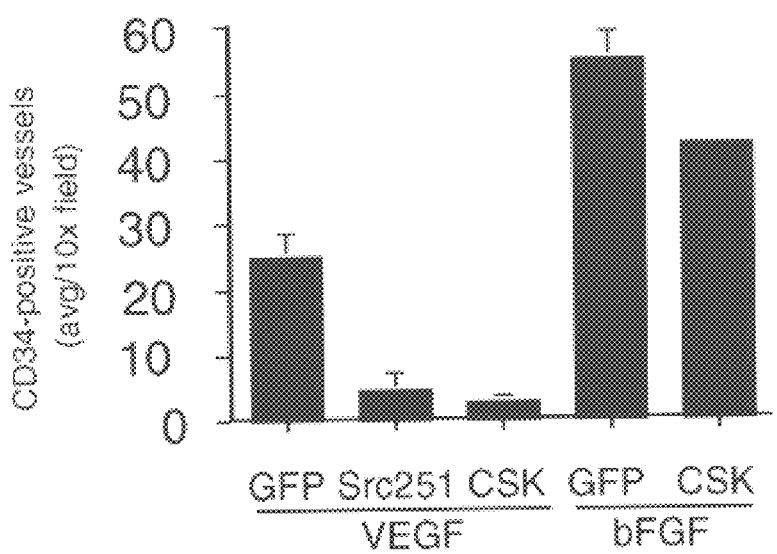

9. Selective Requirement for Src Kinase Activity in as Subcutaneous Murine Model of Angiogenesis To further analyze the role of Src in angiogenesis, a murine model was employed. In this case, angiogenesis was induced by subcutaneous injection of growth factor-depleted Matrigel supplemented with either bFGF (100 ng/ml) or VEGF (400 ng/ml) in athymic wehl(nu/nu) adult mice and analyzed after 5 days (Passaniti et al., 1992). Angiogenesis was quantitated by removing and homogenizing tissue, isolating the proteins., and immunoblotting with a VEGF receptor antibody (flk-1) (FIG. 13A) that is specific for endothelial cells. As observed in the chick, expression of the kinase-deleted Src 251 cDNA blocked VEGF-induced angiogenesis in this murine model while having no effect on bFGF-induced angiogenesis (FIG. 13B). To establish the role of endogenous Src in this model, tissues were infected with a retrovirus expressing Cak that inhibits endogenous Src activity by phosphorylation of the C-terminal regulatory site (Nada et al., 1991, Nature 361:68–72). Expression of Cak blocked VEGF-, but not bFGF-, induced angiogenesis (FIG. 13), confirming a role for endogenous Src activity in VEGF-mediated angiogenesis. Neovascularization of these virus-infected VEGF-stimulated tissues was confirmed by direct immunofluorescence with a FITC-conjugated anti-DC34 antibody (FIG. 13) or an anti-flk-1 antibody and quantitated by enumerating the number of positively stained CD34 blood vessels in each cryosection (FIG. 13C).

Briefly, angiogenesis was induced by a subcutaneous injection of growth factor depleted Matrigel containing saline or VEGF (400 ng/ml) with $2 \times 10^6$ ectropic packaging cells expressing GFP retrovirus in the flank of athymic wahl (nu/nu) mice and analyzed after 5 days of incubation. The neovascularization was quantitated by immunoblotting with a VEGF receptor antibody (flk-1) that is specific for endothelial cells. FIG. 15A depicts immunoblotting results. The effects of kinase-deleted Src-251, Csk, or GFP retrovirus on VEGF-(400 ng/ml) or bFGF-(400 ng/ml) induced angiogenesis was analyzed by immunoblotting the tissue lysates with an anti flk-1 antibody. An example of these results are depicted in FIG. 15B. The effect of the Src 251- and Csk-expressing retroviruses on VEGF-induced neovascularization was quantified by enumerating the number of CD34 positive vessels in tissue cross sections by indirect immunofluorescence in triplicate random fields at 20×. Cryosections of the plugs were also subjected to immunofluorescent staining with an anti-CD34 antibody or an anti-flk antibody, photographed, and quantitated as described above for the CAM angiogenesis assays.

Whole-mount direct fluorescence of RCAS-GFP-infected tumor fragment was accomplished by dissecting a tumor fragment and imaging the unfixed tissue directly on a slide with a laser confocal microscope (MRC 1024: Bio-Rad, Hercules, Calif.).

10. The Effect of Intradermal Expression of VEGF in src$^{-/-}$ or src$^{+/-}$ Mice Ears Continuing the results obtained with chicken and mouse angiogenesis models, a direct genetic approach was employed to examine intradermal VEGF-induced angiogenesis in src$^{-/-}$ mice. Also examined were effects on vascular permeability, since it was known that VEGF both initiates new blood vessel growth and can promote vascular permeability (Senger et al., 1983 Science 218:983–985; Ferrera and Davis-Smyth, 1997, Endocr.Rev. 16:4–25).

Intradermal injections of adenovirus expressing a human VEGF cDNA were performed in the ear of src$^{-/-}$ and src$^{+/-}$ mice, while control β-galactosidase expressing adenovirus was injected into the opposite ear of each mouse. VEGF-dependent new blood vessel growth in src$^{+/-}$ ears was first detectable within 48 hr, and neovascularization was analyzed after 5 days.

Briefly, pp60$^{c\text{-}src}$, pp60$^{c\text{-}yes}$, pp60$^{c\text{-}fyn}$, deficient mice (129/8v/Ev×C57B16/J) were generated as previously described (Soriano et al., 1991, Cell 64:693–702). Additional stocks were obtained from Jackson labs. Mouse ears were injected intradermally (Eriksson et al., 1980, Microvasc.Res. 19:374–378) with 5 μl of adenovirus expressing either VEGF or β-galactosidase and the ears photographed after 5 days, with a stereoscope.

It was found that there were identical viral expression levels in src$^{+/-}$ and src$^{-/-}$ as determined by X-gal staining of β-galactosidase-adenovirus injected ears. In VEGF-injected src$^{-/-}$ ears, there was no significant decrease in angiogenesis as measured by counting branch points (p<0.05). However, surprisingly, the most apparent phenotype in these animals was the complete blockade of vascular leakage compared to the VEGF-injected src$^{+/-}$ ears. Examination of ears injected with VEGF confirms the extent of the vascular leakage in src$^{+/-}$ mice, that is essentially absent in the src$^{-/-}$ mice. The vascular leakage in these animals suggested that the VP activity, which has been associated with angiogenesis in vivo (Dvorak et al., 1995, Am.J.Pathol. 148:1029–1039), could be selectively disrupted in pp60$^{c\text{-}src}$ deficient mice.

11. VEGF Fails to Compromise the Blood-Brain Barrier in Mice Lacking pD60$^{c\text{-}src}$ The brain vasculature is characterized by a highly restrictive blood-brain barrier that prohibits small molecules from extravasating into the surrounding brain tissue. Tumor growth within the brain can compromise this barrier due in part to the production of angiogenic growth factors such as VEGF. Therefore, we examined the nature of the blood-brain barrier in src$^{+/-}$ or src$^{-/-}$ mice. In this case, VEGF or saline was stereotactically injected into the right or left hemisphere of the brain, respectively. All mice received systemic injections of Evan's blue dye to monitor VP activity.

Briefly, Saline or VEGF (200 ng in 2 ul) was injected stereotactically into the left or right frontal lobe 92 mm to the left/right of the midline, 0.5 mm rostral from bregma, and 3 mm in depth from the dura, respectively. The animals received an Evan's blue dye solution intravenously 30 min after injection, as described above. After an additional 30 min, the mice were perfused and the brains were removed. Evan's blue dye fluorescence was observed using confocal laser microscopy of fresh unfixed cryosections of the brain.

Vascular leakage of blood was localized to the VGEF-injected hemisphere in $src^{+/-}$ mice, but there was a complete absence of vascular leakage in $src^{-/-}$ mice. This was also the case when examing the VP by measuring the accumulation of Evan's blue dye as detected by epifluoresence analysis of cryostat sections of these brains. Thus, VEGF compromises the blood-brain barrier in a manner that depends on active $pp60^{c-src}$.

12. VEGF-Mediated VP, but not Inflammation-associated VP, DeDends on $pp60^{c-src}$ To further analyze and quantitate the effect of VEGF as a VP factor in $src^{+/-}$ or $src^{-/-}$ mice, a Miles assay (Miles & Miles, 1952) was used to quantitatively measure the vascular permeability in the skin of these animals. VEGF was injected intradermally in $src^{+/-}$ or $src^{-/-}$ mice that had received an intravenous systemic administration of Evan's blue dye. Within 15 min after injection of VEGF, there was a 3-fold increase in VP in $src^{+/-}$ mice. However, in $src^{-/-}$ mice no detectable VP activity was observed. Dye elution of the injected skin patches were quantitated and compared with control saline and bFGF. bFGF or saline controls injected adjacent to the VEGF showed no significant increase in VP.

Briefly, the Miles assay (Miles et al., 1962) was adapted for mice by injecting 10 $\mu$l of VEGF (400 ng/ml), allyl isothiocyanate (mustard oil, 20% w/v in mineral oil), or saline intradermally into mice that had previously been intravenously injected with 100 $\mu$l of 0.5% Evan's blue dye. After 15 min, the skin patches were dissected, photographed, and eluted at 58° C. with formalin and quantitated with a spectrophotometer.

Vascular leakage/permeability is also known to occur during inflammation, which allows for the accumulation of serum-associated adhesive protein and inflammatory cells in tissues. In fact, inflammatory mediators themselves directly promote vascular leakage. Therefore, one such inflammatory mediator, allyl isothiocyanate, also known as mustard oil (Inoue et al., 1997, supra), was tested in $src^{+/-}$ or $src^{-/-}$ mice for its capacity to produce VP. Unlike that observed in VEGF-stimulated $src^{-/-}$ animals, no decrease in the VP produced by the injection of the inflammatory mediator allyl isothiocyanate was detected. Thus, it can be concluded that Src plays a selective role in the VP activity induced with VEGF and does not influence VP associated with the inflammatory process.

13. VEGF-Mediated VP Activity Depends on Src and Yes, but Not Fyn

The specificity of the Src requirement for VP was explored by examining the VEGF-induced VP activity associated with SFKs such as Fyn or Yes, which, like Src, are known to be expressed in endothelial cells (Bull et al., 1994, *FEBS Letters*, 361:41–44; Kiefer et al., 1994, *Curr.Biol.* 4:100–109). It was confirmed that these three SFKs were expressed equivalently in the aortas of wild-type mice. Like $src^{-/-}$ mice, animals deficient in Yes were also defective in VEGF-induced VP. However, surprisingly, mice lacking Fyn retained a high VP in response to VEGF that was not significantly different from control animals. The disruption of VEGF-induced VP in $src^{-/-}$ or $yes^{-/-}$ mice demonstrates that the kinase activity of specific SFKs is essential for VEGF-mediated signalling event leading to VP activity but not angiogenesis.

The vascular permeability properties of VEGF in the skin of $src^{+/-}$ (FIG. 14A, left panel) or $src^{-/-}$ (FIG. 14A, right panel) mice was determined by intradermal injection of saline or VEGF (400 ng) into mice that have been intravenously injected with Evan's blue dye. After 15 min, skin patches were photographed (scale bar, 1 mm). The stars indicate the injection sites. The regions surrounding the injection sites of VEGF, bFGF or saline were dissected, and the VP quantitatited by elution of the Evan's blue dye in formamide at 58° C. for 24 hr, and the absorbance measured at 500 nm (FIG. 14B, left graph). The ability of an inflammation mediator (allyl isothiocyanate), known to induce inflammation related VP, was tested in $src^{+/-}$ or $src^{-/-}$ mice (FIG. 14B, right).

The ability of VEGF to induce VP was compared in $src^{-/-}$, $fyn^{-/-}$, or $yes^{-/-}$ mice in the Miles assay (FIG. 14C). Data for each of the Miles assays are expressed as the mean±SD of triplicate animals. $src^{-/-}$ and $yes^{-/-}$ VP defects compared to control animals were statistically significant (*p<0.05, paired t test), whereas the VP defects in neither the VEGF-treated $fyn^{-/-}$ mice nor the allyl isothiocyanate treated $src^{+/-}$ mice were statistically significant (**p<0.05).

The foregoing written specification is considered to be sufficient to enable one skilled in the art to practice the invention. The present invention is not to be limited in scope by any cell line deposit, since any deposited embodiment is intended as a single illustration of one aspect of the invention and any cell line that is functionally equivalent is within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

We claim:

1. A pharmaceutical composition comprising tyrosine kinase proteins Src and Yes, together with a pharmaceutically acceptable carrier wherein at least one of the Src protein and the Yes protein is an active kinase and at least one of the Src protein and the Yes protein is an inactive.

2. A pharmaceutical composition of claim 1 wherein said Src protein is Src-A.

3. A pharmaceutical composition of claim 1 wherein said Src protein has the amino acid sequence of SEQ ID NO: 3 and having at amino acid residue 527 any amino acid except for tyrosine, serine or threonine.

4. A pharmaceutical composition of claim 1 wherein said Src protein is inactive.

5. A pharmaceutical composition of claim 4 wherein said Src protein is Src K295M having the amino acid sequence of SEQ ID NO: 3 and having the lysine residue at position 295 replaced with a methionine residue.

6. A pharmaceutical composition of claim 4 wherein said Src protein is Src 251 having the amino acid sequence of residues 1 through 251 of SEQ ID NO: 3.

7. A pharmaceutical composition of claim 1 wherein said Yes protein is an inactive Yes protein.

8. An article of manufacture comprising packaging material and a pharmaceutical composition contained within said packaging material, wherein said pharmaceutical composition is capable of modulating vascular permeability in a tissue suffering from a disease condition, wherein said packaging material comprises a label which indicates that said pharmaceutical composition can be used for treating disease conditions by modulating vascular permeability, and wherein said pharmaceutical composition comprises a tyrosine kinase Src protein and Yes protein, in a pharmaceutically acceptable carrier and at least one of the Src protein and the Yes protein is an active kinase and at least one of the Src protein and the Yes protein is an inactive kinase.

9. An article of manufacture of claim 8 wherein said Src protein is an active Src.

10. An article of manufacture of claim 9 wherein said active Src protein is Src-A.

11. An article of manufacture of claim 9 wherein said Src protein has the amino acid sequence of SEQ ID NO: 3 and having at amino acid residue 527 ayamino acidaxcept for tyrosine, serine or threonine.

12. An article of manufacture of claim 8 wherein said Src protein is inactive.

13. An article of manufacture of claim 12 wherein said Src protein is Src K295M having the amino acid sequence of SEQ ID NO: 3 and having the lysine residue at position 295 replaced with a methionine residue.

14. An article of manufacture of claim 12 wherein said Src protein is Src 251 having the amino acid sequence of residues 1 through 251 of SEQ ID NO: 3.

15. An article of manufacture of claim 8 wherein said Yes protein is active.

16. An article of manufacture of claim 8 wherein said Yes protein is inactive.

* * * * *

UNITED STATES PATENT AND TRADEMARK OFFICE
CERTIFICATE OF CORRECTION

PATENT NO. : 6,685,938 B1
DATED : February 3, 2004
INVENTOR(S) : David A. Cheresh et al.

It is certified that error appears in the above-identified patent and that said Letters Patent is hereby corrected as shown below:

Column 7,
Line 61, "DETAILED DESCRIPTION OF THE DRAWINGS" should be
-- DETAILED DESCRIPTION OF THE INVENTION --.

Column 10,
Line 49, "considered:inactive" should be -- considered inactive --.

Column 13,
Line 44, "PRSET" should be -- pRSET --.
Line 54, "PSVL" should be -- pSVL --.

Column 21,
Line 10, after "metastases" delete "as".
Line 54, before "administration" insert -- Effects can occur within a short time after --.

Column 26,
Line 43, after "contemplated" delete "10".

Column 27,
Line 8, after "(cm)x1.0" delete the comma (,).

Column 34,
Line 55, "$pD60^{c-src}$" should be -- $pp60^{c-src}$ --

Column 35,
Line 19, "DeDends" should be -- Depends --.

Column 71,
Line 5, after "inactive" insert -- kinase --.

UNITED STATES PATENT AND TRADEMARK OFFICE
CERTIFICATE OF CORRECTION

PATENT NO. : 6,685,938 B1
DATED : February 3, 2004
INVENTOR(S) : David A. Cheresh et al.

It is certified that error appears in the above-identified patent and that said Letters Patent is hereby corrected as shown below:

Column 72,
Line 3, "ayamino acidaxcept" should be -- any amino acid except --.

Signed and Sealed this

Twenty-eighth Day of December, 2004

JON W. DUDAS
*Director of the United States Patent and Trademark Office*